United States Patent

Schnur et al.

[11] Patent Number: 5,932,566
[45] Date of Patent: Aug. 3, 1999

[54] ANSAMYCIN DERIVATIVES AS ANTIONCOGENE AND ANTICANCER AGENTS

[75] Inventors: Rodney Caughren Schnur, Mystic; Mikel Paul Moyer, Clinton; Randall James Gallaschun, Norwich, all of Conn.

[73] Assignee: Pfizer Inc., New York, N.Y.

[21] Appl. No.: 08/578,671

[22] PCT Filed: Jun. 16, 1994

[86] PCT No.: PCT/IB94/00160

§ 371 Date: Mar. 25, 1996

§ 102(e) Date: Mar. 25, 1996

[87] PCT Pub. No.: WO95/01342

PCT Pub. Date: Jan. 12, 1995

[51] Int. Cl.$^6$ .......................... C07D 233/14; A61K 31/33
[52] U.S. Cl. ............................. 514/183; 540/461
[58] Field of Search ...................... 540/463, 461; 514/183

[56] References Cited

FOREIGN PATENT DOCUMENTS 2042523  1/1980  United Kingdom .
9314215  7/1993  WIPO .

Primary Examiner—John M. Ford
Attorney, Agent, or Firm—Peter C. Richardson; Paul H. Ginsburg; Jolene W. Appleman

[57] ABSTRACT

A compound of the formula

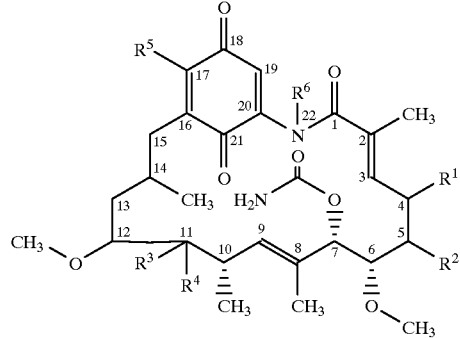

and pharmaceutically acceptable salts and prodrugs thereof wherein $R^1$, $R^2$, $R^3$, $R^4$, $R^5$ and $R^6$ are as defined below, methods and intermediates useful in the preparation thereof, pharmaceutical compositions thereof and methods of treatment therewith. The compounds of the above formula are useful in inhibiting oncogene products and as antitumor and anticancer agents.

7 Claims, No Drawings

ANSAMYCIN DERIVATIVES AS ANTIONCOGENE AND ANTICANCER AGENTS

BACKGROUND OF THE INVENTION

This invention relates to derivatives of geldanamycin, pharmaceutically acceptable salts and prodrugs of said derivatives, processes for Their preparation and antitumor and oncogene product inhibiting compositions containing said derivatives, salts and prodrugs as the active ingredients.

Oncogene products are proteins generated by cancer genes and are involved in the transformation of normal cells into cancer cells.

Geldanamycin is an antibiotic whose preparation and users were described in U.S. Pat. No. 3,595,955 (incorporated herein by reference).

Co-pending U.S. Patent application Ser. No. 07/817,235, filed Jan. 6, 1992 and assigned to Pfizer Inc. describes fermentation processes for preparing 4,5-dihydrogeldanamycin and its 18,21-hydroquinone.

Other derivatives of geldanamycin, and their use as antitumor agents are described in U.S. Pat. No. 4,261,989.

SUMMARY OF THE INVENTION

The present invention relates to compounds of the formula

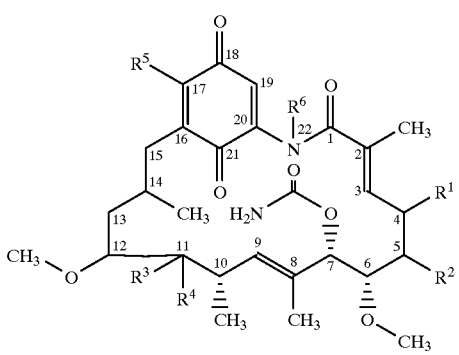

I and pharmaceutically acceptable salts and prodrugs thereof here nafter, also, referred to as the active compounds; wherein $R^1$ and $R^2$ are both hydrogen or $R^1$ and $R^2$ together form a single bond; to as the active compounds;
wherein $R^1$ and $R^2$ are both hydrogen or $R^1$ and $R^2$ together form a single bond;

$R^3$ is hydrogen and $R^4$ is selected from the group consisting of —$OR^{10}$, —$NHR^8$ and halo;

wherein $R^{10}$ is selected from the group consisting of hydrogen, $R^{11}C(=O)—$, $R^{11}SO_2—$ and $R^{12}R^{13}NSO_2NHC(=O)—$;

wherein $R^{11}$ is selected from the group consisting of amino, $(C_1-C_8)$alkyl, amino$(C_1-C_8)$alkyl, hydroxy$(C_1-C_8)$alkyl, protected amino$(C_1-C_8)$alkyl, protected hydroxy$(C_1-C_8)$alkyl, phenyl and naphthyl; and $R^{12}$ and $R^{13}$ are each independently selected from the group consisting of hydyrogen, $(C_1-C_8)$alkyl, amino $(C_1-C_8)$alkyl, dimethylamino$(C_1-C_8)$alkyl, cyclo$(C_3-C_8)$ alkyl, phenyl and naphthyl; or $R^{12}$ and $R^{13}$ together with the nitrogen to which they are attached form a heterocyclic residue selected from the group consisting of aziridinyl, azetidinyl, pyrrolidinyl, piperidinyl, thiazolidinyl, oxazolidinyl, morpholino, piperazinyl, 4-$(C_1-C_4)$ alkylpiperidinyl and N-$(C_1-C_4)$piperazinyl;

and said alkyl, phenyl and naphthyl groups may be substituted with one or more residues selected from the group consisting of $(C_1-C_8)$alkyl, halo, nitro, amino, azido and $(C_1-C_8)$alkoxyl;

or $R^3$ and $R^4$ together form a group of the formula $$=J$$

wherein J is selected from O and NOH;

$R^5$ is $NR^8R^9$ wherein $R^8$ and $R^9$ are each independently selected from the group consisting of hydrogen, $(C_1-C_8)$ alkyl, $(C_3-C_8)$cycloalkyl, $(C_2-C_8)$alkenyl and $(C_2-C_8)$ alkynyl; wherein said alkyl, alkenyl and alkynyl are optionally substituted wherein said substituents are selected from the group consisting of halo, cyano, mercapto, $(C_1-C_8)$ alkylthio, optionally substituted amino, hydroxyl, $(C_1-C_8)$ alkoxyfl, carboxyl, amidino, acylamino, and $(C_2-C_6)$ heterocycloalkyl and $(C_2-C_6)$heterocycloaryl groups selected from the group comprising imidizaloly, furyl, tetrahydrofuryl; and if comprising more than two carbon atoms may be branched, cyclic or unbranched or combinations of branched, cyclic and unbranched groups; or $R^8$ and $R^9$ together with the nitrogen to which they are attached form a heterocyclic residue selected from the group consisting of aziridinyl, azetidinyl and pyrrolidinyl;

or $R^5$ is $R^{14}O$ wherein $R^{14}$ is hydrogen or $(C_1-C_4)$alkyl;
and $R^6$ is hydrogen or a group of the formula

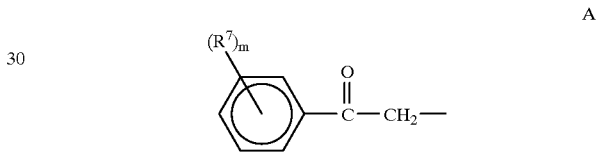

A wherein m is 0 or an integer from 1–5 and each $R^7$ is independently selected from halo, azido, nitro, $(C_1-C_8)$ alkyl, $C_1-C_8$alkoxyl, phenyl and naphthyl, cyano and $NR^8R^9$ wherein $R^6$ and $R^9$ are as defined above; with the proviso that when $R^1$ arid $R^2$ together form a single bond $R^3$ is hydrogen and $R^4$ is $OR^{10}$ wherein $R^{10}$ is hydrogen then $R^5$ cannot be $OR^{14}$, wherein $R^{14}$ is hydrogen or methyl, or $NR^8R^9$ wherein $HNR^8R^9$ is selected from the group consisting of ammonia, methylamine, ethylamine, propylamine, butylamine, pentylamine, hexylamine, heptylamine, octylamine, allylamine, β-hydroxyethylamine, β-chloroethylamine, β-glycoxyethylamine, aminobutylamine, adamantylmethylamine, cyclopropylamine, cyclopentylamine, cyclohexylamine, cycloheptylamine, cyclooctylamine, benzylamine, phenethylamine, ethyleneamine, pyrrolidine, piperidine, dimethylamine, aminoethylamine, diglycolamine, β-morpholinoethylamine, β-piperidinoethylamine, picolylamine, β-pyrrolidinoethylamine, β-pyridinylethylamine, β-methoxyethylamine, and β-N-methylaminoethylamine; and when $R^5$ is $OR^{14}$ and $R^{10}$ is $R^{11}C(=O)$, $R^{11}$ cannot be methyl.

Preferably, the compounds of the invention are compounds of formula I wherein

1. $R^1$ and $R^2$ are each hydrogen;
   a. $R^3$ and $R^6$ are each hydrogen and $R^4$ is fluoro or $OR^{10}$ wherein $R^{10}$ is selected from hydrogen, $R^{11}C(=O)—$ and $R^{12}R^{13}NSO_2NHC(O)—$ wherein $R^{11}$ is selected from amino, $(C_1-C_8)$alkyl, amino$(C_1-C_8)$alkyl, protected amino$(C_1-C_8)$alkyl phenyl and naphthyl; and $R^{12}$ and $R^{13}$ are each independently selected from the group consisting of hydrogen, $(C_1-C_8)$alkyl, amino ($C_1$–$C_8$)alkyl, dimethylamino($C_1$–$C_8$)alkyl, cyclo ($C_3$–$C_8$)alkyl, phenyl and naphthyl; or $R^{12}$ and $R^{13}$ together with the nitrogen to which they are attached form a heterocyclic residue selected from the group consisting of aziridinyl, azetidinyl, pyrrolidonyl, piperidinyl, thiazolidinyl, oxazolidinyl, morpholino, piperazinyl, 4-($C_1$–$C_4$)alkylpiperidinyl, N-($C_1$–$C_4$) piperazinyl; wherein is as defined above; and $R^5$ is $OR^{14}$ or $NR^8R^9$ wherein i. when $R^5$ is $R^8R^9N$, $R^8$ is hydrogen and $R^9$ is selected from the group consisting of ($C_1$–$C_8$)alkyl, ($C_3$–$C_8$) cycloalkyl, ($C_2$–$C_8$)alkerlyl and ($C_2$–$C_8$)alkynyl; wherein said alkyl, alkenyl and alkynyl are optionally substituted wherein said substituents are selected from the group consisting of halo, cyfano, mercapto, ($C_1$–$C_8$)alkylthio, optionally substituted amino, hydroxyl, ($C_1$–$C_8$)alkoxyl, carboxyl, amidino, acylamino, ($C_2$–$C_6$)heterocycloalkyl and ($C_2$–$C_6$)heterocycloaryl and if comprising more than two carbon atoms may be branched, cyclic or unbranchecl or combinations of branched, cyclic and unbranched groups;

ii. when $R^5$ is $R^8R^9N$, $R^8$ and $R^9$ together with the nitrogen to which they are attached form a heterocyclic residue selected from the group consisting of optionally substituted aziridinyl, azetidinyl and pyrrolidinyl wherein said substituents are selected from the group consisting of halo, cyano, mercapto, ($C_1$–$C_8$)alkylthio, substituted or unsubstituted amino, hydroxyl, ($C_1$–$C_8$)alkoxyl, ccarboxyl, amidino and acylamino;

and iii. when $R^5$ is $R^{14}O$, $R^{14}$ is hydrogen or ($C_1$–$C_6$) alkyl; with the proviso that when $R^3$ and $R^6$ are hydrogen and $R^4$ is $OR^{10}$ wherein $R^{10}$ is hydrogen, $R^{14}$ is not methyl; or b. $R^3$ is hydrogen and $R^4$ is selected from the group consisting of fluoro and $OR^{10}$ wherein $R^{10}$ is selected from hydrogen, $R^{11}C(=O)$— and $R^{12}R^{13}NSO_2NHC(O)$— wherein $R^{11}$ is selected from amino, ($C_1$–$C_8$) alkyl, amino($C_1$–$C_8$)alkyl, protected amino($C_1$–$C_8$) alkyl, phenyl and naphthyl; and $R^{12}$ and $R^{13}$ are each independently selected from the group consisting of hydrogen, ($C_1$–$C_8$)alkyl, amino($C_1$–$C_8$)alkyl, dimethylamino($C_1$–$C_8$)alkyl, cyclo($C_3$–$C_8$)alkyl, phenyl and naphthyl; or $R^{12}$ and $R^{13}$ together with the nitrogen to which they are attached form a heterocyclic residue selected from the group consisting of aziridinyl, azetidinyl, pyirolidinyl, piperidinyl, thiazolidinyl, oxazolidinyl, morpholino, piperazinyl, 4-($C_1$–$C_4$) alkylpiperidinyl, N-($C_1$–$C_4$)piperazinyl; $R^6$ is a group of the formula A wherein m is defined as above and $R^5$ is $OR^{14}$ or $NR^8R^9$ wherein i. when $R^5$ is $R^8R^9N$, $R^8$ is hydrogen and $R^9$ is selected from the group consisting of ($C_1$–$C_8$)alkyl, ($C_3$–$C_8$) cycloalkyl, ($C_2$–$C_8$)alkenyl and ($C_2$–$C_8$)alkynyl; wherein said alkyl, alkenyl and alkynyl are optionally substituted wherein said substituents are selected from the group consisting of halo, cyano, mercapto, ($C_1$–$C_8$)alkylthio, optionally substituted amino, hydroxyl, ($C_1$–$C_8$)alkoxil, carboxyl, amidino, acylamino, ($C_2$–$C_6$)heterocycloalkyl and ($C_2$–$C_6$) heterocycloaryl and if comprising more than two carbon atoms may be branched, cyclic or unbranched or combinations of branched, cyclic and unbranched groups;

ii. when $R^5$ is $R^8R^9N$, $R^8$ and $R^9$ together with the nitrogen to which they are attached form a heterocyclic residue selected from the group consisting of optionally substituted aziridinyl, azetidinyl and pyrrolidinyl wherein said substituents are selected from the group consisting of halo, cyano, mercapto, ($C_1$–$C_8$)alkylthio, substituted or unsubstituted amino, hydroxyl, ($C_1$–$C_8$)alkoxyl, cairboxyl, amidino and acylamino;

and iii. when $R^5$ is $R^{14}O$, $R^{14}$ is hydrogen or ($C_1$–$C_8$) alkyl; or c. $R^6$ is hydrogen, $R^3$ and $R^4$ together form a group of the formula $$=J$$

wherein J is O or NOH; and $R^5$ is $OR^{14}$ or $R^8R^9N$ wherein i. when $R^5$ is $R^8R^9N$, $R^8$ is hydrogen and $R^9$ is selected from the group consisting of ($C_1$–$C_8$)alkyl, ($C_3$–$C_8$) cycloalkyl, ($C_2$–$C_8$)alkenyl and ($C_2$–$C_8$)alkynyl; wherein said alkyl, alkenyl and alkynyl are optionally substituted wherein said substituents are selected from the group consisting of halo, cyano, mercapto, ($C_1$–$C_8$)alkylthio, optionally substituted amino, hydroxyl, ($C_1$–$C_8$)alkoxyl, carboxyl, amidino, acylamino, ($C_2$–$C_6$)heterocycloalkyl and ($C_2$–$C_6$)heterocycloaryl arid if comprising more than two carbon atoms may be branched, cyclic or unbranched or combinations of branched, cyclic and unbranched groups; or $R^8$ and $R^9$ together with the nitrogen to which they are attached form a heterocyclic residue selected from the group consisting of aziridinyl, azetidinyl and pyrrolidinyl;

ii. when $R^5$ is $R^8R^9N$, $R^8$ and $R^9$ together with the nitrogen to which they are attached form a heterocyclic residue selected from the group consisting of optionally substituted aziridinyl, azetidinyl and pyrrolidinyl wherein said substituents are selected from the group consisting of halo, cyano, mercapto, ($C_1$–$C_8$)alkylthio, substituted or unsubstituted amino, hydroxyl, ($C_1$–$C_8$)alkoxyl, cairboxyl, amidino and acylamino;

and iii. when $R^5$ is $R^{14}O$, $R^{14}$ is hydrogen or ($C_1$–$C_8$) alkyl; or d. $R^3$ and $R^4$ together form a group of the fomula $$=J$$

wherein J is O or NOH;

$R^6$ is a group of the formula A wherein m and $R^7$ are as defined above; and $R^5$ is $R^{14}O$ or $R^8R^9N$ wherein i. when $R^5$ is $R^8R^9N$, $R^8$ is hydrogen and $R^9$ is selected from the group consisting of ($C_1$–$C_8$)alkyl, ($C_3$–$C_8$) cycloalkyl, ($C_2$–$C_8$)alkeyl and ($C_2$–$C_8$)alkynyl; wherein said alkyl, alkenyl and alkynyl are optionally substituted wherein said substituents are selected from the group consisting of halo, cyano, mercapto, ($C_1$–$C_8$)alkylthio, optionally substituted amino, hydroxyl, ($C_1$–$C_8$)alkoxyl, carboxyl, amidino, acylamino, ($C_2$–$C_6$)heterocycloalkyl and ($C_2$–$C_6$)heterocycloaryl aind if comprising more than two carbon atoms may be branched, cyclic or unbranched or combinations of branched, cyclic and unbranched groups;

ii. when $R^5$ is $R^8R^9N$, $R^8$ and $R^9$ together with the nitrogen to which they are attached form a heterocyclic residue selected from the group consisting of optionally substituted aziridinyl, azetidinyl and pyrrolidinyl wherein said substituents are selected from the group consisting of halo, cyano, mercapto, ($C_1$–$C_8$)alkylthio, substituted or unsubstituted amino, hydroxyl, ($C_1$–$C_8$)alkoxyl, carboxyl, amidino and acylamino;

and iii. when $R^5$ is $R^{14}O$, $R^{14}$ is hydrogen or ($C_1$–$C_8$) alkyl; or 2. $R^1$ and $R^2$ together form a single bond and
   a. $R^3$ and $R^6$ are each hydrogen, $R^4$ is selected from the group consisting of fluoro and $OR^{10}$ wherein $R^{10}$ is selected from hydrogen, $R^{11}(C=O)$— and $R^{12}R^{13}NSO_2NHC(O)$— wherein $R^{11}$is selected from amino, ($C_1$–$C_8$)alkyl, amino($C_1$–$C_8$)alkyl, protected amino($C_1$–$C_8$)alkyl, phenyl and naphthyl; and $R^{12}$ and $R^{13}$ are each independently selected from the group consisting of hydrogen, ($C_1$–$C_8$)alkyl, amino($C_1$–$C_8$) alkyl, dimethylamino($C_1$–$C_8$)alkyl, cyclo($C_3$–$C_8$)alkyl, phenyl andi naphthyl; or $R^{12}$ and $R^{13}$ together with the nitrogen to which they are attached form a heterocyclic residue selected from the group consisting of aziridinyl, azetidinyl, pyrrolidinyl, piperidinyl, thiazolidinyl, oxazolidinyl, morpholino, piperazinyl, 4-($C_1$–$C_4$) alkylpiperidinyl, N-($C_1$–$C_4$)piperazinyl; and $R^5$ is $OR^{14}$ or $NR^8R^9$ wherein
      i. when $R^5$ is $R^8R^9N$, $R^8$ is hydrogen and $R^9$ is selected from the group consisting of ($C_1$–$C_8$)alkyl, ($C_3$–$C_8$) cycloalkyl, ($C_2$–$C_8$)alkeiiyl and ($C_2$–$C_8$)alkynyl; wherein said alkyl, alkenyl and alkynyl are optionally substituted wherein said substituents are selected from the group consisting of halo, cyano, mercapto, ($C_1$–$C_8$)alkylthio, optionally substituted amino, hydroxyl, ($C_1$–$C_8$)alkoxyl, carboxyl, amidino, acylamino, ($C_2$–$C_6$)heterocycloalkyl and ($C_2$–$C_6$)heterocycloaryl and if comprising more than two carbon atoms may be branched, cyclic or unbranched or combinations of branched, cyclic and unbranched groups;
      ii. when $R^5$ is $R^8R^9N$, $R^8$ and $R^9$ together with the nitrogen to which they are attached form a heterocyclic residue selected from the group consisting of optionally substituted aziridinyl, azetidinyl and pyrrolidinyl wherein said substituents are selected from the group consisting of halo, cyano, mercipto, ($C_1$–$C_8$)alkylthio, optionally substituted amino, hydroxyl, ($C_1$–$C_8$)alkoxyl, carboxyl, arnidino and acylamino;
      and iii. when $R^5$ is $R^{14}O$, $R^{14}$ is hydrogen or ($C_1$–$C_6$) alkyl; with the proviso that when $R^{10}$ is hydrogen then $R^5$ cannot be $OR^{14}$ wherein $R^{14}$ is hydrogen or methyl or $NR^8R^9$ wherein $HNR^8R^9$ is selected from the group consisting of ammonia, methylamine, ethylamine, propylamine, butylamine, pentylamine, hexylamine, heptylamine, octylamine, allylamine, β-hydroxyethylamine, β-chloroethylamine, β-glycoxyethylamine, aminobutylamine, adamantylmethylamine, cyclopropylamine, cyclopentylamine, cyclohexylamine, cycloheptylamine, cyclooctyiamine, benzylamine, phenethylamine, ethyleneamine, pyrrolidine, piperidinyl, dimethylamine, aminoethylamine, diglycoamine, β-morpholinonethylamine, β-piperidinoethylamine, picolylamine, β-pyrrolidinoethylamine, β-pyridinylethylamine, β-methoxyethylamine, and β-N-methylaminoethylamine; or
   b. $R^3$ is hydrogen and $R^4$ is selected from the group consisting of fluoro and $OR^{10}$ wherein $R^{10}$ is selected from hydrogen, $R^{11}C(=O)$— and $R^{12}R^{13}NSO_2NHC(O)$— wherein $R^{11}$is selected from amino, ($C_1$–$C_8$) alkyl, amino($C_1$–$C_8$)alkyl, protected amino($C_1$–$C_8$) alkyl, phenyl and naphthyl; and $R^{12}$ and $R^{13}$ are each independently selected from the group consisting of hydrogen, ($C_1$–$C_8$)alkyl, amino($C_1$–$C_8$)alkyl, dimethylamino($C_1$–$C_8$)alkyl, cyclo($C_3$–$C_8$)alkyl, phenyl and naphthyl; or $R^{12}$ and $R^{13}$ together with the nitrogen to which they are attached form a heterocyclic residue selected from the group consisting of aziridinyl, azetidinyl, pyrrolidinyl, piperidinyl, thiazolidinyl, oxazolidinyl, morpholino, piperazinyl, 4-($C_1$–$C_4$) alkylpiperidinyl, N-($C_1$–$C_4$)piperazinyl; $R^6$ is a group of the formula A wherein m is defined as above and $R^5$ is $OR^{14}$ or $NR^8R^9$ wherein
      i. when $R^5$ is $R^8R^9N$, $R^8$ is hydrogen and $R^9$ is selected from the group consisting of ($C_1$–$C_8$)alkyl, ($C_3$–$C_8$) cycloalkyl, ($C_2$–$C_8$)alkenyl and ($C_2$–$C_8$)alkynyl; wherein said alkyl, alkenyl and alkynyl are optionally substituted wherein said substituents are selected from the group consisting of halo, c:yano, mercapto, ($C_1$–$C_8$)alkylthio, optionally substituted amino, hydroxyl, ($C_1$–$C_8$)alkotyl, carboxyl, amidino, acylamino, ($C_2$–$C_6$)heterocycloalkyl and ($C_2$–$C_6$) heterocycloaryl and if comprising more than two carbon atoms may be branched, cyclic or unbranched or combinations of branched, cyclic and unbranched groups;
      ii. when $R^5$ is $R^8R^9N$, $R^8$ and $R^9$ together with the nitrogen to which they are attached form a heterocyclic residue selected from the group consisting of optionally substituted aziridinyl, azetidinyl and pyrrolidinyl wherein said substituents are selected from the group consisting of halo, cyano, mercapto, ($C_1$–$C_8$)alkylthio, substituted or unsubstituted amino, hydroxyl, ($C_1$–$C_8$)alkoxyl, carboxyl, amidino and acylamino;
      and iii. when $R^5$ is $R^{14}O$, $R^{14}$ is hydrogen or ($C_1$–$C_8$) alkyl; or
   c. $R^6$ is hydrogen, $R^3$ and $R^4$ together form a group of the formula $$=J$$

wherein J is O or NOH; and $R^5$ is $OR^{14}$ or $NR^8R^9$ wherein
      i. when $R^5$ is $R^8R^9N$, $R^8$ is hydrogen arid $R^9$ is selected from the group consisting of ($C_1$–$C_8$)alkyl, ($C_3$–$C_8$) cycloalkyl, ($C_2$–$C_8$)alkenyl and ($C_2$–$C_6$)alkynyl; wherein said alkyl, alkenyl and alkynyl are optionally subslituted wherein said substituents are selected from the group consisting of halo, cyano, mercapto, ($C_1$–$C_8$)alkylthio, optionally substituted amino, hydroxyl, ($C_1$–$C_9$)alkoxyl, carboxyl, amidino, acylamino, ($C_2$–$C_6$)heterocycloalkyl and ($C_2$–$C_6$)heterocycloaryl and if comprising more than two carbon atoms may be branched, cyclic or unbranched or combinations of branched, cyclic and unbranched groups;
      ii. when $R^5$ is $R^8R^9N$, $R^8$ and $R^9$ together with the nitrogen to which they are attached form a heterocyclic residue selected from the group consisting of optionally substituted aziridinyl, azetidinyl and pyrrolidinyl wherein said substituents are selected from the group consisting of halo, cyano, mercapto, ($C_1$–$C_8$)alkylthio, substituted or unsubstituted amino, hydroxyl, ($C_1$–$C_8$)alkoxyl, carboxyl, amidino and acylamino;
      and iii. when $R^5$ is $R^{14}O$, $R^{14}$ is hydrogen or ($C_1$–$C_8$) alkyl; or
   d. $R^3$ and $R^4$ together form a group of the formula =O or =NOH; $R^6$ is a group of the formula A wherein m and $R^7$ are defined as above; and $R^5$ is $R^{14}O$ or $R^8R^9N$ wherein i. when $R^5$ is $R^8R^9N$, $R^8$ is hydrogen and $R^9$ is selected from the group consisting of $(C_1-C_8)$alkyl, $(C_3-C_8)$ cycloalkyl, $(C_2-C_8)$alkenyl and $(C_2-C_8)$alkynyl; wherein said alkyl, alkenyl and alkynyl are optionally substituted wherein said substituents are selected from the group consisting of halo, cyano, mercapto, $(C_1-C_8)$alkylthio, optionally substituted amino, hydroxyl, $(C_1-C_8)$alkoxyl, carboxyl, amidino, acylamino, $(C_2-C_6)$heterocycloalkyl and $(C_2-C_6)$heterocycloaryl and if comprising more than two carbon atoms may be branched, cyclic or unbranched or combinations of branched, cyclic and unbranched groups;

ii. when $R^5$ is $R^8R^9N$, $R^8$ and $R^9$ together with the nitrogen to which they are attached form a heterocyclic residue selected from the group consisting of optionally substituted aziridinyl, azetidinyl and pyrrolidinyl wherein said substituents are selected from the group consisting of halo, cyano, mercapto, $(C_1-C_8)$alkylthio, substituted or unsubstituted amino, hydroxyl, $(C_1-C_8)$alkoxyl, carboxyl, amidino and acylamino;

and iii. when $R^5$ is $R^{14}O$, $R^{14}$ is hydrogen or $(C_1-C_8)$ alkyl.

More preferred compounds of the invention are selected from the group consisting of compounds of the formula I wherein 1. $R^1$, $R^2$, $R^3$ and $R^6$ are each hydrogen, $R^4$ is fluoro or $OR^{10}$ wherein $R^{10}$ is selected from hydrogen, $R^{11}C(=O)$— and $R^{12}R^{13}NSO_2NHC(O)$— wherein $R^{11}$ is selected from amino, $(C_1-C_8)$alkyl, amino$(C_1-C_8)$alkyl, protected amino$(C_1-C_8)$alkyl, phenyl and naphthyl; and $R^{12}$ and $R^{13}$ are each independently selected from the group consisting of hydrogen, $(C_1-C_8)$alkyl, amino$(C_1-C_8)$alkyl, dimethylamino$(C_1-C_8)$alkyl, cyclo$(C_3-C_8)$alkyl, phenyl and naphthyl; wherein is as defined above; or $R^{12}$ and $R^{13}$ together with the nitrogen to which they are attached form a heterocyclic residue selected from the group consisting of aziridinyl, azetidinyl, pyrrolidinyl, piperidinyl, thiazolidinyl, oxazolidinyl, morpholino, piperazinyl, 4-$(C_1-C_4)$alkylpiperidinyl, and N-$(C_1-C_4)$piperazinyl; and $R^5$ is $R^8R^9N$ wherein $R^8$ is hydrogen and $R^9$ is selected from hydrogen, $(C_1-C_6)$alkyl, $(C_2-C_8)$alkenyl and $(C_2-C_8)$ alkynyl; wherein said alkyl, alkenyl and alkynyl groups are optionally substituted and said substituents are selected from the group consisting of halo, cyano, mercapto, $(C_1-C_8)$ alkylthio, optionally substituted amino, hydroxyl, $(C_1-C_8)$ alkoxyl, carboxyl, amidino, acylamino, $(C_2-C_6)$ heterocycloalkyl and $(C_2-C_6)$heterocycloaryl and if comprising more than two carbon atc)ms may be branched, cyclic or unbranched or combinations of branched, cyclic and unbranched groups;

2. $R^1$, $R^2$, $R^3$ and $R^6$ are each hydrogen, $R^4$ is fluoro or —$OR^{10}$ wherein $R^{10}$ is selected from hydrogen, $R^{11}C(=O)$— and $R^{12}R^{13}NSO_2NHC(O)$— wherein $R^{11}$ is selected from amino, $(C_1-C_8)$alkyl, amino$(C_1-C_8)$alkyl, protected amino$(C_1-C_8)$alkyl, phenyl and naphthyl; and $R^{12}$ and $R^{13}$ are each independently selected from the group consisting of hydrogen, $(C_1-C_8)$alkyl, amino$(C_1-C_8)$alkyl, dimethylamino$(C_1-C_8)$alkyl, cyclo$(C_3-C_8)$alkyl, phenyl and naphthyl; wherein is as defined above; or $R^{12}$ and $R^{13}$ together with the nitrogen to which they are attached form a heterocyclic residue selected from the group consisting of aziridinyl, azetidinyl, pyrrolidinyl, piperidinyl, thiazolidinyl, oxazolidinyl, morpholino, piperazinyl, 4-$(C_1-C_4)$alkylpiperidinyl, N-$(C_1-C_4)$piperazinyl; and $R^5$ is $R^8R^9N$ wherein $R^8$ and $R^9$ together with the nitrogen to which they are attached form a 3 to 6 membered heterocycloalkyl or heterocycloaryl ring which is optionally substituted with one or more groups selected from hydroxyl, halo, cyano, $(C_1-C_6)$alkoxyl, $(C_1-C_6)$alkylthio, $(C_2-C_6)$ heterocycloalkyl and $(C_2-C_6)$ heterocycloaryl;

3. $R^1$, $R^2$, $R^3$ and $R^6$ are each hydrogen, $R^4$ is fluoro or $OR^{10}$ wherein $R^{10}$ is selected from hydrogen, $R^{11}C(=O)$— and $R^{12}R^{13}NSO_2NHC(O)$— wherein $R^{11}$ is selected from amino, $(C_1-C_8)$alkyl, amino$(C_1-C_8)$alkyl, protected amino $(C_1-C_8)$alkyl, phenyl and naphthyl; and $R^{12}$ and $R^{13}$ are each independently selected from the group consisting of hydrogen, $(C_1-C_8)$alkyl, amino$(C_1-C_8)$alkyl, dimethylamino$(C_1-C_8)$alkyl, cyclo$(C_3-C_8)$ alkyl, phenyl and naphthyl; wherein is as defined above; or $R^{12}$ and $R^{13}$ together with the nitrogen to which they are attached form a heterocyclic residue selected from the group consisting of aziridinyl, azetidinyl, pyrrolidinyl, piperidinyl, thiazolidinyl, oxazolidinyl, morpholino, piperazinyl, 4-$(C_1-C_4)$alkylpiperidinyl and N-$(C_1-C_4)$piperazinyl; and $R^5$ is $R^{14}O$ wherein $R^{14}$ is $(C_1-C_8)$alkyl with the proviso that when $R^{10}$ is hydrogen $R^{14}$ is not methyl;

4. $R^1$ and $R^2$ together form a single bond, $R^3$ and $R^6$ are each hydrogen, $R^4$ is fluoro or $OR^{10}$ wherein $R^{10}$ is selected from hydrogen, $R^{11}C(=O)$— and $R^{12}R^{13}NSO_2NHC(O)$— wherein $R^{11}$ is selected from amino, $(C_1-C_8)$alkyl, amino $(C_1-C_8)$alkyl, protected amino$(C_1-C_8)$alkyl, phenyl and naphthyl; and $R^{12}$ and $R^{13}$ are each independently selected from the group consisting of hydrogen, $(C_1-C_8)$alkyl, amino $(C_1-C_8)$alkyl, dimethylamino$(C_1-C_8)$alkyl, cyclo$(C_3-C_8)$ alkyl, phenyl and naphthyl; wherein is as defined above; or $R^{12}$ and $R^{13}$ together with the nitrogcen to which they are attached form a heterocyclic residue selected from the group consisting of aziridine, azetidine, pyrrolidone, piperidinyl, thiazolidinyl, oxazolidinyl, morpholino, piperazinyl, 4-$(C_1-C_4)$alkylpiperidinyl and N-$(C_1-C_4)$piperazinyl; and $R^5$ is $R^8R^9N$ wherein $R^8$ is hydrogen and $R^9$ is selected from hydrogen, optionally substituted $(C_1-C_6)$alkyl, optionally substituted $(C_3-C_6)$cycloalkyl, optionally substituted $(C_2-C_6)$alkenyl and optionally substituted $(C_2-C_6)$alkynyl wherein the substituents of said alkyl aind alkenyl and alkynyl groups are selected from hydroxyl, halo, cyano, $(C_1-C_6)$alkoxyl, $(C_1-C_6)$alkylthio, $(C_2-C_6)$heterocycloalkyl and $(C_2-C_6)$heterocycloaryl; with the proviso that when $R^{10}$ is hydrogen then $R^5$ cannot be $NR^8R^9$ wherein $HNR^8R^9$ is selected from the group consisting of ammonia, methylamine, ethylamine, propylamine, butylamine, pentylamine, hexylamine, heptylamine, octylamine, allylamine, β-hydroxyethylamine, β-chloroethylamine, β-glycoxyethylamine, aminobutylamine, benzyliumine, phenethylarnine, dimethylamine, aminoethylamine, diglycolamine, β-morpholinoethylamine, β-piperidinoethylamine, β-pyrrolidinoethylamine, β-pyridinylethylamine, β-methoxyethylamine, and β-N-methylaminoethylamine;

5. $R^1$ and $R^2$ together form a single bond, $R^3$ and $R^6$ are each hydrogen, $R^4$ is fluoro or $OR^{10}$ wherein $R^{10}$ is selected from hydrogen, $R^{11}C(=O)$— and $R^{12}R^{13}NSO_2NHC(O)$— wherein $R^{11}$is selected from amino, $(C_1-C_8)$alkyl, amino $(C_1-C_8)$alkyl, protected amino$(C_1-C_8)$alkyl, phenyl and naphthyl; and $R^{12}$ and $R^{13}$ are each independently selected from the group consisting of hydrogen, $(C_1-C_8)$alkyl, amino $(C_1-C_8)$alkyl, dimethylamino$(C_1-C_8)$alkyl, cyclo$(C_3-C_8)$ alkyl, phenyl and naphthyl; wherein is as defined above; or $R^{12}$ and $R^{13}$ together with the nitrogen to which they are attached form a heterocyclic residue selected from the group consisting of aziridinyl, azetidinyl, pyrrolidinyl, piperidinyl, thiazolidinyl, oxazolidinyl, morpholino, piperazinyl, 4-($C_1$-$C_4$)alkylpiperidinyl and N-($C_1$-$C_4$)piperazinyl; and $R^5$ is $R^8R^9N$ wherein $R^8$ and $R^9$ together with the nitrogen to which they are attached form a 3 to 6 membered heterocycloalkyl or heterocycloaryl ring which is optionally sLibstituted with a group selected from hydroxyl, halo, cyano, ($C_1$-$C_6$)alkoxyl, ($C_1$-$C_6$)alkylthio, ($C_3$-$C_8$)heterocycloalkyl and ($C_4$-$C_8$)heterocycloaryl; with the proviso that when $R^{10}$ is hydrogen then $NR^8R^9$ cannot be derived from ethyleneamine, pyrrolidine or piperidine;

6. $R^1$ and $R^2$ together form a single bond, $R^3$ and $R^6$ are each hydrogen, $R^4$ is fluoro or $OR^{10}$ wherein $R^{10}$ is selected from hydrcgen, $R^{11}C(=O)$— and $R^{12}R^{13}NSO_2NHC(O)$— wherein $R^{11}$ is selected from amino, ($C_1$-$C_8$)alkyl, amino ($C_1$-$C_8$)alkyl, protected amino($C_1$-$C_8$)alkyl, phenyl and naphthyl; and $R^{12}$ and $R^{13}$ are each independently selected from the group consisting of hydrogen, ($C_1$-$C_8$)alkyl, amino ($C_1$-$C_8$)alkyl, dimethylamino($C_1$-$C_8$)alkyl, cyclo($C_3$-$C_8$) alkyl, phenyl aind naphthyl; wherein is as defined above; or $R^{12}$ and $R^{13}$ together with the nitrogen to which they are attached form a heterocylic residue selected from the group consisting of aziridinyl, azetidinyl, pyrrolidinyl, piperidinyl, thiazolidinyl, oxazolidinyl, morpholino, piperazinyl, 4-($C_1$-$C_4$)alkylpiperidinyl and N-($C_1$-$C_4$)piperazinyl; and $R^5$ is $R^{14}O$ wherein $R^{14}$ is hydrogen or ($C_1$-$C_8$)alkyl; with the proviso that when $R^{10}$ is hydrogen $R^{14}$ cannot be hydrogen or methyl and when $R^{10}$ is $R^{11}C(=O)$, $R^{11}$ cannot be methyl;

7. $R^1$, $R^2$ and $R^6$ are each hydrogen, $R^3$ and are $R^4$ together form a group selected from =O and =NOH and $R^5$ is $R^8R^9N$ wherein $R^8$ is hydrogen and $R^9$ is selected from hydrogen, optionally substituted ($C_1$-$C_6$)alkyl or optionally substituted ($C_3$-$C_6$)cycloalkyl ($C_2$-$C_6$)alkenyl and ($C_2$-$C_6$)alkynyl wherein the substituents of said alkyl, alkenyl and alkynyl groups are selected from hydroxyl, halo, cyano, ($C_1$-$C_6$)alkoxyl, ($C_1$-$C_6$)alkylthio, ($C_2$-$C_6$)heterocycloalkyl and ($C_2$-$C_6$)heterocycloaryl;

8. $R^1$, $R^2$ and $R^6$ are each hydrogen, $R^3$ and $R^4$ logether form a group selected from =O and =NOH and $R^5$ is $R^8R^9N$ wherein $R^8$ ard $R^9$ together with the nitrogen to which they are attached form a 3 to 6 membered heterocycloalkyl or heterocycloaryl ring which is optionally substituted with one or more groups selected from hydroxyl, halo, cyano, ($C_1$-$C_6$)alkoxyl, ($C_1$-$C_6$)alkylthio, ($C_2$-$C_6$)heterocycloalkyl and ($C_2$-$C_6$)heterocycloaryl;

9. $R^1$, $R^2$ and $R^6$ are each hydrogen, $R^3$ and $R^4$ together form a group selected from =O and =NOH and $R^5$ is $R^{14}O$ wherein $R^{14}$ is hydrogen or ($C_1$-$C_8$)alkyl;

10. $R^1$ and $R^2$ together form a single bond, $R^6$ is hydrogen, $R^3$ and $R^4$ together form a group selected from =O and =NOH;

and $R^5$ is $R^8R^9N$ wherein $R^8$ is hydrogen and $R^9$ is selected from hydrogen, optionally substituted ($C_1$-$C_6$)alkyl or optionally substituted ($C_3$-$C_6$)cycloalkyl, ($C_2$-$C_6$)alkenyl and ($C_2$-$C_6$)alkynyl wherein the substituents of said alkyl, alkenyl and alkynyl groups are selected from hydroxyl, halo, cyano, ($C_1$-$C_6$)alkoxyl, ($C_1$-$C_6$)alkylthio, ($C_2$-$C_6$)heterocycloalkyl and ($C_2$-$C_6$)heterocycloaryl;

11. $R^1$ and $R^2$ together form a single bond, $R^6$ is hydrogen, $R^3$ and $R^4$ together form a group selected from =O and =NOH and $R^5$ is $R^8R^9N$ wherein $R^8$ and $R^9$ together with the nitrogen to which they are attached form a 3 to 6 membered heterocycloalkyl or heterocycloaryl ring which is optionally substituted with one or more groups selected from hydroxyl, halo, cyano, ($C_1$-$C_6$)alkoxyl, ($C_1$-$C_6$)alkylthio, ($C_2$-$C_6$)heterocycloalkyl and ($C_2$-$C_6$)heterocycloaryl;

12. $R^1$ and $R^2$ together form a single bond, $R^6$ is hydrogen, $R^3$ and $R^4$ together form a group selected from =O and =NOH and $R^5$ is $R^{14}O$ wherein $R^{14}$ is hydrogen or ($C_1$-$C_8$)alkyl;

13. $R^1$, $R^2$ and $R^3$ are each hydrogen, $R^6$ is a group of the formula A wherein m and $R^7$ are as defined above, $R^4$ fluoro or $OR^{10}$; wherein $R^{10}$ is selected from the group consisting of hydrogen, $R^{11}C(=O)$—, $R^{11}SO_2$— and $R^{12}R^{13}NSO_2NHC(=O)$—; wherein $R^{11}$ is selected from the group consisting of amino, ($C_1$-$C_8$)alkyl, amino($C_1$-$C_8$) alkyl, protected amino($C_1$-$C_8$)alkyl, phenyl and naphthyl; and $R^{12}$ and $R^{13}$ are each independently selected from the group consisting of hydrogen, ($C_1$-$C_8$)alkyl, amino($C_1$-$C_8$) alkyl, dimethylamino($C_1$-$C_8$)alkyl, cyclo($C_3$-$C_8$)alkyl, phenyl and naphthyl; and said alkyl, phenyl and naphthyl groups may be substituted with one or more residues selected from the group consisting of ($C_1$-$C_8$)alkyl, halo, nitro, amino, azido and ($C_1$-$C_8$)alkoxyl; and $R^5$ is $R^8R^9N$ wherein $R^8$ is hydrogen and $R^9$ is selected from hydrogen, optionally substituted ($C_1$-$C_6$)alkyl, optionally substituted ($C_3$-$C_6$) cycloalkyl, optionally substituted ($C_2$-$C_6$)alkenyl and optionally substituted ($C_2$-$C_6$)alkynyl wherein the substituents of said alkyl, alkenyl and alkynyl groups are selected from hydroxyl, halo, cyano, ($C_1$-$C_6$)alkoxyl, ($C_1$-$C_6$) alkylthio, ($C_2$-$C_6$)heterocycloalkyl and ($C_2$-$C_6$) heterocycloaryl;

14. $R^1$, $R^2$ and $R^3$ are each hydrogen, $R^6$ is a group of the formula A wherein m and $R^7$ are as defined above, $R^4$ is fluoro or $OR^{10}$; wherein $R^{10}$ is selected from the group consisting of hydrogen, $R^{11}C(=O)$—, $R^{11}SO_2$— and $R^{12}R^{13}NSO_2NHC(=O)$—; wherein $R^{11}$ is selected from the group consisting of amino, ($C_1$-$C_8$)alkiyl, amino($C_1$-$C_8$) alkyl, protected amino($C_1$-$C_8$)alkyl, phenyl and naphthyl; and $R^{12}$ and $R^{13}$ are each independently selected from the group consisting of hydrogen, ($C_1$-$C_8$)alkyl, amino($C_1$-$C_8$) alkyl, dimethylamino($C_1$-$C_8$)alkyl, cyclo($C_3$-$C_8$)alkyl, phenyl and naphthyl; and said alkyl, phenyl and naphthyl groups may be substituted with at least one residue selected from the group consisting of ($C_1$-$C_8$)alkyl, halo, nitro, amino, azid, and ($C_1$-$C_8$)alkoxyl; and $R^5$ is $R^8R^9N$ wherein $R^3$ and $R^9$ together with the nitrogen to which they are attached form a 3 to 6 membered heterocycloalkyl or heterocycloaryl ring which is optionally substituted with at least one group selected from hydroxyl, halo, cyano, ($C_1$-$C_6$)alkoxyl, ($C_1$-$C_6$)alkylthio, ($C_2$-$C_6$)heterocycloalkyl and ($C_2$-$C_6$) heterocycloaryl;

15. $R^1$, $R^2$ and $R^3$ are each hydrogen, $R^6$ is a group of the formula A wherein m and $R^7$ are as defined above, $R^4$ is $OR^{10}$ or fluoro; wherein $R^{10}$ is selected from the group consisting of hydrogen, $R^{11}C(=O)$—, $R^{11}SO_2$— and $R^{12}R^{13}NSO_2NHC(=O)$—; wherein $R^{11}$ is selected from the group consisting of amino, ($C_1$-$C_8$)allkyl, amino($C_1$-$C_8$) alkyl, protected amino($C_3$-$C_6$)alkyl, phenyl and naphthyl; $R^{12}$ and $R^{13}$ are each independently selected from the group consisting of hydrogen, ($C_1$-$C_8$)alkyl, amino($C_1$-$C_8$)alkyl, dimethylamino($C_1$-$C_8$)alkyl, cyclo($C_3$-$C_8$)alkyl, morpholino, N-methylpiperazinyl, phenyl and naphthyl; and said alkyl, phenyl and naphthyl groups may be substituted with one or more residues selected from the group consisting of $(C_1-C_8)$alkyl, halo, nitro, amino, azido and $(C_1-C_8)$alkoxyl; and $R^5$ is $R^{14}O$ wherein $R^{14}$ is hydrogen or $(C_1-C_8)$alkyl;

16. $R^1$ and $R^2$ together form a single bond, $R^3$ is hydrogen, $R^6$ is a group of the formula A wherein m and $R^7$ are as defined above, $R^4$ is $OR^{10}$ or fluoro; wherein $R^{10}$ is selected from the group consisting of hydrogen, $R^{11}C(=O)-$, $R^{11}SO_2-$ and $R^{12}R^{13}NSO_2NHC(=O)-$; wherein $R^{11}$ is selected from the group c)nsisting of amino, $(C_1-C_8)$alkyl, amino$(C_1-C_8)$alkyl, protected amino$(C_1-C_8)$alkyl, phenyl and naphthyl; and $R^{12}$ and $R^{13}$ are each independently selected from the group consisting of hydrogen, $(C_1-C_8)$alkyl, amino$(C_1-C_8)$alkyl, dimethylamino$(C_1-C_8)$alkyl, cyclo$(C_3-C_8)$alkyl, phenyl and naphthyl and said alkyl, phenyl and naphthyl groups may be substituted with one or more substituents selected from the group consisting of $(C_1-C_8)$alkyl, halo, nitro, amino, azido and $(C_1-C_8)$alkoxyl;

and $R^5$ is $R^8R^9N$ wherein $R^8$ is hydrogen and $R^9$ is selected from hydrogen, optionally substituted $(C_1-C_6)$alkyl, optionally substituted $(C_3-C_6)$cycloalkyl, optionally substituted $(C_2-C_6)$alkenyl and optionally substituted $(C_2-C_6)$alkynyl wherein the substituents of said alkyl and alkenyl and alkynyl groups are selected from hydroxyl, halo, cyano, $(C_1-C_6)$alkoxyl, $(C_1-C_6)$alkylthio, $(C_2-C_6)$heterocycloalkyl and $(C_2-C_6)$heterocycloaryl;

17. $R^1$ and $R^2$ together form a single bond, $R^3$ is hydrogen, $R^6$ is a group of the formula A wherein m and $R^7$ are as defined above, $R^4$ is $OR^{10}$ or fluoro; wherein $R^{10}$ is selected from the group consisting of hydrogen, $R^{11}C(=O)-$, $R^{11}SO_2-$ and $R^{12}R^{13}NSO_2NHC(=O)-$; wherein $R^{11}$ is selected from the group consisting of amino, $(C_1-C_8)$alkyl, amino$(C_1-C_8)$alkyl, protected amino$(C_1-C_8)$alkyl, phenyl and naphthyl; and $R^{12}$ and $R^{13}$ are each independently selected from the group consisting of hydrogen, $(C_1-C_8)$alkyl, amino$(C_1-C_8)$alkyl, dimethylamino$(C_1-C_8)$alkyl, cyclo$(C_1-C_8)$alkyl, phenyl and naphthyl; and said alkyl, phenyl and naphthyl groups may be substituted with one or more residues selected from the group consisting of $(C_1-C_8)$alkyl, halo, nitro, amino, azido and $(C_1-C_8)$alkoxyl; and $R^5$ is $R^8R^9N$ wherein $R^8$ and $R^9$ together with the nitrogen to which they are attached form a 3 to 6 membered heterocycloalkyl or heterocycloaryl ring which is optionally substituted with at least one group selected from hydroxyl, halo, cyano, $(C_1-C_6)$alkoxyl, $(C_1-C_6)$alkylthio, $(C_2-C_6)$heterocycloalkyl and $(C_2-C_6)$heterocycloaryl;

18. $R^1$ and $R^2$ together form a single bond, $R^3$ is hydrogen, $R^6$ is a group of the formula A wherein m and $R^7$ are as defined above, $R^4$ is $OR^{10}$ or fluoro; wherein $R^{10}$ is selected from the group consisting of hydrogen, $R^{11}C(=O)-$, $R^{11}SO_2-$ and $R^{12}R^{13}NSO_2NHC(=O)-$; wherein $R^{11}$ is selected from the group consisting of amino, $(C_1-C_8)$alkyl, amino$(C_1-C_8)$alkyl, protected amino$(C_1-C_8)$alkyl, phenyl and naphthyl; and $R^{12}$ and $R^{13}$ are each independently selected from the group consisting of hydrogen, $(C_1-C_8)$alkyl, amino$(C_1-C_8)$alkyl, dimethylamino$(C_1-C_8)$alkyl, cyclo$(C_1-C_8)$alkyl, phenyl and naphthyl; and said alkyl, phenyl and naphthyl groups may be substituted with one or more residues selected from the group consisting of $(C_1-C_8)$alkyl, halo, nitro, amino, azido and $(C_1-C_8)$alkoxyl; and R is $R^{14}O$ wherein $R^{14}$ is hydrogen or $(C_1-C_8)$alkyl;

19. $R^1$ and $R^2$ are each hydrogen, $R^6$ is a group of the formula A wherein m is and $R^7$ are defined above, $R^3$ and are $R^4$ together form a group selected from $=O$ and $=NOH$ and $R^5$ is $R^8R^9N$ wherein $R^8$ is hydrogen and $R^9$ is selected from hydrogen, optionally substituted $(C_1-C_6)$alkyl, optionally substituted $(C_3-C_6)$cycloalkyl, optionally substituted $(C_2-C_6)$alkenyl and optionally substituted $(C_2-C_6)$alkynyl wherein the substituents of said alkyl, alkenyl and alkynyl groups are selected from hydroxyl, halo, cyano, $(C_1-C_6)$alkoxyl, $(C_1-C_6)$alkylthio, $(C_2-C_6)$hetcerocycloalkyl and $(C_2-C_6)$heterocycloaryl;

20. $R^1$ and $R^2$ are each hydrogen, $R^6$ is a group of the formula A wherein m and $R^7$ are as defined above, $R^3$ and $R^4$ together form a group selected from $=O$ and $=NOH$ and $R^5$ is $R^8R^9N$ wherein $R^8$ and $R^9$ together with the nitrogen to which they are attached form a 3 to 6 membered heterocycloalkyl or heterocglcloaryl ring which is optionally substituted with one or more groups selected from hydroxyl, halo, cyano, $(C_1-C_6)$alkoxyl, $(C_1-C_6)$alkylthio, $(C_2-C_6)$heterocycloalkyl and $(C_2-C_6)$heterocycloaryl;

21. $R^1$ and $R^2$ are each hydrogen, $R^6$ is a group of the formula A wherein m and $R^7$ are as defined above, $R^3$ and $R^4$ together form a group selected from $=O$ and $=NOH$ and $R^5$ is $R^{14}O$ wherein $R^{14}$ is hydrogen or $(C_1-C_8)$alkyl;

22. $R^1$ and $R^2$ together form a bond, $R^6$ is a group of the formula A wherein m and $R^7$ are as defined above, $R^3$ and $R^4$ together form a group selected from $=O$ and $=NOH$ and $R^5$ is $R^8R^9N$ wherein $R^8$ is hydrogen and $R^9$ is selected from hydrogen, optionally substituted $(C_1-C_6)$alkyl or optionally substituted $(C_3-C_6)$cycloalkyl, $(C_2-C_6)$alkenyl and $(C_2-C_6)$alkynyl wherein the substituents of said ilkyl and alkenyl and alkynyl groups are selected from hydroxyl, halo, cyano, $(C_1-C_6)$alkoxyl, $(C_1-C_6)$alkylthio, $(C_2-C_6)$heterocycloalkyl and $(C_2-C_6)$heterocycloaryl;

23. $R^1$ and $R^2$ together form a bond, $R^6$ is a group of the formula A wherein m and $R^7$ are as defined above, $R^3$ and $R^4$ together form a group ,elected from $=O$ and $=NOH$ and $R^5$ is $R^8R^9N$ wherein $R^8$ and $R^9$ together with the nitrogen to which they are attached form a 3 to 6 membered heterocycloalkyl or heterocycloaryl ring which is optionally substituted with one or more groups selected from hydroxyl, halo, cyano, $(C_1-C_6)$alkoxyl, $(C_1-C_6)$alkylthio, $(C_2-C_6)$heterocycloalkyl and $(C_2-C_6)$heterocycloaryl; or 24. $R^1$ and $R^2$ together form a bond, $R^6$ is a group of the formula A wherein m and $R^7$ are as defined above, $R^3$ and $R^4$ together form a group selected from $=O$ and $=NOH$ and $R^5$ is $R^{14}O$ wherein $R^{14}$ is hydrogen or $(C_1-C_8)$alkyl.

Most preferred compounds of the invention are selected from the group consisting of 17-Amino-4,5-dihydro-17-demethoxy-geldanamycin;

17-Methylamino-4,5-dihydro-17-demethoxygeldanamycin;

17-Cyclopropylamino-4,5-dihydro-17-demethoxygeldanarnycin;

17-(2'-Hydroxyethylamino)-4,5-dihydro-17-demethoxygelclanamycin;

17-(2-Methoxyethylamino)-4,5-dihydro-17-demethoxygeld anamycin;

17-(2'-Fluoroethylamino)-4,5-dihydro-17-demethoxygeldanamycin;
17-[s-(+)-2-Hydroxypropylamino]-4,5-dihydro-17-demethoxygeldanamycin;
17-Azetidin-1-yl-4,5-dihydro-17-demethoxygeldanamycin;
17-(3-Hydroxyazetidin-1-yl)-4,5-dihydro-17-demethoxygeldanamycin;
17-Azetidin-1-yl-4,5-dihydro-11-α-fluoro-17-demethoxygeldanamycin;
17-Azetidin-1-yl-17-demethoxygeldanamycin;
17-(2'-Cyanoethylamino)-17-demethoxygeldanamycin;
17-(2'-Fluoroethylamino)-17-demethoxygeldanamycin;
17-Amino-22-(2'-methoxyphenacyl)-17-demethoxygeldanamycin;
17-Amino-22-(3'-methoxyphenacyl)-17-demethoxygeldanetmycin;
17-Amino-22-(4'-chlorophenacyl)-17-demethoxygeldanamycin;
17-Amino-22-(3',4'-dichlorophenacyl)-17-demethoxygeldanamycin;
17-Amino-22-(4'-amino-3'-iodophenacyl)-17-demethoxygeldanamycin;
17-Amino-22-(4'-azido-3'-iodophenacyl)-17-demethoxygeldanamycin;
17-Amino-11-α-fluoro-17-demethoxygeldanamycin;
17-Allylamino-11-α-fluoro-17-demethoxygeldanamycin;
17-Propargylamino-11-α-fluoro-17-demethoxygeldanamycin;
17-(2'-Fluoroethylamino)-11-α-fluoro-17-demethoxygeldanamycin;
17-Azetidin-1-yl-11-(4'-azidophenyl)sulfamylcarbonyl-17-demethoxygeldanamycin;
17-(2'-Fluoroethylamino)-11-keto-17-demethoxygeldanamycin;
17-Azetidin-1-yl-11-keto-17-demethoxygeldanamycin; and
17-(3'-Hydroxyazetidin-1-yl)-11-keto-17-demethoxygeldanamycin.

This invention also relates to a pharmaceutical composition comprising an antitumor or oncogene product inhibiting or cancer preventing or treating effective amount of a compound of the formula I, or a pharmaceutically acceptable salt or prodrug thereof, and a pharmaceutically acceptable carrier.

This invention also relates to a method of inhibiting an oncogene product in a mammal, including a human, comprising administering to said mammal an oncogene product inhibiting effective amount of a compound of the formula I or a pharmaceutically acceptable salt or prodrug thereof.

This invention also relates to a method of inhibiting an ErbB-2, src, Ick, fyn or abl oncogene product in a mammal, including a human, comprising administering to said mammal an ErbB-2, src, Ick, fyn or abl oncogene product inhibiting effective amount of a compound of the formula I or a pharmaceutically acceptable salt or prodrug thereof.

This invention also relates to a method of treating or preventing cancer in a mammal, including a human, comprising administering to said mammal an antitumor or oncogene product inhibiting effective amount of a compournd of the formula I or a pharmaceutically acceptable salt or prodrug thereof.

This invention also relates to a method of preventing or inhibiting the growth of a tumor in a mammal, including a human, comprising administering to said mammal an antitumor effective amount of a compound of the formula I or a pharmaceutically acceptable salt or prodrug thereof.

This invention also relates to a method of inhibiting growth factors that play an important role in uncontrolled cell proliferation such as the EGF receptor, the NGF receptor, the PDGF receptor and the insulin receptor in a mammal, including a human, comprising administering to said mammal a growth factor inhibiting effective amount of a compound of the formula I or a pharmaceutically acceptable salt or prodrug thereof.

The pharmaceutically acceptable salts of the present invention are those which are non-toxic at the dosages administered. Since compounds of the invention may contain basic groups, acid addition salts are possible. Pharmaceutically acceptable acid addition salts include, for example, the hydrochloride, hydrObromide, hydroiodide, sulfate, bisulfate, phosphate, acid phosphate, acetate, lactalte, maleate, mesylate, fumarate, citrate, acid citrate, tartrate, bitartrate, succinate, gluConate and saccharate salts.

Typical pharmaceutically acceptable anions include the acetate; benzenesulfonate; benzoate; bicarbonate; bitartrate; bromide; calcium edetate; camsylate; carbonate; chloride; citrate; dihydrochloride; edetixte; edisylate; estolate; esylate; fumarate; gluceptate; gluconate; glutamate; glycollylarsNIlate; hexylresorcinate; hydroxynaphthoate; iodide; isothionate; lactate; lactobionate; malate; maleate; mandelate; mesylate; methylbromide; methyinitrate; methylsulfate; mucate; napsylate; nitrate; pamoate (embonate); pantothenate; phosphate; polygAlacturonate; salicylate; stearate; subacetate; succinate; sulfate; tannate; tartrate; and teoclate.

Unless indicated otherwise, the alkyl, alkoxy, and alkenyl moieties referred to herein may comprise linear, branched and cyclic moieties and combinations thereof and the term "halo" includes fluoro, chloro, bromo and iodo. It will be understood, however that a group comprising only 1 or 2 atoms cannot be branched or cyclic. Examples of alkyl groups are methyl, ethyl, propyl, cyclopropyl, isopropyl, butyl, t-butyl, cyclobutyl, pentyl, isopentyl, cyclopentyl, hexyl and cyclohexyl.

Furthermore, unless otherwise indicated optionally substituted means comprising from zero to the maximum number of substituents, e.g., 3 for a methyl group, 1 for a hexyl group and 5 for a phenyl group.

The active compounds of the invention may be administered orally, topically, parenterally, by inhalation spray or rectally in dosage unit formulations containing conventional non-toxic pharmaceutically acceptable carriers, adjuvants and vehicles.

The term parenteral as used herein includes subcutaneous injections, intravenous, intramuscular, intrasternal injection or infusion techniques.

DETAILED DESCRIPTION OF THE INVENTION

The following reaction schemes illustrate the preparation of the compounds of the formula I. In the reaction schemes and discussion that follow, except where otherwise indicated, $R^1$, $R^2$, $R^4$, $R^5$, $R^6$, $R^7$, $R^8$, $R^9$ and $R^{10}$ are defined as for formula I above.

SCHEME 1
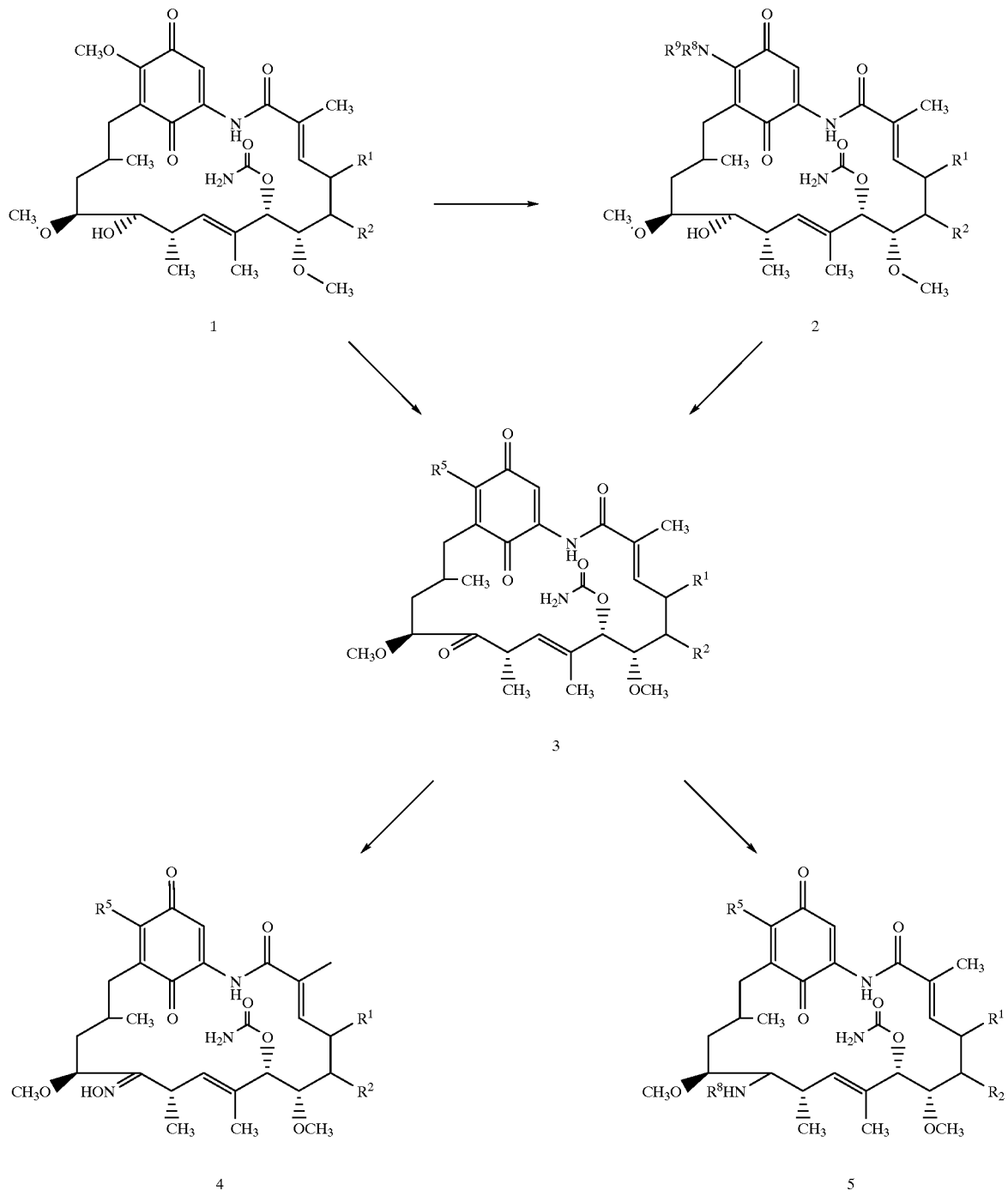

SCHEME 2

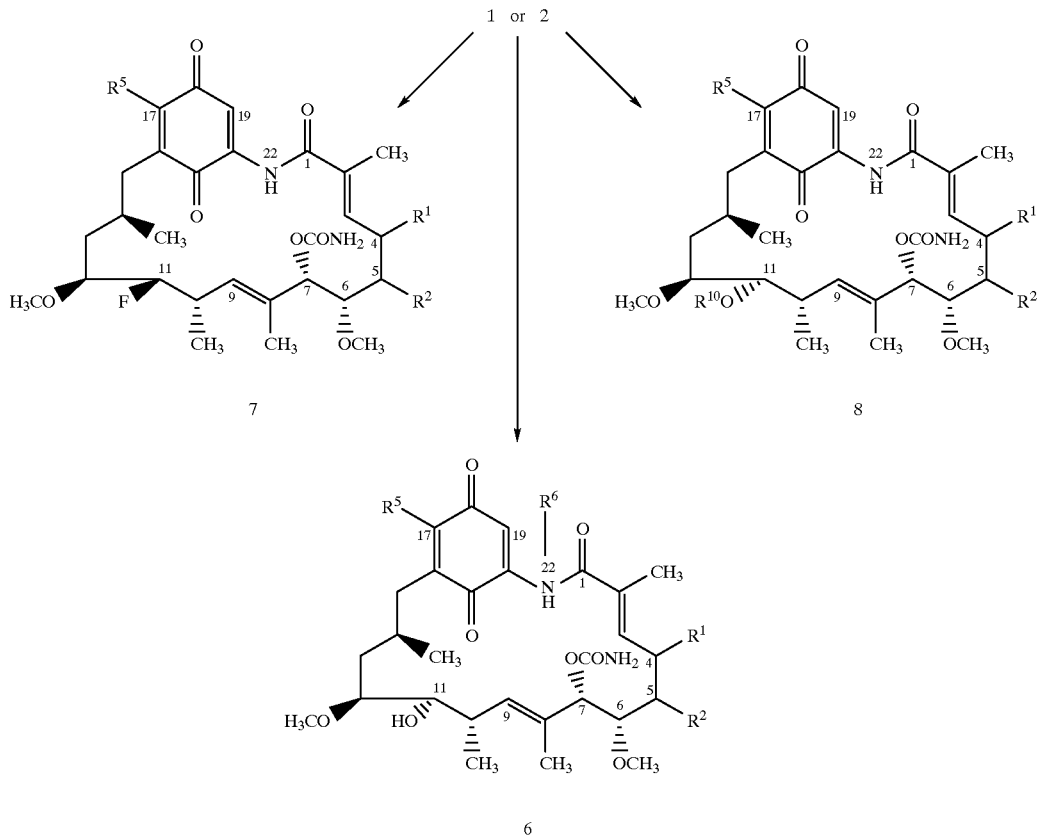

As shown in Scheme 1 compound 2 is formed by condensation of the geldanamyacin or 4,5-dihydrogeldanamyacin 1 with an amine $R^8R^9NH$. This reaction is generally carried out by mixing the amine and the ansamycin in an inert solvent such as chloroform, methylene chloride, N,N-dimethylformamide (DMF), pyridine, acetonitrile, tetrahydrofuran (THF) or a lower alcohol, preferably chloroform or methylene chloride, at a temperature from about ambient temperature to the reflux temperature of the solvent, preferably from about ambient temperature to about 65° C.

The conversion of 1 or 2 to 3 is generally carried out by oxidizing 2 with standard oxidizing reagents such as pyridinium chlorochromate in methylene chloride, pyridinium dichromate in DMF, oxalyl chloride/dimethyl sulfoxide (DMSO) in methylene chloride, Dess-Martin periodinane in chloroform, and Jones reagent in acetone, preferably Dess-Martin periodinane in chloroform at reflux. Those skilled in the art will recognize that these reagents can be used with additional, inert solvents and at temperatures ranging from −60° C. to the reflux temperature of tle solvent.

The conversion of 3 to 4 is generally carried out by reacting 3 with hydroxylamine hydrochloride in the presence of a base (e.g., sodium acetate, pyridine, sodium carbonate, sodium hydroxide, potassium carbonate, and triethylamine) in water or a lower alcohol solvent at about 0° C. to about 100° C. Prefearably, 3 is combined with hydroxylamine hydrochloride in the presence of triethylamine in ethanol at room temperature.

The conversion of 3 to 5 is generally carried out under standard reductive amination conditions such as combining the amine and 3 in an inert solvent (e.g., halogenated $(C_1–C_6)$ alkanes and $(C_1–C_6)$alcohols) with a suitable reducing agent (e.g., sodium borohydride, sodium cyanoborohydride, sodium triacetoxyborohydride and formic acid), optionally in the presence of a dehydrating agent (e.g., sodium sulfate, molecular sieves, and calcium sulfate), at temperatures ranging from about ambient temperature to the reflux temperature of the solvent. Preferably, the reaction is carried out by combining 3, the amine, sodium triacetoxyborohydride and sodium sulfate in 1,2-dichloroethane at ambient temperature.

As shown in Scheme 2 compound 1 or 2 can be selectively 22-N-alkylated to afford 6 by treatment with a base, such as a $(C_1–C_6)$ alkoxide, in a polar solvent, for instance dimethylformamide or dimethyl sulfoxide, followed by reaction with an appropriate alkylating agent, for example, an alkyl halide. Reaction temperatures are maintained between about 5 and about 65° C., optimally from abclut 5 to about 25° C. Alternatively, the compound 1 or 2 can be reacted with anhydrous p)otassium carbonate and the alkyl halide in acetone at reflux.

Compound 7 can be prepared by treating compound 1 or 2 with diethylaminosulfurtrifluoride (DAST). This reaction is performed in AN inert solvent (e.g., methylene chloride, chloroform and dichloroethane) at low temperature of about −78° to about 0° C., preferably from about −78° to about −50° C. OptiMally, the reaction is quenched at low temperature with dilute aqueous base, for example 5% sodium bicarbonate.

Compound 1 or 2 can be converted to 11-O-acyl or 11-O-sulfonyl derivatives by treatment with acylating or sulfonating agents in the presence of non-nucleophilic bases. The acylating agents include acid anhydrides, halides and isocyanates. Sulfonating agents include sulfonyl halides and anhydrides.

Solvents used in these reactions include a wide variety of aprotic polar and non-polar media, for example, acetone, chloroform, ethyl acetate, DMF, pyridine, tetrahydrofuran. Bases used include 1,8-diazabicyclo[5.4.0]undec-7-ene (DBU), triethylamine and 4-dimethylaminopyridine. If desired, compounds 3–7 wherein $R^5$ is $R^{14}O$ may be converted to compounds 3–7 wherein $R^5$ is $R^8R^9$ by the method for converting 1 to 2 in Scheme 1.

The preparation of other compounds of the formula I not s;pecifically described above can be accomplished using combinations of the above reactions that will be clear to those skilled in the art in view of the foregoing disclosure.

The compounds of formula I and their pharmaceutically acceptable salts are useful as antitumor agents (including, but not limited to anticancer agents) and oncogene product inhibitors. They are useful, for example, in inhibiting the ErbB-2, src, Ick, fyn and abL oncogene products. They are also useful in inhibiting certain growth factors that play an important role in uncontrolled cell proliferation such as the EGF receptor, the NGF receptor, the PDGF receptor and the insulin reaceptor.

The ability of the active compounds to inhibit the ErbB-2 oricogene product may be determined by the following method for determining the p185 concentrations in SKBr3 cells.

SKBr3 human breast cancer cells, obtained from the ATCC, Rockville, Md. were seeded in 8 well tissue culture plates (9.5 cm$^2$/well, Falcon, Becton Dickenson, Lincoln Park, N.J.) at 5×10$^5$ cells/well in 2 ml McCoys medium, supplemented with 10% fetal calf serum and glutamine. Cells were allowed to attach overnight at 37° C. in a 5% CO$_2$ atmosphere.

The compounds are dissolved in DMSO and tested over a range of concentrations by addition to the medium, followed by incubation at 37° C. for 6 hours. At the end of the incubation, the medium is aspirated from the well, and the cells are washed twice with 2 ml of TNK buffer (50 mM tris (hydroxymethyl)aminomethane hydrochloride, 140 mM NaCL, 3.3 mM KCL, 0.5 mM sodium orthovanadate, adjusted to pH 7.4). The cells are then lysed by addition of 250 μl boiling Lalammli sample buffer (140 mM tris (hydroxymethyl)aminomethane hydrochloric acid, pH 6.8, 5.7% sodium dodecyl sulfate, 29% glycerol) with shaking. The cell lysate is transferred to a tube and then placed in a boiling water bath for 5 mins. The lysates are then sonicated with a probe sonicator and stored at −70° C. until analysis.

The p185 concentration of each sample may be determined by standard immunoblotting procedures essentially as described by Harlow and Lane (*Antibodies: A Laboratory Manual*, Cold Spring Harbor Laboratory, 1988). A standard portion of each sample is mixed with dithiothreitol (10% added of a 1M solution), and then a portion corresponding to ~10 μg of protein is blotted onto a nitrocellulose membrane (BA-S, Schleicher and Schuell, Keene, New Hampshire) equilibrated with rinse buffer (10 mM Tris hydrochloric acid pH 7.4, 150 mM NaCL) by use of A dot blot apparatus (Mini-fold, Schleicher and Schuell, Keene, New Hampshire) with an underlayer of filter paper. The wells are rinsed with 200 μl of a rinse buffer, blocked by incubation with a blocking buffer (5% bovine serum albumin, 1% ovalbumin in rinse buffer), and then incubated for 4 to 12 hours with a 1:1000 dilution of NT1, an eLffinity purified rabbit polyclonal antibody raised by standard methods (Harlow and Lane, *Antibodies, A Laboratorv Manual*, Cold Spring Harbor Laboratory, 1988) against a peptide representing the C-terminal domain of human p185 (sequence, TAENPEYLGLDVPV, by the standard 1 letter amino acid code). The membrane is then rinsed twice for 10 minutes with rinse buffer and once for 10 minutes in rinse buffer with 0.05% Triton X-100, and then twice more for 10 minutes in rinse buffer. The membrane is then incubated with a 1:3000 dilution of horseradish peroxidase labeled donkey anti-rabbit antibody (Amersham, Arlington Heights, Ill.) in a rinse buffer with shaking for 20–45 minutes. The membrane is then again rinsed twice for 10 minutes in the rinse buffer, once for 10 minutes in the rinse buffer with 0.05% Triton X-100, And then twice more for 10 minutes in the rinse buffer. The p185 is then visualized with the ECL Detection Kit (Amersham, Arlington Heights, Ill.) and recorded with Hyperiilm-ECL (Amersham, Arlington Heights, Ill.). The p185 is then estimated by densitometric analysis of the film. IC$_{50}$ values are determined by reference to the p185 contert of samples of cells exposed only to vehicle (DMSO) and measured as described.

The ability of the active compounds to inhibit the ErbB-2 oncogene product may be determined by following the method of Kamps et al., *Oncogene*, 2, 305–315 (1988) for determining the phosphorylation of p185 in SKBR3 and other ErbB-2 transformed cell lines.

The ability of the active compounds to inhibit the growth of certain human carcinoma cells may be determined by the methods of Alley et al., *Cancer Research* 48, 589–601 (1988) using SKBr3 and MCF7 cell lines. This refere-nce is incorporated herein in its entirety.

When the compounds of the formula I and their pharmaceutically acceptable salts are used as antiproliferative agents, such as anticancer agents, they can be administered to a mammalian subject either alone or, preferably in combination with pharmaceutically acceptable carriers or diluents in a pharmaceutical composition according to standard pharmaceutical practice. The compounds can be administered orally or parenterally. Parenteral administration includes intracenous, intramuscular, intraperitoneal, subcutaneous and topical.

In general, the active compounds are administered in dosage ranging from about 0.1 mg to about 20 mg per kg of body weight as needed (e.g., every 4 to 6 hours), preferably from about 0.1 to about 15 mg per kg of body weight; variations will necessarily occur depending upon the condition of the subject being treated and the particular compound and dosage form being administered. It is to be noted that these compounds may be administered in combination with pharmaceutically acceptable carriers by either of the routes previously indicated, and that such administration can be carried out in both single and multiple dosages.

The active compounds of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in, e. g., the U.S. Pat. Nos. 4,256,108; 4,166,452; and 4,265,874 to form osmotic therapeutic tablets for control release.

The hard capsules for oral use may also be presented as gelatin capsules wherein the active ingredient is mixed with an inert solid diluent, for example, calcium carbonate, calcium phosphate or kaolin, or whereas the soft capsules may be presented as gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methiylcellulose, hydroxy-propylmethylcellulose, sodium alginate, polyvinyl pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents may also be present.

The pharmaceutical compositions of the invention may also be in the form of oil-in water emulsions. The oily phase may be a vegetable oil, for example, olive oil or arachis oil; a mineral oil such as liquid paraffin or mixtures of these. Suitable emulsifying agents may be naturally occurring gums, for example, gum acacia or gum tragacanth; naturally-occurring phosphatides such as example soy bean and lecithin; and esters or partial esters derived from fatty acids and hexitol anhydrides, for example, sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulation may also contain a demulcent, a preservative and flavoring and coloring agents. The pharmaceutical compositions may be in the form of a sterile injectable aqueous or oleaginous suspension. This suspension may be formulated according to 1he known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables.

The active compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

For topical use, creams, ointments, Jellies, solutions cr suspensions, etc., containing the active compounds of the invention are employed.

For administration by inhalation, the active compounds of the invention are conveniently delivered in the form of an aerosol spray presentation from pressurized packs or a nebulizer. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

One or more other active compounds may be added to the formulations described above to provide formulations for combination therapy. Such compounds include cytostatic, cytotoxic and antiemetic agents conventionally used in cancer chemotherapy, such as adriamycin.

The following examples illustrate the invention but are not to be construed as limiting the same. All melting points are uncorrected. In the Examples, "BOC" refers to t-butoxycarbonyl.

EXAMPLES

General Methods

High pressure liquid chromatography (HPLC) was performed at 1.0 mL/minute with 254 nm detection on a 250×4.6 mm Dupont Zorbax Sil (trademark) column eluted isocratically by a two-pump/mixer system supplying the indicated mixture of 1% methanol in ethyl acetate and hexanes respectively. Samples to be thus analyzed are dissolved in an HPLC eluent. The HPLC retention times are reported followed by the ethylacetate/hexane ratio in parentheses. The terms "concentrated in vacuo" and "coevaporated" refer to removal of solvent at water aspirator pressure on a rotary evaporator with a bath temperature of less than 40° C.

EXAMPLE 1

17-Isopropylamino-4,5-dihydro-17-demethoxcygeldanamycin

To 4,5-dihydro-geldanamycin (75 mg, 0.13 mmol) in $CHCl_3$ was added isopropylamine (68 μL, 0.80 mmol) and the reaction stirred at room temperature for 24 hours at which time TLC analysis indicated the reaction was not complete. The reaction mixture was then heated at reflux for 3 hours. The solvent was removed by rotary evaporation and the purple residue partitioned between ethyl acetate and 1 M hydrochloric acid. The organic layer was dried, the solvent removed by rotary evaporation, and the crude material purified by column chromatography (silica gel, 9:1 $CH_2Cl_2$:methanol) to give the title compound as a purple solid; Yield 56 mg (72%), mp 114–115° C.; $^1$H-NMR (300 MHz, $CDCl_3$)δ0.95 (d, 3 H, J=7 Hz), 1.00 (d, 3 H, J=7 Hz), 1.2 (d, 3 H, J=7 Hz), 1.35 (d, 3 H, J=7 Hz), 1.7 (s, 3 H), 1.9 (s, 3 H), 2.2 (dd, 1 H, J=14, 7), 2.4 (dd, 1 H, J=14 Hz, 7 Hz), 2.5–2.8 (m, 1 H), 3.3 (m, 1 H), 3.35 (s, 3 H), 3.4 (s, 3 H), 3.4–3.5 (m, 1 H), 3.6 (d, 1 H, J=9 Hz), 3.7 (lr s,1 H), 4.1 (m, 1 H), 4.95(s,2H),5.2(d,1 H,J=7Hz Hz),5.75(d,1 H, J=9 Hz), 6.2(t,1 H, J=9 Hz), 7.1 (s, 1 H), 9.3 (br s, 1 H); mass spectrum m/z 612 (M+Na).

The compounds of Examples 2–14 were prepared from 4,5-dihydro-geldanamycin and the appropriate amines using the conditions described above.

EXAMPLE 2

17-Amino4,5-dihydro-17-demethoxygeldanamycin $^1$H-NMR (300 MHz, $CDCl_3$)δ0.95 (m, 6 H), 1.5–1.8 (m, 8 H, contains methyl singlet), 1.85 (s, 3 H), 2.0 (m, 1 H), 2.35 (m, 2 H), 2.6 (m, 1 H), 2.7 (m, 1 H), 3.2–3.5 (m, 8 H, contains 2 methyl singlets), 3.8 (m, 2 H), 5.0 (br s, 2 H), 5.1 (d, 1 H, J=4 Hz), 5.6 (br s, 2 H), 5.7 (d, 1 H, J=10 Hz), 6.2 (t, 1 H, J=7 Hz), 7.05 (s, 1 H), 9.15 (s, 1 H); mass spectrum m/z 547 (M$^+$); Analysis calculated for $C_{28}H_{41}N_3O_8 \cdot 0.5\ H_2$: C, 60.42; H, 7.60; N, 7.55%. Found: C, 60.42; H, 7.45; N, 7.51%.

EXAMPLE 3

17-Methylamino-4,5-dihydro-17-demethoxygeldanamycin

Mp 181° C.; $^1$H-NMR (300 MHz, $CDCl_3$)δ1.0 (m, 6 H), 1.5–1.8 (m, contains methyl singlet, 9 H), 1.9 (s, 3 H), 2.3–2.8 (m, 5 H), 3.2 (d, 3 H, J=7 Hz), 3.3–3.45 (m, contains 2 methyl singlets, 8 H), 3.45–3.55 (m, 1 H), 3.6 (br d, 1 H, J=7 Hz), 3.75 (br s, 1 H), 4.7 (br s, 2 H), 5.2 (d, 1 H, J=7 Hz), 5.8 (d, 1 H, J=10 Hz), 6.25 (t, 1 H, J=7 Hz), 6.4–6.55 (m, 1 H), 7.15 (s, 1 H), 9.3 (br s, 1 H); mass spectrum m/z 561 (M$^+$); Analysis calculated for $C_{29}H_{43}N_3O_8$: C, 62.01; H, 7.72; N, 7.48%. Found: C, 61.60; H, 7.73; N, 7.16%.

EXAMPLE 4

17-Cyclopropylamino-45-dihydro-17-demethoxygeldanamycin

Mp 146–147° C.; $_1$H-NMR (300 MHz, $CDCl_3$)δ0.6-0.9 (m, 4 H), 0.9–1.1 (m, 6 H), 1.5–1.8 (m, contains methyl singlet, 6 H), 1.9 (s, 3 H), 2.3–2.5 (m, 2 H), 2.5–2.8 (m, 2 H), 2.8–3.0 (m, 2 H), 3.2–3.4 (m, contains 2 methyl singlets, 8 H), 3.4–3.5 (m, 1 H), 3.5–3.7 (br d, 2 H), 4.9 (br s, 2 H), 5.15 (d, 1 H, J=7 Hz), 5.75 (d, 1 H, J=10 Hz), 6.2 (t, 1 H, J=7 Hz), 6.35 (d, 1 H, J=3), 7.1 (s, 1 H), 9.25 (br s, 1 H); mass spectrum m/z 587 (M$^+$); Analysis calculated for $C_{31}H_{45}N_3O_8 \cdot 0.5\ H_2O$: C, 62.40; H, 7.77; N, 7.04%. Found: C, 62.55; H, 7.61; N, 6.83%.

EXAMPLE 5

17-Allylamino-4,5-dihydro-17-demethoxygeldanamycin

Mp 205° C.; $^1$H-NMR (300 MHz, $CDCl_3$)δ1.0 (m, 6 H, 2 methyl doublets), 1.5–1.8 (m, 8 H, contains methyl singlet), 1.9 (s, 3 H), 2.2–2.5 (m, 3 H), 2.5–2.8 (m, 2 H), 3.2–3.5 (m, 8 H, contains 2 methyl groups), 3.6 (d, 1 H, J=7 Hz), 4.1 (m, 2 H), 4.8 (s, 2 H), 5.2 (d, 1 H, J=7Hz), 5.25 (d, 1 H, J=10 Hz), 5.3 (s, 1 H), 5.75 (d, 1 H, J=10 Hz), 5.9 (m, 1 H), 6.25 (t, 1 H, J=7 Hz), 6.4 (br t, 1 H), 7.25 (s, 1 H), 9.25 (br s, 1 H); mass spectrum m/z 610 (M+Na); Analysis calculated for $C_{31}H_{45}N_3O_8 \cdot 0.5\ H_2O$: C, 62.40; H, 7.77; N, 7.04%. Found: C, 62.26; H, 7.83; N, 6.75%.

EXAMPLE 6

17-(2'-Hydroxnethylamino)-4,5-dihydro-17-demethoxygeldanamycin

Mp 129° C. (foam); $^1$H-NMR (300 MHz, $CDCl_3$) δ0.9–1.1 (m, 6 H), 1.6–1.8 (m, contains methyl singlet, 8 H), 1.9 (s, 3 H), 2.3–2.5 (m, 3 H), 2.7–2.8 (m, 2 H), 3.2–3.5 (m, contains 2 methyl singlets, 8 H), 3.55–3.65 (d, 1 H, J=10 Hz), 3.65–3.8 (m, 2 H), 3.8–4.0 (m, 1 H), 4.85 (br s, 2 H), 5.15 (d, 1 H, J=4 Hz), 5.78 (d, 1 H, J=10Hz), 6.2 (t, 1 H, J=7 Hz), 7.1 (s, 1 H), 9.21 (s, 1 H); mass spectrum m/z 591 (M$^+$); Analysis calculated for $C_{30}H_{45}N_3O_9$: C, 60.90; H, 7.67; N, 7.10%. Found: C, 60.40; H, 7.89; N, 6.63%.

EXAMPLE 7

17-(2'-Methoxyethylamino)-4,5-dihydro-17-demethoxygeldanamycin

Mp 115° C. (dec); $^1$H-NMR (300 MHz, $CDCl_3$)δ0.8–1.0 (m, 6 H), 1.5–1.8 (m, contains broad methyl singlet, 7 H), 1.85 (br s, 3 H), 2.2–2.5 (m, 3 H), 2.5–2.8 (m, 2 H), 3.2–3.5 (m, contains 3 methy singlets, 12 H), 3.5–3.8 (m, 5 H), 5.0 (br s, 2 H), 5.15 (d, 1 H, J=7 Hz), 5.7 (d, 1 H, J=10 Hz), 6.2 (brt, 1 H, J=7 Hz), 6.55 (br s, 1 H), 7.1 (s, 1 H), 9.25 (br s, 1 H); mass spectrum m/z 605 (M$^+$); Analysis calculated for $C_{31}H_{47}N_3O_9$: C, 61.47; H, 7.82; N, 6.94%. Found: C, 61.0; H, 7.58; N, 6.71%.

EXAMPLE 8

17-(2'-Fluoroethylamino)-4,5-dihydro-17-demethoxygeldanamycin

Mp 157° C. (foam); $^1$H-NMR (300 MHz, $CDCl_3$)δ1.0 (m, 6 H), 1.6–1.8 (m, contains methyl singlet, 8 H), 1.9 (s, 3 H), 2.0–2.1 (br s, 1 H), 2.2–2.5 (m, 3 H), 2.6–2.8 (m, 2 H), 3.2–3.7 (m, contains 2 methyl singlets, 8 H), 3.7–4.0 (m, 2 H), 4.55 (t, 1 H, J=7Hz), 4.7–4.85 (m, 3 H), 5.2 (d, 1 H, J=7 Hz), 5.8 (d, 1 H, J=10 Hz), 6.25 (t, 1 H, J=7 Hz), 6.4 (t, 1 H, J=7 Hz), 7.15 (s, 1 H), 9.2 (s, 1 H); mass spectrum m/z 593 (M$^+$).

EXAMPLE 9

17-(2'-Methylthioethylamino)-4,5-dihydro-17-demethoxygeldanamycin

Mp 110° C. (foam); $^1$H-NMR (300 MHz, CDCl$_3$)δ1.0 (m, 6 H), 1.5–1.75 (m, contains methyl singlet, 8 H), 1.85 (s, 3 H), 2.1 (s, 3 H), 2.2–2.4 (m, 3 H), 2.5–2.8 (m, 4 H), 3.2–3.5 (m, contains 2 methyl singlets, 8 H), 3.5–3.8 (m, 4 H), 5.0 (s, 2 H), 5.15 (d, 1 H, J=4 Hz), 5.75 (d, 1 H, J=10 Hz), 6.2 (t, 1 H, J=7 Hz), 6.6 (t, 1 H, J=4 Hz), 7.1 (s, 1 H), 9.2 (s, 1 H); mass spectrum m/z 644 (M+Na); Analysis calculated for C$_{31}$H$_{47}$N$_3$O$_8$S.0.5 H$_2$O: C, 59.03; H, 7.67; N, 6.66%. Found: C, 58.87; H, 7.67; N, 6.60%.

EXAMPLE 10

17-[s-(+)-2'-Hydroxypropylaminol]-4,5-dihydro-17-demethoxygeldanamycin $^1$H-NMR (300 MHz, CDCl$_3$)δ0.95 (d, 3 H, J=7 Hz), 1.0 (d, 3 H, J=7 Hz), 1.3 (d, 3 H, J=7 Hz), 1.5–1.75 (m, contains methyl singlet, 6 H), 1.85 (s, 3 H), 2.25–2.45 (m, 2 H), 2.6–2.7 (m, 1 H), 3.2–3.5 (m, contains 2 methyl singlets, 8 H), 3.5–3.7 (m, 2 H), 4.05 (m, 1 H), 4.9 (s, 2 H), 5.15 (d, 1 H, J=7 Hz), 5.8 (d, 1 H, J=7 Hz), 6.2 (t, 1 H, J=7 Hz), 6.7 (br s, 1 H), 7.05 (s, 1 H), 9.2 (br s, 1 H); mass spectrum m/z 605.3(M$^+$).

EXAMPLE 11

17-(2'-Cyanoethylamino)-4,5-dihydro-17-demethoxygeldanamycin

Mp 130–140° C. (foam); $^1$H-NMR (300 MHz, CDCl$_3$) δ1.0 (m, 6 H), 1.5–1.8 (m, contains methyl singlet, 8 H), 1.9 (s, 3 H), 2.0–2.2 (m, 2 H), 2.4 (q, 2 H, J=7 Hz), 2.6–2.8 (m, 4 H), 3.2–3.5 (m, contains 2 methyl singlets, 8 H), 3.6 (br cl, 1 H, J=7 Hz), 3.85 (q, 2 H, J=7Hz), 4.75 (br s,2 H), 5.2 (d, 1 H, J=7Hz), 5.75 (d, 1 H, J=10Hz), 6.2 (q, 2 H, J=7 Hz), 7.15 (s, 1 H), 9.15 (s, 1 H); mass spectrum m/z 600 (M$^+$); Analysis calculated for C$_{31}$H$_{44}$N$_4$O$_8$: C, 61.98; H, 7.38; N, 9.33%. Found: C, 61.30; H, 7.31; N, 9.12%.

EXAMPLE 12

17-Azetidin-1-yl-5-dihydro-17-demethoxyceldanamycin

Mp 110° C. (foam); $^1$H-NMR (300 MHz, CDCl$_3$)δ0.95 (d, 3 H, J=7 Hz), 1.0 (d, 3 H, J=7 Hz), 1.7 (s, 3 H), 1.6–1.8 (m, 9 H), 1.9 (s, 3 H), 2.2 (d, 1 H, J=14 Hz, 7 Hz), 2.3–2.55 (m, 4 H), 2.65 (d, 1 H, J=14 Hz), 2.75 (m, 1 H), 3.35 (m, 1 H), 3.38 (s, 3 H), 3.4 (s, 3 H), 3.5 (m, 1 H), 3.6 (d, 1 H, J=10 Hz), 4.5–4.8 (m, 6 H), 5.2 (d, 1 H, J=7 Hz), 5.7 (d, 1 H, J=10 Hz), 6.25 (t, 1 H, J=10 Hz), 7.0 (s, 1 H), 9.3 (br s, 1 H); mass spectrum m/z 587 (M$^+$).

EXAMPLE 13

17-(3'-Hydroxyazetidin-1-yl)-4,5-dihydro-17-demethoxygeldanamycin

Mp (amorphous); $^1$H-NMR (300 MHz, CDCl$_3$)δ1.0 (m, 6 H), 1.5–1.8 (m, contains 1 methyl singlet, 8 H), 1.9 (s, 3 H), 2.2 (m, 1 H), 2.35 (m, 2 H), 2.6 (br d, 1 H, J=14 Hz), 2.75 (m, 1 H), 3.2–3.5 (m, contains 2 methyl singlets, 8 H), 3.6 (d, 1 H, J=10 Hz), 4.3–4.6 (m, 2 H), 4.7 (m, 1 H), 4.75–5.0 (m, 4 H), 5.15 (d, 1 H, J=4 Hz), 5.8 (d, 1 H, J=10 Hz), 6.2 (br t, 1 H, J=7 Hz), 6.95 (s, 1 H), 9.2 (s, 1 H); mass spectrum m/z 626 (M+Na); Analysis calculated for C$_{31}$H$_{45}$N$_3$: C, 61.68; H, 7.51; M, 6.96%. Found: C, 61.21; H, 7.51; N, 6.75%.

EXAMPLE 14

17-(3'-Methoxyazetidin-1-yl)-4,5-dihydro-17-demethoxygedanamycin

Mp 118° C. (foam); $^1$H-NMR (300 MHz, CDCl$_3$)δ1.0 (m, 6 H, two methyl doublets), 1.5–1.8 (m, 8 H, contains methyl singlet), 1.9 (s, 3 H), 2.0–2.3 (m, 1 H), 2.4 (m, 2 H), 2.5–2.8 (m, 2 H), 3.2–3.5 (m, 11 H, contains 3 methyl singlets), 3.6 (m, 1 H), 4.0 (d, 1 H, J=7 Hz), 4.2 (m, 1 H), 4.34.6 (m, 2 H), 4.64.9 (m, 4 H), 5.2 (d, 1 H, J=4 Hz), 5.8 (d, 1 H, J=10 Hz), 6.25 (br t, 1 H, J=7 Hz), 7.0 (s, 1 H), 9.25 (s, 1 H); mass spectrum m/z 640 (M$^+$+Na); Analysis calculated for C$_{32}$H$_{47}$N$_3$O$_9$.H$_2$O: C, 60.84; H, 7.18; N, 6.65%. Found: C, 60.74; H, 7.54; N, 6.75%.

EXAMPLE 15

17-Azetidin-1-yl-4,5-dihydro-11-α-fluoro-17-demethoxygeldanamycin

A solution of diethylaminosulfurtrifluoride (DAST) (0.154 g, 0.960 mmol, 0.127 mL) in 3 mL of methylene chloride was added to a flame dried flask under nitrogen and cooled to –68° C. with an external dry ice/acetone bath. 17-Azetidine-1-yl-4,5-dihydro-17-demethoxygeldanamycin (0.188 g, 0.320 mmol) dissolved in 15 mL of methylene chloride was added dropwise. After 0.5 hour 5 mL of 5% aqueous NaHCO$_3$ was added slowly at about –68° C. After warming to room temperature the product was extracted into 100 mL of methylene chloride. The organic layer was washed with 3×50 mL of water and 2×50 mL of brine, dried with MgSO$_4$, filtered and concentrated to a purple solid which was purified by flash column chromatography using 5:95 methanolhloroform. Material of Rf=0.42 (1:9 methanol:chlciroform), the desired product was disolved in a minimal amount of ethyl acetate and precipitated with hexanes; Yield 0.096 9 (51%), mp 104° C. (dec); $^1$H-NMR (300 MHz, CDCl$_3$)δ1.00(d, J=8 Hz, 3H, 14–CH$_3$), 1.06(d, J=8 Hz, 3H, 10–CH$_3$), 1.4 (br m, 2H, H-13),1.56 (s, 3H, 8-CH$_3$), 1.75 (m, 1H, H-14), 1.89 (s, 3H, 2-CH$_3$), 2.20 (dd, J=8.5 Hz, 16 Hz, 1H, H-15), 2.4 (br m, 3H, 3' azetidine CH$_2$ and H-5), 2.66 (dd, J=7 Hz, 16 Hz, 1 H, H-15), 2.75 (br d, J=26 Hz, 1H, H-10), 3.25 (m, 1H, H4), 3.4 (br s, 7H, 6-OCH$_3$, 12-OCH$_3$ and H-4), 3.60 (br m, 1 H, H-12), 4.40 (br d, J=44 Hz, 1 H, H-11), 4.65 (br m, 7H, NH$_2$ and 2' and 4' azetidine CH$_2$ and H-6), 5.06 (d, J=8 Hz, 1H, H-7), 5.62 (d, J=9 Hz, 1H, H-9), 6.13 (br t, 1H, H-3), 6.96 (s, 1H, H-19), 9.27 (s, 1H, NH-22); m/z 612. (M++Na); IR (KBr, cm$^{-1}$) 1735, 1695, 1650; Analysis calculated for C$_{31}$H$_{44}$FN$_3$O$_7$.0.25H$_2$O: C, 62.66; H, 7.96; N, 7.07%. Found: C, 62.38; H, 7.53; N, 6.97%.

EXAMPLE 16

17-Allylamino-4,5-dihydro-11-α-fluoro-17-demethoxygeldanamycin

The title compound was made by the method of Example 15 from 17-allylamino-4,5-dihydro-17- demethoxygeldanamycin. Yield 0.079 g (44%), mp 84° C. (dec); $^1$H-NMR (300 MHz, CDCl$_3$)δ1.02(d, 3H, J=8Hz, 14-CH$_3$), 1.07(d, 3H, J=8Hz, 10-CH$_3$), 1.45 (br m, 2H, H-13), 1.60 (s, 3H, 8-CH$_3$), 1.7 (m, 2H, H-5), 1.83 (br m, 1H, H-14), 1.90 (s, 3H, 2-CH$_3$), 2.30 (dd, J=8.5 Hz, 16 Hz, 1H, H-15), 2.4 (m, 2H, H-4), 2.70 (dd, J=7 Hz, 16 Hz,1 H, H-15), 2.75 (br d, J=26 Hz,1 H, H-10), 3.26 (m,1 H, H-6), 3.40 and 3.43 (br s, 6H, OCH$_3$), 3.57 (br m, 1 H, H-1 2), 4.08 (br t, 2H, allylic CH$_2$), 4.35 (br d, J=47 Hz, 1 H, H-11), 4.65 (br m, 2H, NH$_2$), 5.07 (s, 1H, H-7), 5.25 (br d, 2H, vinylic CH$_2$), 5.61 (d, J=9 Hz, 1H, H-9), 5.9 (m, 2H, H-5 and vinylic CH), 6.15 (br t, 1H, H-3), 6.32 (br t, 1H, NH), 7.15 (s, 1H, H-19), 9.25 (s, 1H, NH-22); m/z 612. (M++Na); IR (KBr, cm$^{-1}$) 1730,1695,1655; Analysis calculated for C$_{31}$H$_4$FN$_3$O$_7$0.25H$_2$O: C, 62.66; H, 7.96; N, 7.07%. Found: C, 62.53; H, 7.32; N, 6.97%.

EXAMPLE 17

17-Azetidin-1-yl-4,5-dihydro-11-keto-17-demethoxygeldanamycin

Prepared from 17-azetidin-1-yl4,5-dihydro-17-demethoxygeldanamycin by the method of Example 76; $^1$H-NMR (300 MHz, CDCl$_3$)δ1.0 (d, 3 H, J=6), 1.3 (d, 3 H, J=6), 1.35-1.5 (m, 2 H), 1.5–1.8 (m, 6 H, contains methyl singlet), 1.9 (s, 3 H), 2.15–2.3 (m, 2 H), 2.45–2.5 (m, 2 H), 2.6 (m, 1 H), 3.15 (m, 1 H), 3.35 (s, 3 H), 3.4 (s, 3 H), 3.55 (m, 1 H), 4.0 (m, 1 H), 4.65 (m, 4 H), 4.8 (br s, 2 H), 5.0 (d, 1 H, J=6 Hz), 5.55 (d, 1 H, J=8 Hz), 6.25 (m, 1 H), 6.92 (s, 1 H), 9.2 (s, 1H); mass spectrum m/z 608 (M+Na);

EXAMPLE 18

17-Azetidin-1-yl-17-demethoxygeldanamycin

Geldanamycin (14.0 gm, 25.0 mmol) was added to a flame dried flask under nitrogen and slurried in 350 mL of methylene chloride. Azetidine (2.85g, 49.9 mmol, 3.36 mL) in 10 mL of methylene chloride was added dropwise. The yellow suspension turned purple during the addition. After 1 hour the reaction mixture was evaporated to dryness and the residue dissolved in 50 mL of chloroform and precipitated with 600 mL of hexanes. Filtration and vacuum drying at 70° C. afforded pure product, yield 14.2 gm (97%); 225 C; $^1$H-NMR (300 MHz, CDCl$_3$)δ0.94 (br t, 6H, 10-CH$_3$ and 14-CH$_3$), 1.2 (m, 1H, H-13), 1.65 (m, 1H, H-13), 1.73 (m, 1H, H-14), 1.76 (s, 3H, 8-CH$_3$), 2.0 (s, 3H, 2-CH$_3$), 2.17 (dd, J=12 Hz, 16 Hz, 1H, H-15), 2.40 (p, J=8 Hz, 2H, 3' azetidine CH$_2$), 2.56 (d, J=16 Hz, 1H, H-15), 2.67 (m, 1H, H-10), 3.20(s, 3H, OCH$_3$), 3.30 (s, 3H, OCH$_3$), 3.40 (m, 1H, H-12), 3.50 (m, 1H, H-11), 4.25 (d, J=10.5 Hz, 1H, H-6), 4.54.9 (m, 6H, 2' and 4' azetidine CH$_2$ and NH$_2$), 5.13 (s, 1H, H-7), 5.79 (t, J=9 Hz, 1H, H-5), 5.87 (d, J=9 Hz, 1H, H-9), 6.53 (t, J=9 Hz, 1H, H-4), 6.88 (d, J=9 Hz, 1H, H-3), 7.06 (s, 1H, H-19), 9.13 (s, 1H, NH-22); m/z 608. (M++Na); IR (KBr, cm −1) 1730, 1680, 1645; Analysis calculated for C$_{31}$, H$_{43}$N$_3$O$_8$: C,63.54; H, 7.40; N, 7.17%; Found: C, 63.09; H, 7.33; N, 6.85%.

EXAMPLE 19

17-Propargylamino-17-demethoxygeldanamycin

Propargylamine hydrochloride (0.200 gm, 2.180 mmol) and triethylamine (0.2206 gm, 2.180 mmol, 0.303 mL) were added to a flame dried flask under nitrogen and slurried in 5 mL chloroform. After 10 minutes geldanamycin (0.200 gm, 0.3567 mmol) was added to the mixture and the reaction was stirred at room temperature overnight. The solution changed from a pale yellow color to a dark orange/red color. The reaction mixture was diluted with 50 mL chloroform and washed with 3×25 mL 1N hydrochloric acid. The organic layer was then dried over magnesium sulfate, fill ered and evaporated to dryness to yield a crude purple residue. The crude product was then purified by flash column chromotography using 200 gm silica gel and eluting with 3:97 isopropyl alcohol:methylene chloride to afford pure purple product, 0.015 gm (7%) mp 172° C.; $^1$H-NMR (300 MHz, CDCl$_3$)δ0.96–1.10 (m, 1H, H-13), 1.00 (d, J=8 Hz, 3H, 1-CH$_3$), 1.01 (d, J=8 Hz, 3H, 14-CH$_3$), 1.62–1.90 (br m, 2H, H-13, H-14), 1.76 (s, 3H, 8-CH$_3$), 2.04 (s, 3H, 2-CH$_3$), 2.34–2.47 (br m, 1H, H-1 5), 2.42 (s, 1H, acelylene CH), 2.68–2.81 (br m, 2H, H-10, H-15), 3.28 (s, 3H, OCH$_3$), 3.47 (s, 3H, OCH$_3$), 3.49 (br m, 1H, H-12), 3.61 (br m, 1H, H-11), 4.02 (d, J=6 Hz, 1H, H-6), 4.31 (s, 1H, 11-OH), 4.32 (m, 2H, propargyl CH2), 4.77 (br m, 2H, NH$_2$), 5.21 (s, 1H, H-7), 5.87 (t, J=9 Hz, 1 H, H-5), 5.90 (d, J=9 Hz, 1H, H-9), 6.32 (br t, 1H, NH), 6.60 (t, J=9 Hz, 1H, H-4), 6.97 (d, J=9 Hz, 1H, H-3), 7.32 (s, 1H, H-19), 9.09 (s, 1H, NH-22); m/z 606.3 (M++Na); IR (KBr, cm $^{−1}$) 2120, 1730, 1695, 1645; Analysis calculated for C$_{31}$H$_{41}$N$_3$O$_8$.3.50H$_2$O: C, 57.55; H, 7.47; N, 6.49%. Found: C, 57.55; H, 6.14; N, 6.23%.

EXAMPLE 20

17-(2'-Cyanoethylamino)-17-demethoxygeldanamycin

Geldanamycin (0.200 gm, 0.3567 mmol) was added to a flame dried flask under nitrogen and slurried in 5 mL chloroform. 3-Aminopropionitrile 0.153 gm (2.18 mmol, 0.161 mL) was added and the reaction mixture was stirred att room temperature overnight. The reaction mixture went from a pale yellow color to a dark red/orange color. An additional 0.161 mL of 3-aminopropionitrile was added and the reaction mixture was refluxed for 8 hours. The cooled reaction mixture was diluted with 75 mL chloroform and washed with 3×50 mL water. The organic layer was dried over magnesium sulfate, filtered and evaporated to dryness. The purple residue was recrystallized from a minimal amount of hot ethyl acetate affording pure purple product, 0.160 gm (75%) mp 152° C.; $^1$H-NMR (300 MHz, CDCl$_3$) δ0.74–0.91 (br m, 1H, H-13), 0.82 (d, J=7 Hz, 3H, 10-CH$_3$) 0.82 (d, J=7 Hz, 3H, 14-CH$_3$), 1.45–1.7 (br m, 2H, H-13, H-14),1.61 (s, 3H, 8-CH$_3$),1.83 (s, 3H, 2-CH$_3$), 1.93–2.09 (br m, 1H, H-15), 2.49–2.64 (m, 4H, β-ethyl CH$_2$, H-10, H-15), 3.08 (s, 3H, OCH$_3$), 3.19(s, 3H, OCH$_3$), 3.28 (br m, 1H, H-12), 3.39 (m, 1H, 11-H), 3.62–3.79 (br m, 2H, α-ethyl CH$_2$), 4.12 (d, J=9 Hz, 1H, H-6), 4.62 (br m, 2H, NH$_2$), 5.00 (s, 1 H, H-7), 5.62–5.72 (br m, 2H, H-5, H-9), 5.96 (br t, 1 H, NH), 6.40 (t, J=9 Hz, 1H, H-4), 6.78 (d, J=9 Hz, 1H, H-3), 7.12 (s, 1H, H-19), 8.82 (s, 1H, NH-22); m/z 621.3 (M++ Na); IR (KBr, cm$^{−1}$) 1730, 1690, 1650, 1585, 1480; Analysis calculated for C$_{31}$H$_{42}$N$_4$O$_8$: C, 62.19; H, 7.07; N, 9.35%. Found: C, 62.02; H, 6.63; N, 9.09%.

EXAMPLE 21

17-(2'-Fluoroethylamino)-17-demethoxygeldanamycin 17-(2'-Fluoroethylamino)-17-demethoxygeldanamycin was prepared by the method of Example 19. Pure purple product was obtained from the crude residue after flash column chromatography using 200 gm silica gel eluting with 20% acetone in methylene chloride; yield 0.060 gm (28%) mp 176° C.; $^1$H-NMR (300 MHz, CDCl$_3$)δ0.87 (d, J=7 Hz, 3H, 10-CH$_3$), 0.91 (d, J=7 Hz, 3H, 14-CH$_3$), 1.55–1.73 (br m, 3H, H-13, H-14), 1.70 (s, 3H, 8-CH$_3$), 1.92 (s, 3H, 2-CH$_3$), 2.21 (dd, J=8 H;z, 16 Hz, 1H, H-15), 2.62 (br m, 2H, H-10, H-15), 3.14 (s, 3H, OCH$_3$), 3.24 (s, 3H, OCH$_3$), 3.35 (br m, 1H, H-12), 3.48 (br m, 1H, H-11), 3.59–3.91 (br m, 2H, α-ethyl CH$_2$), 4.19 (d, J=9 Hz, 1H, H-6), 4.65 (two br t, J=46 Hz, 5 Hz, 2H, β-ethyl CH$_2$), 4.52–4.79 (br m, 2H, NH$_2$), 5.07 (s, 1 H, H-7), 5.72 (br m, 2H, H-5,H-9), 6.29 (br t, 1 H, NH), 6.48 (t, J=9 Hz, 1 H, H-4), 6.85 (d, J=9 Hz, 1H, H-3), 7.14 (s, 1H, H-19), 8.97 (s, 1H, NH-22); m/z 591.3. (M+); IR (KBr, cm$^{-1}$) 1742, 1655, 1585; Analysis calculated for C$_{30}$H$_{42}$N$_3$O$_8$: C, 60.90; H, 7.15; N, 7.10%. Found: C, 60.65; H, 6.90; N, 6.92%.

EXAMPLE 22

17-tert-Butylamino-17-demethoxy-geldanamycin

Geldanamycin (0.200 gm, 0.3567 mmol) was slurried in 5 mL of tert-butylamine, in a flame dried flask under nitrogen, at reflux overnight. The reaction color went from yellow to dark purple. The reaction mixture was evaporated to dryness. The residue was dissolved into 50 mL chloroform. The chloroform s;olution was washed with 3×25 mL brine and 3×25 mL water. The organic layer was dried over magnesium sulfate, filtered and evaporated to dryness. The crude product was purified by flash column chromatagraphy with 200 gm silica gel eluted with 10% acetone/methylene chloride; yield 0.053 gm (25%) mp 102° C. (dec); $^1$H-NMR (300 MHz, CDCl$_3$)δ0.89 (d, J=5 Hz, 3H, 10-CH$_3$), 0.94 (d, J=5 Hz, 3H, 14-CH$_3$), 1.39 (s, 9H, t-butyl CH$_3$), 1.49–1.80 (br m, 3H, H-13, H-14), 1.74 (s, 3H, 8-CH$_3$), 1.98 (s, 3H, 2-CH$_3$), 2.27 (br m, 1H, H-15), 2.65 (br m, 2H, H-10, H-15), 3.21 (s, 3H, OCH$_3$), 3.30 (s, 3H, OCH$_3$), 3.99 (br m, 1H, H-12), 3.45 (br m, 1H, H-11), 4.17 (br m, 1H, 11-OH), 4.23 (d, J=7 Hz, 1H, H-6), 4.72–4.91 (br m, 2H, NH$_2$), 5.13 (s, 1H, H-7), 5.82 (br m, 3H, H-5, H-9, NH), 6.51 (t, J=7 Hz, 1H, H-4), 6.87 (d, J=7 Hz, 1H, H-3), 7.18 (s, 1H, H-19), 8.96 (s, 1H, NH-22); m/z 601.4 (M+); 1R (KBr, cm$^{-1}$) 1720, 1685, 1645, 1585, 1560; Analysis calculated for C$_{32}$H$_{47}$N$_3$O$_8$: C, 63.87; H, 7.87; N, 6.98%. Found: C, 63.91; H, 7.95; N, 6.03%.

EXAMPLE 23

17-(2'-Mercaptoethylamino)-17-demethoxygeldanamycin

Geldanamycin (0.200 gm, 0.3567 mmol) was added to a flame dried flask under nitrogen and slurried in 5 mL pyridine. Thiazolidine (0.194 gm, 2.18 mmol, 0.171 mL) was added and the reaction mixture was heated at 70° C. for 2 hours. The reaction mixture was evaporated to dryness in vacuo. The crude product was purified by flash column chromatography using 200 gm silica gel eluting with -4% methanol in methylene chloride to afford pure purple product, 0.041gm (20%) mp 156° C.; $^1$H-NMR (300 MHz, CDCl$_3$)δ0.99 (d, J=5 Hz, 6H, 10-CH$_3$,14-CH$_3$),1.63–1.81 (br m, 3H, H-1 3, H-14), 1.78 (s, 3H, 8-CH$_3$), 2.01 (s, 3H, 2-CH$_3$), 2.47(m, 1 H, H-15), 2.64–2.79 (br m, 2H, H-10, H-15), 2.83–3.00 (br m, 2H, 2'-CH$_2$), 3.25 (s, 3H, OCH$_3$), 3.35 (s, 3H, OCH$_3$), 3.42 (m, 1H, H-12), 3.55 (m, 1H, H-11), 3.87 (m, 2H, 1'-CH$_2$), 4.10 (br m, 1H, 11-CH), 4.29 (d, J=9 Hz, 1H, H-6), 4.92 (br m, 2H, NH$_2$), 5.16 (s, 1 H, H-7), 5.81–5.89 (br m, 2H, H-5, H-9), 6.48 (br t, 1H, NH), 6.55 (t, J=9 Hz, 1 H, H-4), 6.94 (d, J=9 Hz, 1H, H-3), 7.24 (s, 1 H, H-19), 9.12(s, 1H, NH-22); m/z 642.3(M++Na); IR (CHCl$_3$, cm$^{-1}$) 1730, 1690, 1655, 1575; Analysis calculated for C$_{30}$H$_{44}$N$_3$O$_8$S.H$_2$O; C, 57.67; H,7.41; N, 6.72%. Found: C, 57.44; H, 6.37; N, 6.72%.

EXAMPLE 24

17-[2'Methylthio)ethylaminol]-17-demethoxygeldanamycin

Geldanamycin (0.200 gm, 0.3567 mmol) was added to a flame dried flask under nitrogen and slurried in 5 mL chloroform. 2-(Methylthioethylamine (0.199 gm, 2.18 mmol,) was added and the reaction was stirred at room temperature for 36 hours. The reaction mixture was diluted with 75 mL chloroform and washed with 2×50 mL 1N hydrochloric acid, 2×50 mL brine and 3×50 mL water. The organic layer was dried over magnesium sulfate, filtered and evaporated to dryness. The crude product was purified by flash column chromatography using 200 gm silica gel and eluting with 3% acetonitrile in ethyl ether to afford pure purple product, 0.095gm (43%) mp 157° C.; $^1$H-NMR (300 MHz, CDCl$_3$)δ1.09(d, J=7 Hz, 3H, 14-CH$_3$), 1.14 (d, J=7 Hz, 3H, 10-CH$_3$), 1.71–1.89 (br m, 3H, H-13, H-14), 1.89 (s, 3H, 8-CH$_3$), 2.13 (s, 3H, 2-CH$_3$), 2.22 (s, 3H, SCH3), 2.46 (dd, J=7Hz, 13Hz, 1H, H-15), 2.79 (d, J=13 Hz, 1H, H-15), 2.72–2.92 (br m, 3H, 2'-CH$_2$, H-10), 3.36 (s, 3H, OCH$_3$), 3.46 (s, 3H, OCH$_3$), 3.54 (m, 1H, H-12), 3.68 (t, J=7 Hz, 1H, H-11), 3.72–3.86 (br m, 1H, 1'CH$_2$), 3.86–3.95 (br m, 1H, 1'CH$_2$), 4.41 (d, J=7 Hz, 2H, H-6, 11-OH), 4.93(br m, 2H, NH$_2$), 5.28 (s, 1 H, H-7), 5.91–6.04 (br m, 2H, H-5, H-9), 6.62–6.74 (br m, 2H, H-4, NH), 7.03(d, J=7 Hz, 1 H, H-3), 7.37 (s, 1 H, H-19), 9.22 (s, 1 H, NH-22); m/z 642.3 (M++Na); I (CHCl$_3$, cm $^{-1}$) 1735, 1685, 1650, 1570; Analysis calculated for C$_{31}$H$_{45}$N$_3$O$_8$S.1.5H$_2$O: C, 57.56; H, 7.48; N, 6.49%. Found: C, 57.30; H, 6.87; N, 6.21%.

EXAMPLE 25

17-[(S)-2'-Azetidinecarboxylicacid]-17-demethoxygeldanamrycin

Geldanamycin (0.200 gm, 0.3567 mmol) was added to a flame dried flask under nitrogen and slurried in 5 mL chloroform. (S)-2-Azetidine carboxylic acid (0.200 gm, 1.978 mmol) in 2 mL of pyridine, and triethylamine (0.200 gm, 1.978 mmol, 0.275 mL) were added. The reaction mixture was stirred at room temperature for 36 hours, refluxed for 4 hours, cooled to room temperature, diluted with 75 mL chloroform and washed with 2×50 mL 1N hydrochloric acid. The organic layer was extracted with 3×50 mL 1N NaOH. The pooled basic phases were acidified to pH=6 with 1N hydrochloric acid and extracted with 3×75 mL chloroform. The combined chloroform layers were dried over magnesium sulfate, filtered, and evaporated to dryness. The residue was dissolved in a minimal amount of ethyl acetate and precipitated with hexane to afford pure purple product, 0.056 gm (25%) mp 2,0° C. (dec); $^1$H-NMR (C$_5$D$_5$N)δ1.29–1.47 (br m, 6H, 10-CH$_3$, 14-CH$_3$), 1.94–2.22 (br m, 3H, H-13, H-14), 2.09 (s, 3H, 8-CH$_3$), 2.23 (s, 3H, 2-CH$_3$), 2.49 (br m, 1H, H-15), 2.81 (t, J=7 Hz, 1 H, H-10), 2.99 (br m, 1H, 4'azetidine-CH), 3.28(br m, 1H, 4'azetidine-CH), 3.42 (s, 3H, OCH$_3$), 3.50 (s, 3H, OCH$_3$) 3.81 (m, 1H, H-12), 4.14 (m, 1H, H-11), 4.34 (br m, 1H, 3'azetidine-CH), 4.89 (br m, 1H, 3'azetidine-CH), 5.01 (d, J=7 Hz, 1H, H-6), 5.73 (m, 1H, 2'azetidine-CH), 5.91 (s, 1H, H-7 ), 6.21 (t, J=7 Hz, 1H, H-5), 6.47 (d, J=7 Hz, 1H, H-9), 6.60 (t, J=7 Hz, 1 H, H-4), 7.41–7.54 (br m, 2H, H-3, H-19), 9.57 (s, 1 H, NH-22); m/z 652.3 (M++Na); IR (CHCl$_3$, cm$^{-1}$) 1730, 1695, 1645, 1585; Analysis calculated for C$_{32}$H$_{43}$N$_3$O$_{10}$.3H$_2$O: C, 56.21; H, 7.22; N, 6.14%. Found: C, 56.16; H, 6.13; N, 6.04%.

The compounds of Examples 26–31 were prepared from geldanamycin and the appropriate amines by the method of Example 1 above.

EXAMPLE 26

17-Histamino-17-demethoxygeldanamycin

Mp 150° C. (decomp); $^1$H-NMR (300 MHz, CDCl$_3$)δ0.98 (overlapping d, 6 H), 1.68 (m, 1 H), 1.77 (s, 3 H), 2.02 (s, 3 H), 2.43 (t, 1 H, J=7 Hz), 2.6–2.8 (m, 2 H), 2.94 (t, 2H, J=5 Hz), 3.23 (s, 3 H), 3.39 (s, 3 H), 3.40 (m, 1 H), 3.52 (m, 1 H), 3.7–3.9 (m, 2 H), 4.27 (d, 1 H, J=9 Hz), 4.88 (br exchangeable, 2 H), 5.13 (s, 1 H), 5.85 (m, 2 H), 6.56 (t, 1 H, J=12 Hz), 6.75 (m, 1 H), 6.92 (m, 2 H), 7.19 (s, 1 H), 7.61 (s, 1 H), 9.17 (s, 1 H); mass spectrum m/z 640 (M$^+$); Analysis calculated for $C_{35}H_{45}N_5O_8$.0.5(ethyl acetate): C, 61.48; H, 7.22; N, 10.24%. Found: C, 61.06; H, 7.3; N, 10.32%.

EXAMPLE 27

17-Furfurylamino-17-demethoxygeldanamycin

Mp 122–130° C. (dec); $^1$H-NMR (300 MHz, CDCl$_3$) δ1.09 (overlapping d, 6 H), 1.75 (m, 1 H), 1.79 (s, 3 H), 1.98 (s, 3 H), 2.42 (dd, 1 H, J=7Hz, 6Hz), 2.72 (m, 2 H), 3.28 (s, 3 H), 3.37 (s, 3 H), 3.48 (m, 1 H), 3.59 (m, 1 H), 4.18 (br exchangeable, 1 H), 4.29 (d, 1 H, J=9 Hz), 4.67 (dd, 1 H, J=9 Hz, 5 Hz), 4.73 (dd, 1H, J=9 Hz, 5 Hz), 4.88 (br exchangeable, 2 H), 5.18 (s, 1 H), 5.89 (m, 2 H), 6.28 (m, 1 H), 6.34 (m, 1 H), 6.42 (m, 1 H), 6.57 (t, 1 H, J=12 Hz), 6.94 (d, 1 H, J=12 Hz), 7.28 (s, 1 H), 7.41 (s, 1 H), 9.11 (s, 1 H); mass spectrum m/z 626 (M$^+$); Anailysis calculated for $C_{33}H_{43}N_3O_9$.0.33CHCl$_3$: C, 62.31; H, 6.90; N, 6.54%. Found: C, 62.28; H, 6.78; N, 6.63%.

EXAMPLE 28

17-Tetrahydrofurfurylamino-17-demethoxygeldanamycin

Mp 157–166° C. (dec); $^1$H-NMR (300 MHz, CDCl$_3$) δ1.05 (overlapping d, 6 H), 1.7 (m, 2 H), 1.87 (s, 3 H), 1.9–2.1 (m, 3 H), 2.05 (s, 3 H), 2.38 (m, 1 H), 2.70 (m, 2 H), 3.27 (s, 3 H), 3.34 (s, 3 H), 3.45 (m, 1 H), 3.53 (m, 2 H), 3.82 (m, 1 H), 3.93 (m, 1 H), 4.09 (m, 1 H), 4.27 (d, 1 H, J=8 Hz), 4.88 (br exhangeable, 2 H), 5.18 (s, 1 H), 5.7–6.0 (m, 2 H), 6.56 (m, 2 H), 6.93 (d, 1 H, J=11 Hz), 7.26 (s, 1 H), 9.17 (s, 1 H); mass spectrum m/z 632 (M++2); Analysis calculated for $C_{33}H_{47}N_3O_9$: C, 62.94; H, 7.52; N, 6.69%. Found: C, 62.92; H, 7.57; N, 6.39%.

EXAMPLE 29

17-Tetramethylguanidino-17-demethoxygeldanamycin

Mp 140–145° C. (dec); $^1$H-NMR (300 MHz, CDCl$_3$)δ1.0 (overlapping d, 6 H), 1.70 (m, 1 H), 1.77 (s, 3 H), 2.02 (s, 3 H), 2.51 (m, 2 H), 2.76 (br s, 6 H), 2.83 (s, 6 H), 3.26 (s, 3 H), 3.38 (s, 3 H), 3.42 (m, 1 H), 3.60 (m, 1 H), 4.28 (d, 1 H, J=9 Hz), 5.15 (s, 1 H), 5.83 (t, 1 H, J=7Hz), 5.95 (m, 1 H), 6.57 (t, 1 H, J=12Hz), 6.97 (br d, 1 H, J=12 Hz), 7.07 (s, 1 H), 9.36 (br s, 1 H); mass spectrum m/z 646 (M +2); Analysis calculated for $C_{33}H_{49}N_5O_8$.0.2CHCl$_3$: C, 60.55; H, 7.56; N, 10.64%. Found: C, 60.57; H, 7.67; N, 10.59%.

EXAMPLE 30

17-betα-Alanyl-17-demethoxygeldanamycin

Mp 143–147° C. (dec); $^1$H-NMR (300 MHz, CDCl$_3$) δ0.99 (overlapping d, 6 H), 1.67 (m, 1 H), 1.79 (s, 3 H), 2.03 (s, 3 H), 2.32 (m, 1 H), 2.69 (m, 3 H), 3.22 (s, 3 H), 3.32 (s, 3 H), 3.42 (m, 1 H), 3.55 (m, 1 H), 3.82 (m, 2 H), 4.28 (d, 1 H, J=9), 5.08 (br s, 2 H), 5.19 (s, 1 H), 5.83 (m, 2 H), 6.58 (m, 2 H), 6.91 (d, 1 H, J=12 Hz), 7.25 (s, 1 H), 9.09 (s, 1 H); mass spectrum m/z 640 (M+Na); Ana.lysis calculated for $C_{31}H_{43}N_3O_{10}$.H$_2$O: C, 58.66; H, 6.99; N, 6.62%. Found: C, 58.98; H, 7.03; N, 6.60%.

EXAMPLE 31

17-Homohistamino-17-demethoxygeldanamycin

Mp 128–136° C. (dec); $^1$H-NMR (300 MHz, CDCl$_3$) δ0.87 (d, 3 H, J=7 Hz), 0.98 (d, 3 H, J=7 Hz), 1.7 (m, 3 H), 1.76 (s, 3 H), 1.98 (s, 3 H), 2.12 (m, 4 H), 2.5–2.7 (m, 3 H), 3.21 (s, 3 H), 3.32 (s, 3 H), 3.4–3.55 (m, 4 H), 4.05 (m, 2 H), 4.27 (d, 1 H, J=9 Hz), 4.85 (br exchangeable, 2 H), 5.13 (s, 1 H), 5.85 (m, 2 H), 6.22 (m, 1 H), 6.57 (t, 1 H, J=11 Hz), 6.88 (m, 2 H), 7.08 (s, 1 H), 7.26 (s, 1 H), 7.53 (s, 1 H), 9.09 (s, 1 H); mass spectrum m/z 654 (M +1); Analysis calculated for $C_{34}H_{47}N_5O_8$.0.1CH$_2$Cl$_2$: C, 61.84; H, 7.18; N, 10.57%. Found: C, 61.90; H, 7.49; N, 10.29%.

EXAMPLE 32

17-Amino-22-(4'-fluorophenacyl)-17-demethoxygeldanamycin

17-Amino-17-demethoxygeldanamycin (0.254 g, 0.465 mmol) was dissolved in 5 mL anhydrous dimethyl sulfoxide in flame dried glassware. Potassium t-butoxide (0.054 9, 0.468 mmol) was added and the solution stirred at room temperature under nitrogen for 30 minutes. p-Fluorophenacyl bromide (0.102 g, 0.479 mmol) was added and the solution stirred at room temperature for 1.5 hours. This solution was diluted with ethyl acetate, washed with water and brine, dried over magnesium sulfate, filtered and evaporated in vacuo. The resulting purple residue was flash chromatographed with silica gel eluted with 2% methanol in chloroform to give a purples solid; Yield 0.270 g (66%): mp 183–185° C.(dec); $^1$H-NMR (300 MHz, CDCl$_3$) δ0.61 (br s , J=7 Hz, 3H, 14-CH$_3$), 0.78 (br m, 1 H, H-13), 0.93 (d, J=7 Hz, 3H, 10-CH$_3$), 1.30(s, 3H, 8-CH$_3$), 1.49 (br m, 1H, H-13), 1.82 (dd, J=15 Hz and 4 Hz, 1H, H-15), 1.92 (s, 3H, 2-CH$_3$), 2.02 (br s, 1H, 11-OH), 2.20 (br m, 2H, H-10 and H-14), 2.77 (dd, J=15 Hz and 4 Hz, 1H, H-15), 2.84 (br d, J=10 Hz, 1 H, H-12), 3.23 (s, 3H, OCH$_3$), 3.27 (s, 3H, OCH$_3$), 3.54 (d, J=9 Hz, 1H, H-11), 4.19 (t, J=9 Hz, 1H, H-6), 4.41 (d, J=16 Hz, 1H, α-CH$_2$), 4.95 (d, J=9 Hz, 1H, H-7), 4.97 (s, 2H, NH$_2$), 5.12 (d, J=8 Hz, lH, H-9), 5.20 (t, J=9 Hz, 1 H, H-5), 5.40 (br s, 2H, NH$_2$), 5.84 (s, 1 H, H-19), 5.96 (d, J=17 Hz, 1 H, α-CH$_2$), 6.35 (t, J=10 Hz, 1H, H-4), 7.03 (d, J=13 Hz, 1H, H-3), 7.12 (m, 2H, aromatic), 7.99 (m, 2H, aromatic); m/z 704 (M++Na); IR (KBr, cm$^{-1}$) 1722, 1691, 1675, 1659, 1580, 1504; Anal. for $C_3,H_{44}N_3O_9F$: C, 63.42; H, 6.51; N, 6.16%. Found C, 63.40; H, 6.65; N, 5.84%.

The compounds of Examples 33 to 45 were prepared by thie method of Example from the appropriately substituted phenacyl bromides.

EXAMPLE 33

17-Amino-22-(2',4'-dimethylphenacyl)-17-demethoxygeldanamycin

The residue obtained upon evaporation of the ethyl acetate was purified by Chromatotron (trademark) using 2% methanol in chloroform and again with 1% methanol in chloroform to give fractions containing essentially pure product which were evaporated in vacuo to yield a red solid which was further purified by preparative HPLC using a Zorbax (trademark) column eluted with 54:1:45 ethyl acetate:methanol:hexanes. Fractions containing pure material were evaporated in vacuo then dissolved in a minimum amount of chloroform and precipitated with hexanes to give a dark rose-colored solid; Yield 0.002 gm, (0.6%) mp 154° C. (dec); $^1$H-NMR (300 MHz, CDCl$_3$)δ0.55 (d, J=6 Hz, 3H, 14-CH$_3$), 0.89 (d, J=6 Hz, 3H, 10-CH$_3$), 2.76 (m, 2H, H-10, H-15), 3.04–3.19 (m, 1H, H-12), 3.11 (s, 3H, OCH$_3$), 3.17 (s, 3H, OCH$_3$), 3.47 (m, 1H, H-11), 4.12(t, J=7 Hz, 1H, H-6), 4.21 (d, J=15 Hz, 1H, α-CH), 4.43(br s, 2H, NH$_2$), 4.83 (d, J=7 Hz, 1H, H-7), 4.89–5,07 (m, 2H, NH2), 5.04(d, J=7 Hz, 1H, H-9), 5.10(t, J=7 Hz, 1 H, H-5), 5.71 (d, J=15 Hz, 1 H, α-CH), 5.80(s, 1 H, H-1 9),6.22(t, J=7 Hz, 1H, H-4), 6.81–7.03(m, 3H, H-3, Aromatic), 7.5 (d, J=7 Hz, 1H, Aromatic). m/z 714 (M++Na); IR (KBr, cm$^{-1}$) 1720, 1670, 1655, 1580; Analysis calculated for C$_{38}$H$_{49}$N$_3$O$_9$.0.5H$_2$O:C, 65.12; H, 7.19; N, 6.07%. Found C, 55.3H, 6.89; N, 5.99%.

EXAMPLE 34

17-Amino-22-(2'-methoxyphenacyl)-17-demethoxygeldanamycin

Yield 0.110 g (34%): mp 165–168° C.; $^1$H-NMR (300 MHz, CDCl$_3$)δ0.72 (d, J=7 Hz, 3H, 14-CH$_3$), 0.84 (m, 1H, H-13), 1.03 (d, J=7 Hz, 3H, 10-CH$_3$), 1.40 (s, 3H, 8-CH$_3$), 1.49 (m,1 H, H-13), 1.90 (dd, J=12 Hz and 4 Hz,1 H, H-15), 2.03 (s, 3H, 2-CH$_3$), 2.24 (br m, 2H, H-10 and H-14), 2.41 (s,1H, 11-OH), 2.94 (m, 2H, H-12 and H-15), 3.30 (s, 3H, OCH$_3$), 3.34 (s, 3H, OCH$_3$), 3.62 (d, J=8 Hz, 1H, H-11), 3.97 (s, 3H, OCH$_3$), 4.28 (t, J=10 Hz, 1H, H-6), 4.51 (d, J=19 Hz, 1H, α-CH$_2$), 4.60 (br s, 2H, NH$_2$), 5.02 (d, J=10 Hz, 1 H, H-7), 5.10 (br s, 2H, NH$_2$), 5.20 (d, J=9 Hz, 1 H, H-9), 5.27 (t, J=12 Hz, 1H, H-5), 5.86 (d, J=17 Hz, 1H, α-CH$_2$), 5.98 (s, 1H, H-19), 6.40 (t, J=13 Hz, 1H, H-4), 7.03 (m, 2H, aromatic), 7.14(d, J=12 Hz, 1H, H-3), 7.56 (m, 1H, aromatic), 7.90 (m, 1H, aromatic); m/z 694 (M$^+$); IR (KBr, cm$^{-1}$) 1732, 1678, 1661, 1584.

EXAMPLE 35

17-Amino-22-(3'-methoxyphenacyl)-17-demethoxygeldanamycin

The residue obtained upon evaporation of the ethyl acetate was dissolved in 1 mL chloroform and precipitated with hexanes to give a salmon-colored solid; Yield 151 g (48%): mp 165–168° C.; $^1$H-NMR (300 MHz, CDCl$_3$) δ 0.67 (Cl, J=9 Hz, 3H, 14-H$_3$), 0.78 (m, 1H, H-13), 0.98 (d, J=9 Hz, 3H, 10-CH$_3$),1.32 (s, 3H, 8-CH$_3$), 1.43 (m, 1H, H-13), 1.83 (dd, J=15 Hz and 5 Hz, 1H, H-15), 1.92 (s, 3H, 2-CH$_3$), 2.10–2.27 (br m, 2H, H-10 and H-14), 2.42 (s,1 H, 11-OH), 2.82–2.89 (m, 2H, H-2 and H-15), 3.22 (s, 3H, OCH$_3$), 3.28 (s, 3H, OCH$_3$), 3.58 (d, J=11 Hz, 1H, H-11), 3.81 (s, 3H, OCH$_3$), 4.22 (t, J=10 Hz, 1H, H-6), 4.40 (d, J=18 Hz, 1H, α-CH$_2$), 4.68 (br s, 2H, NH$_2$), 4.99 (d, J=9 Hz, 1 H, H-7), 5.15 (br s, 2H, NH$_2$), 5.16 (d, J=11 Hz, 1 H, H-9), 5.21 (t, J=11 Hz, 1H, H-5), 5.90 (s, 1H, H-19), 5.97 (d, J=17 Hz, 1H, α-CH$_2$), 6.35 (t, J=12 Hz, 1H, H-4), 7.02 (d, J=11 Hz,1 H, H-3), 7.12 (dd, J=8 Hz and 5 Hz,1 H, aromatic), 7.38 (t, J=10 Hz, 1 H, aromatic), 7.42 (d, J=6 Hz, 1 H, aromatic), 7.49 (dd, J=8 Hz and 5 Hz, 1H, aromatic); m/z 716 (M++Na); IR (CH$_2$Cl$_2$, cm$^{-1}$) 1733, 1672, 1661, 1585.

EXAMPLE 36

17-Amino-22-(4'-methoxyphenacyl)-17-demethoxygeldanamycin

The residue obtained upon evaporation of the ethyl acetale was dissolved in 1 mL chloroform and precipitated with hexanes to yield a salmon-colored solid; Yield 0.205 g (64%): mp 175–178° C.; $^1$H-NMR (300 MHz, CDCl$_3$)δ0.65 (d, J=9 Hz, 3H, 14-CH$_3$), 0.76 (m, 1H, H-13), 0.98 (d, J=8 Hz, 3H, 10-CH$_3$), 1.32 (s, 3H, 8-CH$_3$), 1.43 (m, 1H, H-13), 1.82 (dd, J=15 Hz and 5 Hz, 1H, H-15), 1.92 (s, 3H, 2-CH$_3$), 2.10–2.28 (br m, 2H, H-10 and H-14), 2.40 (s,1 H,11 —OH), 2.81–2.89 (m, 2H, H-12 and H-15), 3.22 (s, 3H, OCH$_3$), 3.28 (s, 3H, OCH$_3$), 3.57 (d, J=13 Hz, 1 H, H-11), 3.83 (s, 3H, —OCH$_3$), 4.21 (t, J=11 Hz, 1 H, H-6), 4.36 (d, J=17 Hz, 1 H, α-CH$_2$), 4.67 (br s3, 2H, NH$_2$), 4.98 (d, J=10 Hz, 1H, H-7), 5.11 (br s, 2H, NH$_2$), 5.13 (d, J=12 Hz, 1H, H-9), 5.21 (t, J=12 Hz 1H, H-5), 5.89 (s, 1H, H-19), 5.94 (d, J=18 Hz, 1H, α-CH$_2$), 6.33 (t, J=13 Hz, 1H, H-4), 6.91 (m, 2H, aromatic), 7.08 (d, J=13 Hz, 1H, H-3), 7.89 (m, 2H, aromatic); m/z 691 (M$^+$) and 713 (M++Na); IR (CH$_2$Cl$_2$, cm$^{-1}$) 1732, 1673, 1661, 1586, 1507.

EXAMPLE 37

17-Amino-22-(2'-chlorophenacyl)-17-demethoxygeldanamycin

The residue obtained upon evaporation of the ethyl acetate was purified by preparative centrifugally accelerated radial thin-layer chromatograpohy (ChromatotronR) using a gradient of 2–4% methanol in chloroform to give fractions containing pure product which were evaporated in vacuo to afford a red solid; Yield 0.138 g (43%): $^1$H-NMR (300 MHz, CDCl$_3$)δ0.72 (d, J=7 Hz, 3H, 14-CH$_3$), 0.83 (m, 1H, H-13), 1.03 (d, J=6 Hz, 3H, 1-CH$_3$), 1.40 (s, 3H, 8-CH$_3$), 1.49 (br m,1 H, H-13), 1.91 (dd, J=13 Hz and 6 Hz, 1H, H-15), 1.99 (s, 3H, 2-CH$_3$), 2.18–2.31 (br m, 2H, H-10 and H-14), 2.43 (s, 1 H, 11-OH), 2.38–2.46 (m, 2H, H-12 and H-15), 3.25 (s, 3H, OCH$_3$), 3.33 (s, 3H, OCH$_3$), 3.63 (d, J=8 Hz, 1H, H-11), 4.22 (t, J=10 Hz, 1H, H-6), 4.49 (d, J=19 Hz, 1H, α-CH$_2$), 4.62 (br s, 2H, NH$_2$), 5.02 (d, J=9 Hz, 1 H, H-7), 5.19 (s, 2H, NH$_2$), 5.21 (d, J=12 Hz, 1 H, H-9), 5.30 (t, J=11 Hz, 1 H, H-5), 5.40 (br s, 2H, NH$_2$), 5.83 (d, J=18 Hz, 1H, α-CH$_2$), 6.15 (s, 1H, H-19), 6.39 (t, J=12 Hz, 1H, H-4), 6.96 (d, J=12 Hz, 1H, H-3), 7.38–7.43 (m, 1 H, aromatic), 7.48 (m, 2H, aromatic), 7.67 (m, 1,1, aromatic); m/z 720 (M$^+$+Na); IR (KBr, cm$^{-1}$) 1722, 1680, 1661, 1590; Analysis calculated for. C$_3$,H$_{44}$ClN$_3$O$_9$: C, 61.93; H, 6.35; N, 6.02%. Found C, 60.59; H, 6.18; N, 5.54%.

EXAMPLE 38

17-Amino-22-(4'-chlorophenacyl)-17-demethoxygeldanamycin

The residue obtained upon evaporation of the ethyl acetate was dissolved in 2 mL chloroform and precipitated with hexanes to give a salmon-colored solid; Yield 0.087 g (27%): mp 175–178° C.; $^1$H-NMR (300 MHz, CDCl$_3$)δ0.66 (d, J=7 Hz, 3H, 14-CH$_3$), 0.76 (m, 1H, H-13), 0.98 (d, J=6 Hz, 3H, 10-CH$_3$), 1.33 (s, 3H, 8-CH$_3$), 1.43 (m, lH, H-13), 1.83 (dd, J=15 Hz and 4 Hz, 1H, H-15), 1.95 (s, 3H, 2-CH$_3$), 2.10–2.27 (br m, 2H, H-10 and H-14), 2.41 (s, 1 H, 11-OH), 2.81–2.89 (m, 2H, H-12 and H-15), 3.22 (s, 3H, OCH$_3$), 3.30 (s, 3H, OCH$_3$), 3.58 (d, J=11 Hz, 1 H, H-11), 3.81 (s, 3H, OCH$_3$), 4.21 (t, J=10 Hz, 1H, H-6), 4.36 (d, J=17 Hz, 1H, α-CH$_2$), 4.54 (br s, 2H, NH$_2$), 4.99 (d, J=10 Hz, 1H, H-7), 5.13 (br s, 2H, NH$_2$), 5.15 (d, J=10 Hz, 1H, H-9), 5.22 (t, J=12 Hz 1H, H-5), 5.89 (s, 1H, H-19), 5.97 (d, J=17Hz, 1H, α-CH$_2$), 6 34 (t, J=12Hz, 1H, H-4), 7.01 (d, J=12 Hz, 1H, H-3), 7.43 (d, J=9 Hz, 2H, aromatic), 7.87 (d, J=9 Hz, 2H, aromatic); m/z 720 (M++Na); IR (CH$_2$Cl$_2$, cm$^{-1}$) 1733, 1677, 1662, 1584.

EXAMPLE 39

17-Amino-22-phenacyl-17-demethoxygeldanamycin

The residue obtained upon evaporation of the ethyl acetate was purified by Chromatotron (trademark) using 2% methanol in chloroform to givfa fractions containing pure product which were evaporated in vacuo to yield a red solid. 0.161 gm (53%) mp 188–91° C. (dec); $^1$H-NMR (300 MHz, CDCl$_3$)δ0.68 (d, J=5 Hz, 3H, 14-CH$_3$), 0.80 (m, 1H, H-13), 0.98 (d, J=5 Hz, 3H, 10-CH$_3$), 1.35 (s, 3H, 8-CH$_3$), 1.43 (m, 1H, H-13), 1.85 (dd, J=3 Hz, J=10 Hz, 1H, H-15), 1.96 (s, 3H, 2-CH$_3$), 2.11–2.23 (br m, 2H, H-10, H-14), 2.39 (s, 1H, 11-OH), 2.85 (m, 2H, H-12, H-15), 3.21(s, 3H, OCH$_3$), 3.26 (s, 3H, OCH$_3$), 3.60 (dd, J=3 Hz, J=7 Hz, 1H, H-11), 4.21 (t, J=9 Hz, 1H, H-6), 4.39 (d, J=15 Hz, 1H, α-CH), 4.61 (br s, 2H, NH$_2$), 5.03–5.19 (m, 2H, NH$_2$), 5.16 (d, J=8 Hz, 1H, H-9), 5.71 (t, J=8 Hz, IH, H-5), 5.89 (s, 1H, H-1 9), 6.00 (d, J=15 Hz, 1H, α-CH), 6.35 (t, J=8 Hz, 1H, H-4), 7.05 (d, J=8 Hz, 1H, H-3), 7.46 (t, J=6 Hz, 2H, aromatic), 7.60 (t, J=6 Hz, 1H, aromatic), 7.93 (d, J=6 Hz, 2H, aromatic); m/z 686 (M++Na), 664 (M++H); IR (KBr, cm$^{-1}$) 1720,1670, 1655, 1580; Analysis calculated for C$_{36}$H$_{45}$N$_3$O$_9$.0.5H$_2$O: C, 64.27; H, 6.89; N, 6.27%. Found C, 64.13; H, 6.33; N, 6.19%.

EXAMPLE 40

17-Amino-22-(3',4'-dichlorophenacyl)-17-demethoxygeldanamycin

The residue obtained upon evaporation of the ethyl acetate was further purified by preparative HPLC using a Zorbax column eluted with 593:1:40 ethyl acetate: methanol:hexanes. The fractions containing pure material were evaporated in vacuo then dissolved in a minimum amount of chloroform and precipilated with hexanes to give a dark rose-colored solid; Yield 0.134 g (40%): mp 176–178° C.; $^1$H-NMR (300 MHz, CDCl$_3$)δ0.63 (d, J=7 Hz, 3H, 14-CH$_3$), 0.74 (m, 1H, H-13), 0.98 (d, J=8 Hz, 3H, 10-CH$_3$), 1.31 (s, 3H, 8-CH$_3$), 1.42 (m, 1H, H-13), 1.82 (dd, J=15 Hz and 5 Hz, 1H, H-15), 1.92 (s, 3H, 2-CH$_3$), 2.09–2.24 (br m, 2H, H-10 and H-14), 2.42 (s, 1H, 11-OH), 2.78–2.88 (m, 2H, H-12 and H-15), 3.21 (s, 3H, OCH$_3$), 3.27 (s, 3H, OCH$_3$), 3.57 (d, J=10 Hz, 1H, H-11), 4.18 (t, J=11 Hz, 1H, H-6), 4.36 (d, J=19Hz, 1H, α-CH$_2$), 4.69 (br s, 2H, NH$_2$), 4.98 (d, J=11 Hz, 1H, H-7), 5.12 (d, J=11 Hz, 1H, H-9), 5.16 (br s, 2H, NH$_2$), 5.21 (t, J=11 Hz, 1H, H-5), 5.85 (s, 1H, H-19), 5.92 (d, J=18 Hz, 1H, α-CH$_2$), 6.34 (t, J=12 Hz, 1H, H-4), 6.98 (d, J=12 Hz, 1H, H-3), 7.57 (d, J=9 Hz, 1H, aromatic), 7.76 (dd, J=9 Hz and 4 Hz, 1H, aromatic), 8.01 (d, J=4 Hz, 1H, aromatic); m/z 732 (M$^+$); IR (CH$_2$Cl$_2$, cm$^{-1}$) 1731, 1704, 1673, 1661, 1583.

EXAMPLE 41

17-Amino-22-(4'-aminophenacyl)-17-demethoxygeldanamycin

From 4-aminophenacyl chloride: the product was a pink solid. Yield 0.066 g (21%): mp 188° C. (dec); $^1$H-NMR (300 MHz, CDCl$_3$) 60.71 (d, J=8 Hz, 3H, 14-CH$_3$), 0.86 (br m, 1 H, H-13), 1.04 (d, J=8 Hz, 3H, 10-CH$_3$)δ1.39 (s, 3H, 8-CH$_3$), 1.49 (br m, 1H, H-13), 1.90 (dd, J=13 Hz, 5 Hz, 1H, H-15), 2.00 (s, 3H, 2-CH$_3$), 2.22 (br m, 2H, H-10, H-14), 2.48 (br s,1H, —OH), 2.92 (m, 2H, H-12 and H-15), 3.293 (s, 3H, OCH$_3$), 3.33 (s, 3H, OCH$_3$), 3.62 (d, J=10 Hz, 1H, H-11), 4.28 (s, 2H, NH$_2$), 4.29 (t, J=9 Hz, 1H, H-6), 4.37 (d, J=18 Hz, 1H, α-CH$_2$), 4.75 (br s, 2H, NH$_2$), 5.03 (d, J=9 Hz, 1 H, H-7), 5.18 (br s, 2H, NH$_2$), 5.21 (d, J=9 Hz, 1H, H-9), 5.26 (t, J=13 Hz, 1H, H-5), 5.95 (d, J=18 Hz, 1H, α-CH$_2$), 5.96 (s, 1H, H-19), 6.49 (t, J=10 Hz, 1H, H-4), 6.66 (d, J=9 Hz, 2H, aromatic), 7.18 (d, J=13 Hz, 1H, H-3), 7.78 (d, J=9 Hz, 2H, aromatic); m/z 701 (M$^+$+Na); IR (KBr, cm$^{-1}$) 1718, 1708, 1655, 1619, 1580.

EXAMPLE 42

17-Amino-22-(4'-cyanophenacyl)-17-demethoxygeldanamycin

The residue obtained upon evaporation of the ethyl acetal:e was further purified by preparative HPLC using a Zorbax column eluted with a mixture comprising 59:1:40 ethyl acetate:methanol:hexanes. Fractions containing pure mate(rial were evaporated in vacuo then dissolved in a minimum amount of chloroform and precipitated with hexanes to give a dark rose-colored solid; yield 0.0296 g (8.4%): mp 186° C. (dec); $^1$H-NMR (300 MHz, CDCl$_3$)δ0.71 (d, J=6 Hz, 3H, 14-CH$_3$), 0.83 (br m, 1H, H-13), 1.04 (d, J=6 Hz, 3H, 10-CH$_3$),1.39 (s, 3H, 8-CH$_3$),1.48 (m, 1H, H-13),1.90 (dd, J=11 Hz and 5 Hz,1H, H-15), 1.99 (s, 3H, 2-CH$_3$), 2.25 (br m, 2H, H-10 and H-14), 2.41 (s,1H, —OH), 2.92 (m, 2H, H-12 and H-15), 3.27 (s, 3H, OCH$_3$), 3.34 (s, 3H, OCH$_3$), 3.64 (d, J=11 Hz, 1H, H-11), 4.23 (t, J=10 Hz, 1H, H-6), 4.45 (d, J=18 Hz, 1H, α-CH$_2$), 4.61 (br s, 2H, NH$_2$), 5.05 (d, J=10 Hz, 1H, H-7), 5.20 (br s, 2H, NH$_2$), 5.21 (d, J=11 Hz, 1H, H-9), 5.29 (t, J=11 Hz, 1H, H-5), 5.96 (s, 1H, H-19), 6.02 (d, J=18 Hz, 1H, α-CH$_2$), 6.40 (t, J=11 Hz, 1H, H-4), 7.00 (d, J=11 Hz, 1H, H-3), 7.84 (d, J=8 Hz, 2H, aromatic), 8.08 (d, J=8 Hz, 2H, aromatic); m/z 712 (M$^+$+Na); IR (KBr, cm$^{-1}$) 2220, 1721, 1701, 1672, 1655, 1580; Analysis calculated for C$_{36}$H$_{44}$N$_4$O$_{11}$: C, 64.52; H, 6.44; N, 8.13%. Found C, 58.56; H, 5.81; N, 7.33%.

EXAMPLE 43

17-Amino-22-(2'-nitrophenacyl)-17-demethoxygeldanamycin

Yield 0.0689 g (21%): mp 165° C. (dec); $^1$H-NMR (300 MHz, CDCl$_3$)δ0.70 (d, J=7 Hz, 3H, 14-CH$_3$), 0.82 (m, 1H, H-13), 1.03 (d, J=7 Hz, 3H, 10-CH$_3$), 1.40 (s, 3H, 8-CH$_3$), 1.52 (m, 1H, H-13), 1.90 (dd, J=14 Hz and 4 Hz, 1H, H-15), 2.00 (s, 3H, 2-CH$_3$), 2.08 (s, 1H, 11-OH), 2.26 (br m, 2H, H-10 and H-14), 2.90 (m, 2H, H-12 and H-15), 3.19 (s, 3H, OCH$_3$), 3.33 (s, 3H, OCH$_3$), 3.64 (d, J=10 Hz, 1H, H-11), 4.15 (t, J=10 Hz, 1H, H-6), 4.42 (d, J=18 Hz, 1H, α-CH$_2$), 5.01 (d, J=10 Hz, 1H, H-7), 5.10 (br s, 2H, NH$_2$), 5.20 (d, J=9 Hz, 1H, H-9), 5.23 (br s, 2H, NH$_2$)l, 5.26 (t, J=13 Hz, 1H, H-5), 5.63 (d, J=18 Hz, 1H, α-CH$_2$), 6.38 (t, J=12 Hz, 1H, H-7), 6.52 (s, 1H, H-19), 6.87 (d, J=12 Hz, 1H, H-3), 7.63 (m, 1H, aromatic), 7.69 (m, 1H, aromatic), 7.80 (m, 1H, aromatic), 8.20 (m, 1H, aromatic); m/z 731 (M$^+$+Na); IR (KBr, cm$^{-1}$) 1718, 1671, 1657, 1580, 1521; Analysis calculated for (C$_{36}$H$_{44}$N$_4$O$_{11}$): C, 61.00; H, 6.26; N, 7.91%. Found C, 59.92; H, 6.10; N, 7.71%.

EXAMPLE 44

17-Amino-22-(3'-nitrophenacyl)-17-demethoxygeldanamycin

Yield 0.0225 g (6.9%); $^1$H-NMR (300 MHz, CDCl$_3$)δ0.71 (d, J=8 Hz, 3H, 14-CH$_3$), 0.88 (m, 1H, H-13), 1.04 (d, J=8 Hz, 3H, 10-CH$_3$), 1.34 (s, 3H, 8-CH$_3$), 1.42 (m, 1H, H-13), 1.90 (dd, J=13 Hz and 5 Hz, 1H, H-15), 2.00 (s, 3H, 2-CH$_3$), 2.25 (br m, 2H, H-10 and H-14), 2.42 (br s, 1H, —OH), 2.93 (m, 2H, H-12 and H-15), 3.29 (s, 3H, OCH$_3$), 3.34 (s, 3H, OCH$_3$), 3.64 (d, J=10 Hz, 1H, H-11), 4.23 (t, J=9 Hz, 1H, H-6), 4.52 (d, J=18 Hz, 1H, α-CH$_2$), 4.62 (br s, 2H, NH$_2$), 5.06 (d, J=9 Hz, 1H, H-7), 5.15 (br s, 2H, NH$_2$), 5.21 (d, J=9 Hz, 1H, H-9), 5.30 (t, J=13 Hz, 1H, H-5), 5.98 (s, 1H, H-19), 6.06 (d, J=18 Hz, 1H, α-CH$_2$), 6.41 (t, J=9 Hz, 1H, H-4), 7.00 (d, J=13 Hz, 1H, H-3), 7.76 (t, J=8 Hz, 1H, aromatic), 8.32 (d, J=8 Hz, 1H, aromatic), 8.52 (d, J=8 Hz, 1H, aromatic), 8.83 (s, 1H, aromatic); m/z 731 (M$^+$+Na); IR (KBr, cm$^{-1}$) 1719, 1664, 1652, 1580, 1521.

EXAMPLE 45

17-Amino-22-(4'-nitrophenacyl)-17-demethoxygeldanamycin

The residue obtained upon evaporation of the ethyl acetate was further purified by preparative HPLC using a Zorbax column eluted with 59:1:40 ethyl acetate:methanol:hexanes. Fractions containing pure material were evaporated in vacuo then dissolved in a minimum amount of chloroform and precipitated with hexanes to give a dark rose-colored solid; Yield 0.0175 g (1.3%): mp; $^1$H-NMR (300 MHz, CDCl$_3$)δ0.70 (d, J=7 Hz, 3H, 14-CH$_3$), 0.82 (m, 1H, H-13), 1.02 (d, J=7 Hz, 3H, 10-CH$_3$), 1.38 (s, 3H, 8-CH$_3$), 1.50 (m, 1 H, H-13), 1.90 (dd, J=16 Hz and 4 Hz, 1 H, H-15), 2.00 (s, 3H, 2-CH$_3$), 2.25 (br m, 2H, H-10 and H-14), 2.50 (br s, 1H, 11-OH), 2.89 (m, 2H, H-12 and H-15), 3.27 (s, 3H, OCH$_3$), 3.33 (s, 3H, OCH$_3$), 3.63 (d, J=10 Hz, 1H, H-11), 4.23 (t, J=10 Hz, 1H, H-6), 4.50 (d, J=18 Hz, 1H, α-CH$_2$), 4.77 (s, 2H, NH$_2$), 5.03 (d, J=10 Hz, 1H, H-7), 5.20 (d, J=11 Hz, 1H, H-9), 5.25 (br s, 2H, NH$_2$), 5.28 (t, J=11 Hz, 1H, H-5), 5.96 (s, 1H, H-19), 6.03 (d, J=18 Hz, 1H, α-CH$_2$), 6.40 (t, J=12 Hz, 1H, H-4), 6.99 (d, J=12 Hz, 1H, H-3), 8.15 (d, J=9 Hz, 2H, aromatic), 8.37 (d, J=9 Hz, 1H, aromatic); m/z 731 (M$^+$+Na); IR (KBr, cm$^{-1}$) 1660, 1590.

EXAMPLE 46

17-Amino-22-(4'-azidophenacyl)-17-demethoxygeldanamycin

17-Amino-17-demethoxygeldanamycin (0.500 g, 0.92 mmol) was dissolved in 25 mL of acetone (stored over potassium carbonate) and 1.27 g potassium carbonate was added (9.17 mmol, 10 eq). The reaction was stirred in the dark for 24 hours, filtered, concentrated in vacuo to a residue which was flash chromatographed through silica gel using 69:1:30 ethyl acetate:methanol:hexanes. The product was dissolved in 1 mL chloroform and precipitated with hexanes to give a rose-colored solid; Yield 0.095 g (15%): mp 165–167° C.; $^1$H-NMR (300 MHz, CDCl$_3$)δ0.65 (d, J=8 Hz, 3H, 14-CH$_3$), 0.76 (m, 1H, H-13), 0.97 (d, J=8 Hz, 3H, 10-CH$_3$), 1.32 (s, 3H, 8-CH$_3$), 1.42 (m, 1H, H-13), 1.82 (dd, J=15 Hz and 5 Hz, 1H, H-15), 1.91 (s, 3H, 2-CH$_3$), 2.09–2.27 (br m, 2H, H-10 and H-14), 2.41 (br s, 1H, 11-OH), 2.79–2.90 (m, 2H, H-12 and H-15), 3.21 (s, 3H, OCH$_3$), 3.27 (s, 3H, OCH$_3$), 3.58 (d, J=11 Hz, 1H, H-11), 4.20 (t, J=10 Hz, 1H, H-6), 4.36 (d, J=17 Hz, 1H, α-CH$_2$), 4.65 (br s, 2H, NH$_2$), 4.98 (d, J=10 Hz,1H, H-7), 5.11 (br s, 2H, NH$_2$), 5.14 (d, J=10 Hz, 1H, H-9), 5.20 (t, J=12 Hz, 1H, H-5), 5.89 (s, 1H, H-19), 5.95 (d, J=17 Hz, 1H, α-CH), 6.33 (t, J=13 Hz, 1H, H-4), 7.02 (d, J=13 Hz, 1H, H-3), 7.08 (d, J=9 Hz, 2H, aromatic), 7.91 (d, J=9 Hz, 2H, aromatic); m/z 705 (M$^+$+H); Analysis calculated for C$_{36}$H$_{44}$N$_6$O$_9$.0.2H$_2$O: C, 58.37; H, 6.53; N, 11.34%; Found C, 58.37:, H, 5.85;N, 11.08%.

EXAMPLE 47

17-Amino-22-(4'-amino-3'-iodophenacyl)-17-demethoxygeldanamycin

Potassium chloride (0.022 g, 0.29 mmol) was dissolved in 1 mL water and poured into iodine monochloride (0.043 g, 0.27 mmol). This mixture was poured into a solution of the title compound of Example 41 (0.139 g, 0.2 mmol) in 24 mL 0.1N hydrochloric acid and 3 mL methanol. After stirring for 2 hours at room temperature the reaction was quenched with sodium bisulfite. The reaction mixture was extracted with ethyl acetate. The organic layer was washed with 3N hydrochloric acid, saturated sodium bicarbonate, water and brine, dried over magnesium sullate and filtered. The residue obtained upon removal of the solvent was dissolved in 1 mL chloroform and precipitated with hexanes to give a salmon-colored solid; Yield 0.099 g (60%): $^1$H-NMR (300 MHz, CDCl$_3$)δ0.66 (d, J=7 Hz, 3H, -CH$_3$), 0.75 (m, 1H, H-13), 0.98 (d, J=6 Hz, 3H, 10-CH$_3$), 1.34 (s, 3H, 8-CH$_3$), 1.47 (m, 1H, H-13), 1.91 (m, 1H, H-15), 1.95 (s, 3H, 2-CH$_3$), 2.10–2.29 (br m, 2H, H-10 and H-14), 2.59 (s,1 H, 11-OH), 2.78–2.92 (m, 2H, H-12 and H-15), 3.25 (s, 3H, OCH$_3$), 3.29 (s, 3H, OCH$_3$), 3.59 (d, J=10 Hz, 1H, H-11), 4.24 (t, J=10 Hz, 1H, H-6), 4.32 (d, J=18 Hz, 1H, α-CH$_2$), 4.56 (s, 2H, NH$_2$), 4.95 (d, J=10 Hz, 1H, H-7), 5.04 (br s, 2H, NH$_2$), 5.15 (d, J=11 Hz, 1H, H-9), 5.22 (t, J=11 Hz, 1 H, H-5), 5.58 (br s, 2H, NH$_2$), 5.88 (d, J=18 Hz, 1 H, α-CH$_2$), 5.89 (s, 1H, H-19), 6.37 (t, J=12 Hz, 1H, H-4), 6.60 (dd, J=9 Hz and 3 Hz, 1H, aromatic), 7.06 (d, J=12 Hz, 1H, H-3), 7.71 (dd, J=9 Hz and 2 Hz, 1H, aromatic), 8.22 (dd, J=2 Hz and 3 Hz, 1H, aromatic) IR (KBr, cm$^{-1}$) 1715, 1660, 1610, 1580.

The acid washes were neutralized with sodium bicarbonate and extracted with ethyl acetate. The ethyl acetate extracts were washed with water and brine, dried over magnesium sulfate, filtered and stripped to recover the title compound of Example 41, Yield 0.045 g (27%).

EXAMPLE 48

17-Amino-22-(4'-azido-3'-iodophenacyl)-17-demethoxygeldanamycin

17-Amino-22-(4'-amino-3'-iodophenacyl)-17-demethoxygeldanamycin, from Example 47, (0.036 g, 0.44 mmol) was dissolved in 89 mL methanol, cooled to 0° C. and shielded from light. To this solution was added 45 mL 1N hydrochloric acid and 45 mL 0.5N sodium nitrite. After 15 minutes of stirring, an additional 45 ml 0.5N sodium azide was added and the reaction mixture stirred another 15 minutes at 0° C. The resulting solution was extracted with ethyl acetate. The ethyl acetate extracts were washed with water and brine, dried over magnesium sulfate, filtered and stripped to give a red glass which was dissolved in 1 mL ethyl acetate and precipitated with hexanes. Yield 0.027 g (72%): $^1$H-NMR (300 MHz, CDCl$_3$)δ0.69 (d, J=7 Hz, 3H, 14-CH$_3$), 0.79 (m, 1 H, H-13), 1.03 (d, J=8 Hz, 3H, 10-CH$_3$), 1.50 (s, 3H, 8-CH$_3$), 1.89 (m, 2H, H-13 and H-15), 1.99 (s, 3H, 2-CH$_3$), 2.11–2.32 (br m, 2H, H-10 and H-14), 2.53 (br s, 1 H, 11-OH), 2.81 -2.95 (m, 2H, H-12 and H-15), 3.28 (s, 3H, OCH$_3$), 3.32 (s, 3H, OCH$_3$), 3.62 (d, J=9 Hz, 1H, H-11), 4.22 (t, J=12 Hz, 1H, H-6), 4.41 (d, J=17 Hz, 1H, α-CH$_2$), 4.80 (br s, 2H, NH$_2$), 5.02 (d, J=9 Hz, 1H, H-7), 5.16–5.31 (br m, 4H, NH$_2$, H-9, and H-5), 5.92 (s, 1H, H-19), 5.99 (d, J=18 Hz, 1H, α-CH$_2$), 6.40 (t, J=14 Hz, 1H, H-4), 7.03 (d, J=14 Hz, 1H, H-3), 7.12 (m, 1H, aromatic), 8.00 (m, 2H, aromatic), 8.40 (m, 1H, aromatic); IR (KBr, cm$^{-1}$) 1722, 1680, 1661, 1580.

The compounds of Examples 49 and 50 were prepared according to the method of Example 32.

EXAMPLE 49

17-Amino-22-(4'-phenylphenacyl)-17-demethoxygeldanamycin

Yield 0.119g (35%): mp 193–195° C. (dec); $^1$H-NMR (300 MHz, CDCl$_3$)δ0.72 (d, J=7 Hz, 3H, 14-CH$_3$), 0.83 (m, 1 H, H-13), 1.04 (d, J=7 Hz, 3H, 10-CH₃), 1.40 (s, 3H, 8-CH₃), 1.49 (m, 1H, H-13), 1.90 (dd, J=16 Hz and 5 Hz, 1H, H-15), 2.00 (s, 3H, 2-H₃), 2.25 (br m, 2H, H-10 and H-14), 2.47 (s,1 H, 11-OH), 2.91 (m, 2H, H-12 and H-15), 3.31 (s, 3H, OCH₃), 3.33 (s, 3H, OCH₃), 3.64 (d, J=10 Hz, 1H, H-11), 4.29 (t, J=10 Hz, 1H, H-6), 4.49 (d, J=18 Hz, 1H, α-CH₂), 4.72 (br s, 2H, NH₂), 5.04 (d, J=10 Hz, 1H, H-7), 5.17 (br s, 2H, NH₂), 5.21 (d, J=11 Hz, 1H, H-9), 5.28 (t, J=11 Hz, 1H, H-5), 5.99 (s, 1H, H-19), 6.09 (d, J=18 Hz, 1H, α-CH₂), 6.41 (t, J=12 Hz, 1H, H-4), 7.13 (d, J=12 Hz, 1H, H-3), 7.47 (m, 3H, aromatic), 7.12 (m, 3H, aromatic), 7.74 (d, J=8 Hz, 2H, aromatic), 8.05 (d, J=8 Hz, 2H, aromatic); m/z 731 (M⁺+Na⁺).

EXAMPLE 50

17-Amino-22-(2-acetonaphthyl)-17-demethoxygeldanamycin

The crude title compound, prepared from 2-(2'-bromoacetyl)naphthalene was dissolved in 1 mL chloroform and precipitated with hexanes to give a salmon-colored solid; Yield 0.163 g (50%): mp 185–187° C.; ¹H-NMR (300 MHz, (CDCl₃)δ0.71 (d, J=8 Hz, 3H, 14-CH₃), 0.82 (m, 1H, H-13), 1.02 (d, J=7 Hz, 3H, 10-CH₃), 1.40 (s, 3H, 8-CH₃), 1.49 (m, 1H, H-13), 1.89 (dd, J=15 Hz and 5 Hz, 1H, H-15), 2.00 (s, 3H, 2-CH₃), 2.22 (br m, 2H, H-10 and H-14), 2.44 (s,1H, 11-OH), 2.91 (m, 2H, H-12 and H-15), 3.30 (s, 3H, OCH₃), 3.33 (s, 3H, OCH₃), 3.51 (d, J=11 Hz, 1H, H-11), 4.30 (t, J=11 Hz, 1H, H-6), 4.59 (d, J=19 Hz, 1H, α-CH₂), 4.68 (br s, 2H, NH₂), 5.02 (d, J=10 Hz, 1H, H-7), 5.15 (br s, 2H, NH₂), 5.20 (d, J=13 Hz, 1H, H-9), 5.28 (t, J=13 Hz, 1H, H-5), 6.00 (s, 1H, H-19), 6.20 (d, J=17 Hz, 1H, α-CH₂), 6.40 (t, J=12 Hz, 1H, H-4), 7.13 (d, J=13 Hz,1H, H-3), 7.54–7.68 (m, 2H, aromatic), 7.87–8.02 (m, 2H, aromatic), 8.51 (s, 1H, aromatic); m/z 714 (M⁺) and 736 (M++Na); IR (CH₂Cl₂, cm⁻¹) 1733,1677, 1662, 1585.

EXAMPLE 51

17-Azetidin-1-yl-11-α-fluoro-17-demethoxygeldanamycin

17-Azetidin-1-yl-17-demethoxygeldanamycin, the title compound of Example 18, (0.200 g, 0.342 mmol) was added to a flame dried flask under nitrogen and dissolved in 15 mL of methylene chloride. The mixture was cooled to –68° C. with an external dry ice/acetone bath and then a solution of DAST (0.055g, 0.342 mmol, 0.045 mL) in 2.5 mL of methylene chloride was added dropwise. After 1 hour 5 mL of 5% aqueous NaHCO₃ was addded slowly and the product extracted into 100 mL of methylene chloride. The organic layer was washed with 3×50 mL of water and 2×50 mL of brine, dried with MgSO₄, filtered and stripped of solvent to afford a purple solid. This was purified by flash column chromatography using 5% methanol in chloroform. Material of Rf=0.42 (1:9 methanol: chloroform), the desired product, (0.058 g 29%) was disolved in a minimal amount of ethyl acetate and precipitated with hexanes; Yield 0.042 g (21%), mp 128° C. (dec); ¹H-NMR (300 MHz, CDCl₃) δ1.05(m, 6H: 10-CH₃ and 14-CH₃), 1.25 (br t, J=15 Hz, 1H, H-13), 1.55 (br t, J=15 Hz, 1H, H-13), 1.78 (s, 3H, 8-CH₃), 1.96 (br m, 1H, H-14), 2.03 (s, 3H, 2-CH₃), 2.23 (dd, J=8.5 Hz, 16 Hz, 1H, H-15), 2.40 (br m, 2H, 3' azetidine CH₂), 2.55 (dd, J=7 Hz, 16 Hz, 1H, H-15), 2.80 (br d, J=26 Hz, 1H, H-10), 3.35 (s, 3H, OCH₃), 3.37 (s, 3H, OCH₃), 3.53 (br m, 1H, H-12), 4.39 (d, J=9 Hz, 1H, H-6), 4.0 (br m, 7H, NH₂ and 2' and 4' azetidine CH₂ and H-11), 5.60 (d, J=9Hz, 1H, H-9), 5.70(s, 1H, H-7), 5.88 (t, J=9 Hz, 1H, H-5), 6.55 (t, J=9Hz, 1H, H-4), 6.96 (d, J=9 Hz, 1H, H-3), 7.05 (s, 1H, H-19), 9.33 (s, 1H, NH-22); m/z 610. (M++Na); IR (KBr, cm⁻¹) 1735,1690, 1650; Analysis calculated for C₃₁H₄₂FN₃O₇.5H₂O: C, 54.93; H, 7.73; N, 6.20%. Found: C, 55.07; H, 6.23; N, 6.07%.

The compounds of Examples 52–58 were prepared by ttle method of Example 51 from the appropriately substituted 17-amino-17-demethoxygelcdanamycin derivatives.

EXAMPLE 52

17-Amino-11-α-fluoro-17-demethoxygeldanamycin

Yield 0.155 g (44%), mp >250° C. (dec); ¹H-NMR (300 MHz, CDCl₃)δ0.80 (d, 3H, J=8Hz, 10-CH₃), 0.90 (d, 3H, J=8Hz, 14-CH₃), 0.93 (br m, 1H, H-13), 1.35 (br t, 1H, H-13), 1.60 (s, 3H, 8-CH₃), 1.85 (s, 3H, 2-CH₃), 1.85 (br m, 1H, H-14), 1.85–2.1 (br m, 2H, H-15), 2.63 (br d, J=26 Hz, 1H, H-10), 3.16 (s, 6H, OCH₃), 3.26 (br m, 1H, H-12), 4.28 (d, J=9Hz, 1H, H-6), 4.45 (br d, J=47 Hz, 1H, H-11), 4.60 (br m, 2H, NH₂), 4.95 (s, 1H, H-7), 5.07 (br s, 2H, NH₂), 5.45 (d, J=9 Hz, 1H, FH-9), 5.70 (t, J=9 Hz, 1H, H-5), 6.35 (t, J=9 Hz, 1H, H-4), 6.80 (d, J=9 Hz, 1H, H-3), 7.05 (s, 1H, H-19), 9.0 (s, 1H, NH-22); m/z 570. (M++Na); IR (KBr, cm⁻¹) 1715, 1685, 1670; Analysis calculated for C₂₈H₃₈FN₃O₇.0.25H₂O: C, 60.91; H, 7.03; N, 7.61%. Found: C, 60.78; H, 6.87; N, 7.43%.

EXAMPLE 53

17-Isopropylamino-11-α-fluoro-17-demethoxygeldanamycin

Yield 0.035 g (16%), mp 132° C.; ¹H-NMR (300 MHz, CDCl₃)δ0.85 (m, 6H, 10-CH₃, 14-CH₃), 0.85 (m, 1H, H-13), 1.07 and 1.11 (br d, J=8 Hz, 6H, isopropyl CH₃), 1.38 (br m, 1H, H-13), 1.60 (s, 3H, 8-CH₃), 1.71 (br m, 1H, H-14), 1.75 (s, 3H, 2-CH₃), 2.15 (dd, J=8.5 Hz, 16 Hz, 1H, H-15), 2.45 (dd, J=7 Hz, 16 Hz, 1H, H-15), 2.65 (br d, J=26 Hz, 1H, H-10), 3.19 and 3.20 (br s, 6H, OCH₃), 3.35 br m, 1H, H-1 2), 3.95 (m, 1H, isopropyl CH), 4.22 (d, J=9 Hz, 1H, H-6), 4.30 (br d, J=47 Hz, 1H, H-11), 4.65 (br m, 2H, NH₂), 5.04 (s, 1H, H-7), 5.46 (d, J=9 Hz, 1H, H.9), 5.73 (t, J=9 Hz, 1H, H-5), 5.94 (br d, J=10.5 Hz, 1H, NH), 6.40 (t, J=9Hz, 1 H-4), 6.80 (d, J=9 Hz, 1H, H-3), 7.05 (s, 1H, H-19), 9.15 (s, 1H, NH-22); m/z 612. (M++Na); IR (KBr, cm⁻¹) 1740, 1705, 1655; Analysis calculated for C₃₁H₄₄FN₃O₇.0.5H₂O: C, 62.19; H,7.57; N, 7.01%. Found: C, 62.36; H, 7.48; N, 6.81%.

EXAMPLE 54

17-Cyclopropylamino-11-α-fluoro-17-demethoxygeldanamycin

Yield 0.056 g (25%), mp 119° C. (dec); ¹H-NMR (300 MHz, CDCl₃)δ0.70 (m, 2H, cyclopropyl CH₂), 0.86 (m, 3H, cyclopropyl CH₂ and H-13), 0.92 (d, 3H, J=8Hz, 10-CH₃), 1.00 (d, 3H, J=8Hz, 14-CH₃), 1.53 (br m, 1H, H-13), 1.70 (s, 3H, 8-CH₃), 1.95 (s, 3H, 2-CH₃), 2.00 (br m, 1H, H-14), 2.62 (dd, J=8.5 Hz, 16 Hz, 1H, H-15), 2.70 (br d, J=26 Hz, 1H, H-10), 2.80 (m, 1H, cyclopropyl CH), 2.90 (dd, J=7 Hz, 16 Hz, 1H, H-15), 3.33 (s, 6H, OCH₃), 3.45 (br m, 1H, H-12), 4.33 (d, J=9 Hz, 1H, H-6), 4.36 (br d, J=47 Hz, 1H, H-11), 4.7 (br m, 2H, NH₂), 5.10 (s, 1H, H-7), 5.55 (d, J=9 Hz, 1H, H-9), 5.75 (t, J=9 Hz, 1H, H-5), 6.20 (br t, 1H, NH), 6.46 (t, J=9 Hz, 1H, H-4), 6.90 (d, J=9 Hz, 1H, H-3), 7.15 (s, 1H, H-19), 9.15 (s, 1H, NH-22); m/z 610. (M++Na); IR (KBr, cm⁻¹) 1740, 1690, 1630; Analysis calculated for $C_{31}H_{42}FN_3O_7 \cdot 1.5H_2O$: C, 60.57; H, 7.37; N, 6.83%. Found: C, 60.43; H, 6.79; N, 6.83%.

EXAMPLE 55

17-Allylamino-11-α-fluoro-17-demethoxygeldanamycin

Yield 0.049 g (25%), mp 110–112° C.; $^1$H-NMR (300 MHz, CDCl$_3$)δ0.85(d, 3H, J=8Hz, 10-CH$_3$), 0.88(d, 3H, J=8Hz, 14-CH$_3$), 1.45 (br m, 2H, H-13), 1.63 (s, 3H, 8-CH$_3$), 1.86 (s, 3H, 2-CH$_3$), 1.88 (br m, 1H, H-14), 2.20 (dd, J=8.5 Hz, 16 Hz, 1H, H-15), 2.55 (dd, J=7 Hz, 16 Hz, 1H, H-15), 2.80 (br d, J=26 Hz, 1H, H-10), 3.20 (s, 6H, OCH$_3$), 3.33 (br m, 1H, H-12), 3.95 (br t, 2H, allylic CH$_2$), 4.23 (d, J=9 Hz, 1 H, H-6), 4.26 (br d, J=49 Hz, 1H, H-11), 4.57 (br m, 2H, NH$_2$), 5.03 (s, 1 H, H-7), 5.15 (br d, 2H, vinylic CH$_2$), 5.45 (d, J=9 Hz, 1H, H-9), 5.55 (m, 2H, H-5 and vinylic CH), 6.10 (br t, 1H, NH), 6.40 (t, J=9 Hz, 1H, H-4), 6.80 (d, J=9 Hz, 1H, H-3), 7.07 (s, 1H, H-19), 9.13 (s, 1H, NH-22); m/z 608. (M++Na); IR (KBr, cm$^{-1}$) 1740, 1700, 1655; Analysis calculated for $C_{31}H_{42}FN_3O_7 \cdot 0.75H_2O$: C, 61.93; H, 7.24; N, 6.98%. Found: C, 61.87; H, 6.93; N, 7.00%.

EXAMPLE 56

17-Propargylamino-11-α-fluoro-17-demethoxygeldanamycin

Yield 0.051 g (27%), mp 111° C. (dec); $^1$H-NMR (300 MHz, CDCl$_3$)δ0.83 (br m, 1H, H-13), 0.95 (d, 3H, J=8Hz, 10-CH$_3$), 0.98 (d, 3H, J=8Hz, 14-CH$_3$), 1.53 (br m, 1H, H-13), 1.73 (s, 3H, 8-CH$_3$), 1.95 (s, 3H, 2-CH$_3$), 1.94 (br m, 1H, H-14), 2.35 (s, 1H, acetylene CH), 2.35 (dd, J=8.5 Hz, 16 Hz, 1 H, H-15), 2.58 (dd, J=7 Hz, 16 Hz, 1 H, H-15), 2.65 (br d, J=26 Hz, 1H, H-10), 3.3 (s, 6H, OCH$_3$), 3.45 br m, 1H, H-12), 4.20 (br s 2H, propargyl CH$_2$), 4.33 (d, J=9 Hz, 1H, H-6), 4.36 (br d, J=47 Hz, 1H, H-11), 4.8 (br m, 2H, NH$_2$), 5.13 (s, 1H, H-7), 5.57 (d, J=9 Hz, 1H, H-9), 5.85 (t, J=9 Hz, 1H, H-5), 6.13 (br t, 1H, NH), 6.50 (t, J=9 Hz, lH, H-4), 6.90 (d, J=9 Hz, 1H, H-3), 7.20 (s, 1H, H-19), 9.13 (s, 1H, NH-22); m/z 608. (M++Na); IR (KBr, cm$^{-1}$) 2120, 1735, 1695,1635; Analysis calculated for $C_3,H_{40}FN_3O_7 \cdot 0.75H_2O$: C, 62.14; H, 6.98; N, 7.01%. Found: C, 61.99; H, 6.71; N, 6.90%.

EXAMPLE 57

17-(2'-Cyanoethylamino)-11-α-fluoro-17-demethoxygeldanamycin

Yield 0.026 g (14%), mp 122–24° C. (dec); $^1$H-NMR (300 MHz, CDCl$_3$)δ1.15 (br m, 1H, H-13), 1.12 (d, 3H, J=8Hz, 10-CH$_3$), 1.17 (d, 3H, J=8Hz, 14-CH$_3$), 1.65 (br t, 1H, H-13), 1.75 (s, 3H, 8-CH$_3$), 1.90 (s, 3H, 2-CH$_3$), 2.1 (br m, 1H, H-14), 2.40 (dd, J=8.5 Hz, 16Hz, 1H, H-15), 2.65 (dd, J=7Hz, 16 Hz, 1H, H-15), 2.83 (t, J=8Hz, 2H, β-ethyl CH$_2$), 2.93 (br d, J=26 Hz, 1H, H-10), 3.46 (s, 6H, OCH$_3$), 3.45 (br m, 1H, H-12), 3.56 (q, J=8Hz, 2H, α-ethyl CH$_2$), 4.46 (d, J=9 Hz, 1H, H-6), 4.55 (br d, J=47 Hz, 1H, H-11), 4.85 (br m, 2H, NH$_2$), 5.26 (s, 1H, H-7), 5.73 (d, J=9 Hz, 1H, H-9), 6.00 (t, J=9 Hz, 1H, H-5), 6.07 (br t, 1H, NH), 6.65 (t, J=9 Hz, 1H, H-4), 7.07 (d, J=9 Hz, 1H, H-3), 7.35 (s, 1H, H-19), 9.25 (s, 1H, NH-22); m/z 623. (M++Na); IR (KBr, cm$^{-1}$) 2350, 1730, 1695, 1630; Analysis calculated for $C_{31}H_{41}FN_4O_7$: C, 61.99; H, 6.88; N, 9.33%. Found: C, 61.52; H, 6.91; N, 9.25%.

EXAMPLE 58

17-(2'-Fluoroethylamino)-11-α-fluoro-17-demethoxygeldanamycin

Yield 0.064 g (32%), mp 134° C. (dec); $^1$H-NMR (300 MHz CDCl$_3$)δ1.05 (br m, 1H, H-13), 1.03 (d, 3H, J=8Hz, 10-CH$_3$), 1.07 (d, 3H, J=8 Hz, 14-CH$_3$), 1.57 (br t, 1H, H-13), 1.77 (s, 3H, 8-CH$_3$), 2.0 (br m, 1H, H-14), 2.05 (s, 3H, 2-CH$_3$), 2.35 (dd, J=8.5 Hz, 16 Hz, 1H, H-15), 2.63 (dd, J=7 Hz, 16 Hz, 1H, H-15), 2.83 (br d, J=26 Hz, 1H, H-10), 3.4 (s, 6H, OCH$_3$), 3.53 (br m, 1H, H-12), 3.85 (two br d m, J=27 Hz, 2H, α-ethyl CH$_2$), 4.4 (d, J=9Hz, 1H, H-6), 4.45 (br d, J=47Hz, 1H, H-11), 4.65 (two br d t, J=46 Hz 7 Hz, 2H, β-ethyl CH$_2$), 4.75 (br m, 2H, NH$_2$), 5.23 (s, 1H, H-7), 5.63 (d, J=9 Hz, 1H, H-9), 5.90 (t, J=9 Hz, 1H, H-5), 6.25 (br t, 1H, NH), 6.57 (t, J=9 Hz, 1H, H-4), 6.97 (d, J=9 Hz, 1H, H-3), 7.25 (s, 1H, H-19), 9.25 (s, 1H, NH-22); m/z 596. (M++Na); IR (KBr, cm$^{-1}$) 1740, 1700, 1630; Analysis calculated for $C_{30}H_{41}F_2N_3O_7$: C, 60.69; H, 6.96; N, 7.07%. Found: C, 60.23; H, 6.99; N, 7.02%.

EXAMPLE 59

11-α-Fluoro-geldanamycin

The title compound was prepared from geldanamycin by the method of Example 51; Yield 0.064 g (32%), mp 232° C. (dec); $^1$H-NMR (300 MHz, (CD$_3$)δ0.87 (d, 3H, J=8Hz, 10-CH$_3$), 1.00 (d, 3H, J=8Hz, 14-CH$_3$), 1.0 (br m, 1H, H-13), 1.4 (br t, 1H, H-13), 1.73 (s, 3H, 8-CH$_3$), 1.95 (s, 3H, 2-CH$_3$), 1.9 (br m, 1H, H-14), 2.25 (dd, 1H, J=7 Hz, 16 Hz, 1H, H-15), 2.45 (dd, J=8.5 Hz, 16 Hz, 1H, H-15), 2.75 (br d, J=26 Hz, 1H, H-10), 3.3 (s, 3H, OCH$_3$), 3.34 (s, 3H, OCH$_3$), 3.4 (br m, 1H, H-12), 4.05 (s, 3H, 17-OCH$_3$), 4.27 (d, J=9 Hz, 1H, H-6), 4.57 (br d, J=47 Hz, 1H, H-11), 4.7 (br m, 2H, NH$_2$), 5.05 (s, 1H, H-7), 5.53 (d, J=9 Hz, 1H, H-9), 5.85 (t, J=9 Hz, 1H, H-5), 6.50 (t, J=9 Hz, 1H, H-4), 6.85 (d, J=9 Hz, 1H, H-3), 7.20 (s, 1H, H-19), 8.65 (s, 1H, NH-22); m/z 585. (M++Na); IR (KBr, cm$^{-1}$) 1740, 1705, 1655; Analysis calculated for $C_{29}H_{39}FN_2O_8 \cdot 0.25H_2O$: C, 61.41; H, 7.02; N, 4.93%. Found: C, 61.03; H, 6.65; N, 4.92%.

EXAMPLE 60

17-(S)-2'-Hydroxypropylamino-11-α-fluoro-17-demethoxygeldanamycin

The title compound of Example 59 (0.307 g, 0.546 mmol, was slurried in 6 mL of chloroform and treated with (S)-2-hydroxypropylamine (0.205 9, 2.73 mmol) at 22° C. for 16 hours. The reaction mixture was diluted with 50 mL of chloroform and washed with 3×50 mL of brine and 3×50 mL of water. The organic layer was dried with MgSO$_4$, filtered and vacuum evaporated to a purple solid. Flash column chromatography on silica gel eluted with 3% methanol in chlcroform afforded pure product; Yield 0.070 g (21%), mp 119° C. (dec); $^1$H-NMR (300 MHz, CDCl$_3$)δ0.95 (br t, 7H, H-13 and 10-CH$_3$ and γ-propyl CH$_3$), 1.25 (d, 3H, J=8Hz, 14-CH$_3$), 1.50 (br t, 1H, H-13), 1.70 (s, 3H, 8-CH$_3$), 1.9 (br m, 1H, H-14), 1.97 (s, 3H, 2-CH$_3$), 2.33 (dd, J=8.5 Hz, 16 Hz, 1H, H-15), 2.53 (dd, J=7 Hz, 16 Hz, 1H, H-15), 2.75 (br d, J=26 Hz, 1H, H-10), 3.30 (s, 6H, OCH$_3$), 3.30 (m, 1H, α-propyl CH), 3.45 (br m, 1H, H-12), 3.57 (m, 1H, α-propyl CH), 4.0 (m,1H, γ-propyl CH), 4.33 (d, J=9 Hz, 1H, H-6), 4.37 (br d, J=27 Hz, 1H, H-11), 4.75 (br m, 2H, NH$_2$), 5.15 (s, 1H, H-7), 5.55; (d, J=9 Hz, 1H, H-9), 5.85 (t, J=9 Hz, 1H, H-5), 6.43 (br t, 1H, NH), 6.50 (t, J=9 Hz, 1H, H-4), 6.90 (d, J=9 Hz, 1H, H-3), 7.15 (s, 1H, H-19), 9.23 (s, 1H, NH-22); m/z 628. (M++Na); IR (KBr, cm$^{-1}$) 1735, 1695, 1655; Analysis calculated for $C_{31}H_{44}FN_3O_8 \cdot 0.25H_2O$: C, 61.01; H, 7.35; N, 6.88%. Found: C, 60.90; H, 7.40; N, 6.74%.

EXAMPLE 61

17-Allyamino-11-aminocarbonyl-17-demethoxyqeldanamifcin

17-Allylamino-17-demethoxygeldanamycin (0.200 g, 0.341 mmol) was dissolved in 5 mL of methylene chloride and cooled to 0° C. in a flame dried flask under nitrogen. Sodium isocyanate (0.311 g, 0.4.78 mmol) and trifluoroacetic acicl (0.545 g, 4.78 mmol, 0.368 mL) were added during 10 minutes. After stirring for 16 hours at room temperature, the reaction mixture was diluted with 200 mL of wal:er and extracted with 3×150 mL of chloroform. The combined organic layers were washed with 2×100 mL of water, dried with sodium sulfate, filtered and evaporated in vacuo to yield a residue, 0.236 g, which was flash chromatographed on 80 g of silica gel eluted with 69:1:30 ethyl acetate:methanol:hexanes. Fractions containing pure product were evaporated, taken up in 2 mL of chloroform and then precipitated with hexanes; 0.062 g (29%) mp 214–216° C.; $^1$H-NMR (300 MHz, CDCl$_3$)δ0.93(d, J=8Hz, 3H, 10-CH$_3$), 0.98(d, J=8Hz, 3H, 14-CH$_3$), 1.26 (br m, 1 H, H-13), 1.50 (m, 1H, H-13), 1.69 (s, 3H, 8-CH$_3$), 1.77 (br m, 1H, H-14), 1.96 (s, 3H, 2-CH$_3$), 2.24 (dd, J=16 Hz and 7 Hz, 1H, H-15), 2.56 (m, 1H, H-15), 2.85 (m, 1H, H-10), 3.31 (s, 3H, OCH$_3$), 3.32 (s, 3H, OCH$_3$), 3.46 (br m, 1H, H-12), 4.05 (br t, 2H, allylic CH$_2$), 4.39 (br m, 2H, NH$_2$), 4.43(br d, J=9 Hz, 1H, H-6), 4.71 (v br s, 2H, NH$_2$) 4.75 (m, 1H, H-11), 5.15–5.3 (m, 4H, vinylic CH$_2$, H-7, H-9), 5.73–5.9 (br m, 2H, H-5, vinylic CH), 6.15 (br t, 1H, NH), 6.48 (t, J=9 Hz, 1H, H-4), 7.11 (s, 1H, H-19), 7.23 (br m, 1H, H-3), 9.20 (s, 1H, NH-22); m/z 651. (M++Na); IR (KBr, cm$^{-1}$) 1740, 1725, 1705, 1680, 1645 1585, 1470; Analysis calculated for C$_{32}$H$_{44}$N$_4$O$_9$.5H$_2$O: C,58.61; H, 7.22; N, 8.54%. Found: C, 58.50; H, 6.51; N, 8.48%.

EXAMPLE 62

17-Azetidin-1-yl-11-N-BOC-β-alanyl-17-demethoxygeldanimycin

17-Azetidin-1-yl-17-demethoxygeldanamycin, the title compound of Example 18, (0.200 g, 0.341 mmol) was dissolved in 6 mL of dry methylene chloride and treated with N-BOC-β-alanine (0.077 g, 0.409 mmol), dicyclohexylcarbodiimide (0.084 g, 0.409 mmol) and dimethylaminopyridine (DMAP) (0.050 g, 0.409 mmol). After 24 hours the mixture was filtered to remove dicyclohexylurea and concentrated in vacuo to a residue which was dissolved in 200 mL of ethyl acetate and washed with 2×100 mL each of 1N hydrochloric acid, water and brine. The organic layer was dried with Na$_2$SO$_4$, filtered and evaporated in vacuo to yield a purple residue (0.240 g). This was flash chromatographed on silica gel eluted with 69:1:30 ethyl acetate:methanol:hexanes. Fractions containing pure product were evaporated to yield a residue which was dissolved in 1 mL of chloroform and precipitated with 100 mL of hexane; yield 0.098 g (38%) mp 122–125° C.; $^1$H-NMR (300 MHz, CDCl$_3$)δ0.87 (d, J=8 Hz, 3H, 10-CH$_3$), 0.95 (d, J=8 Hz, 3H, 14-CH$_3$), 1.17 (m, 1H, H-13), 1.6 (m, 1H, H-14), 1.63 (s, 3H, 8-CH$_3$), 1.90 (m, 1H, H-15), 1.95 (s, 3H, 2-CH$_3$), 2.35 (pent, J=8 Hz, 2H, 3'-azetidine CH$_2$), 2.46 (m, 2H, α-alanyl CH$_2$), 2.6–2.8 (m, 2H, H-15, H-10), 3.25 (s, 3H, OCH$_3$), 3.27 (s, 3H, OCH$_3$), 3.35 (m, 2H, β-alanyl CH$_2$), 3.66 (m, 1H, H-12), 4.46 (d, J=8 Hz, 1H, H-6), 4.55 (t, J=8 Hz, 4H, 2' and 4' azetidine CH$_2$), 4.44.9 (br s, 2H, NH$_2$), 5.06 (d, J=12 Hz, 1H, H-11), 5.15 (br t, 1H, alanyl NH), 5.27 (d, J=11 Hz, 1H, H-9), 5.53 (br s, 1H, H-7), 5.80 (t, J=9, 1H, H-5), 6.45 (t, J=9 Hz, 1H, H-4), 6.90 (s, 1H, H-19), 7.00 (m, J=9 Hz, 1H, H-3), 9.40 (s, 1H, NH-22); m/z 759. (M++Na); IR (KBr, cm$^{-1}$) 1732, 1645, 1583, 1541, 1477; Analysis calculated for C$_{39}$H$_{56}$N$_4$O$_{11}$.2H$_2$O: C, 59.08E; H, 7.63; N, 7.07%. Found: C, 59.20; H, 7.11; N, 7.16%.

EXAMPLE 63

17-Ayzetidin-1-yl-11-β-alanyl-17-demethoxyaeldanamycin

The product of Example 62 (0.050 g, 0.066 mmol) was dissolved in 1 mL of trifluoroacetic acid at 0° C. After 10 minutes the reaction mixture was evaporated in vacuo to a residue which was dissolved in 0.3 mL of methanol and precipitated with 20 mL of isopropylether; 0.35 g (71%) mp 138–142° C,. $^1$H-NMR (300 MHz, CDCl$_3$)δ0.84 (d, J=8 Hz, 3H, 10-CH$_3$), 0.96 (d, J=8 Hz, 3H, 14-CH$_3$), 1.24 (m, 1 H, H-13), 1.55 (m, 1H, H-13), 1.61 (s, 3H, 8-CH$_3$), 1.94 (s, 3H, 2-CH$_3$), 1.96 (m, 1H, H5), 2.35 (pent, J=8 Hz, 2H, 3' azetidine CH$_2$), 2.6–2.8 (m, 4H, α-alanyl CH$_2$ and H-15 and H-10), 3.18 (m, 2H, β-alanyl CH$_2$), 3.25 (s, 6H, OCH$_3$), 3.65 (m, 1H, H-12), 4.43 (br s, 1H, H-6), 4.57 (m, 4H, 2' and 4' azetidine CH$_2$), 5.0–5.5 (br s, 2H, NH$_2$), 5.15 (d, J=12 Hz, 1H, H-11), 5.3 (br m, 1H, H-9), 5.4 (br s, 1H, H-7), 5.78 (t, J=9 Hz, 1H, H-5), 6.44 (t, J=9 Hz, 1H, H-4), 6.85–7.00 (m, J=9 Hz, 1H, H-3), 6.93 (s, 1H, H-19), 8.16 (br s, 2H, alanyl NH$_2$), 9.35 (s, 1H, NH-22); m/z 657. (M++H); IR (KBr, cm$^{-1}$) 1731, 16838, 1647 1583, 1601, 1541, 1474; Analysis calculated for C$_{34}$H$_{48}$N$_4$O$_9$.3H$_2$O: C, 52.42; H, 6.72; N, 6.79%. Found: C, 52.23; H, 6.22; N, 6.61%.

EXAMPLE 64

17-Azetidin-1-yl-11-[N-(4-azidobenzoyl)-β-alanyl]-17-demethoxygeldanamycin

The title compound of Example 63 (0.020 g, 0.026 mmol) was dissolved in 0.5 mL of anhydrous dimethylformamide and treated with 4-azidobenzoic acid N-hydroxysuccinimide ester (0.007 g, 0.025 mmol) and triethylamine (0.0025 g, 0.025 mmol, 0.0034 mL). After three hours the reaction mixture was diluted with 200 mL of ethyl acetate and washed with 2×100 mL of water, 1N hydrochloric acid, and brine. The organic layer was dried with sodium sulfate, filtered and evaporated in vacuo to a residue. The residue was dissolved in 0.5 mL of chloroform and precipitated with 70 mL of hexanes, filtered and dried in vacuo; 0.012 g (61%) mp 123–6° C.; $^1$H-NMR (300 MHz, CDCl$_3$)δ0.85 (d, J=8 Hz, 3H, 10-CH$_3$), 0.94 (d, J=8 Hz, 3H, 14-CH$_3$), 1.15 (m, 1H, H-13), 1.63 (s, 3H, 8-CH$_3$), 1.85 (m, 1H, H-15), 1.95 (s, 3H, 2-CH$_3$), 2.35 (pent, J=8 Hz, 2H, 3' azetidine CH$_2$), 2.6 (t, J=8 Hz, 2H, α-alanyl CH$_2$), 2.7–2.9 (m, 2H, H-15 and H-10), 3.26 (s, 3H, OCH$_3$), 3.29 (s, 3H, OCH$_3$), 3.56 (m,1 H, β-alanyl CH$_2$), 3.70 (m, 1H, H-12), 3.82 (m, 1H, β-alanyl CH$_2$), 4.4–4.9 (m, 7H, H-6, 2' and 4' azetidine CH$_2$, NH$_2$), 5.10 (d, J=12 Hz, 1H, H-11), 5.3 (br m, 1H, H-9), 5.53 br s, 1H, H-7), 5.79 (t, J=9, 1H, H-5), 6.45 (t, J=9, 1H, H-4), 6.91 (s, 1H, H-19), 6.9–7.0 (m, 2H, H-3, NH), 6.98 (d of ABq, J=10 Hz, 2H, aromatic CH), 7.75 (d of ABq, J=10 Hz, 2H, aromatic CH), 8.16 (br s, 2H, alanyl NH$_2$), 9.38 (s, 1H, NH-22).

EXAMPLE 65

17-Azetidin-1-yl-11-acetyl-17-demethoxygeldanamycin

17-Azetidin-1-y-17-demethoxygeldanamycin, the title compound of Example 18, (0.200 g, 0.341 mmol) was dissolved in 5 mL of methylene chloride in a flame dried flask under nitrogen and treated with acetic anhydride (0.070 g, 0 683 mmol, 0.064 mL), DMAP (0.042 g, 0.341 mmol) and triethylamine 0.105 g (1.04 mmol, 0.145 mL) at room temperature. After 3 hours the mixture was diluted with 200 mL of methylene chloride and washed with 100 mL of water and 2×100 mL of brine. The organic layer was dried with sodium sulfate, filtered and evaporated in vacuo to a residue; 0.30 g. The residue was flash chromatographed on 120 g of silica gel with 2.5% methanol in chloroform to afford pure product, 0.120 g, which was recrystallized from 10 mL of toluene; 0.080 g (37%) mp 195° C.(dec); $^1$H-NMR (300

MHz, CDCl₃)δ0.93 (m, 6H, 14-CH₃ and 10-CH₃), 1.1–1.3 (m, 2H, H-13), 1.55 (m, 1H, H-14), 1.65 (s, 3H, 8-CH₃), 1.95 (s, 3H, 2-CH₃), 1.96 (s, 3H, acetyl CH₃), 2.0 (m, 1H, H-15), 2.35 (pent, J=8 Hz, 2H, 3'-azetidine CH₂), 2.6–2.85 (m, 2H, H-15, H-10), 3.29 (s, 3H, OCH₃), 3.31 (s, 3H, OCH₃), 3.60 (sept, J=8 Hz, 1H, isopropyl CH), 3.63 (m, 1H, H-12), 4.45 (d, J=8 Hz, 1H, H-6), 4.55 (t, J=8 Hz, 4H, 2' and 4' azetidine CH₂), 4.73 (br s, 2H, NH₂), 5.0 (m, 1H, H-11), 5.75 (d, J=11 Hz, 1H, H-9), 5.41 (br s, 1H, H-7), 5.78 (t, J=9 Hz, 1H, H-5), 6.46 (t, J=9 Hz, 1H, H-4), 6.91 (s, 1H, H-19), 7.10 (m, J=9 Hz, 1H, H-3), 9.34 (s, 1H, NH-22); m/z 650. (M++Na); IR (KBr, cm⁻¹) 1735, 1685, 1645; Analysis calculated for C₃₃H₄₅N₃O₉:C, 63.14; H, 7.26; N, 6.69%. Found: C, 63.36; H, 6.94; N, 6.55%.

EXAMPLE 66

17-Azetidin-1-yl-11-aminocarbonyl-17-demethoxygeldanamycin

Prepared in the manner of Example 61 from 17-azetidin-1-yl-17-demethoxygeldanamycin, the title compound of Example 18, (0.200 g, 0.341 mmol); yield 0.083 g (39%) mp 168–171° C.; ¹H-NMR (300 MHz, CDCl₃)δ0.98(d, J=8Hz, 3H, 10-CH₃), 1.01 (d, J=8Hz, 3H, 14-CH₃), 1.3 (br m, 2H, H-13), 1.73 (s, 3H, 8-CH₃), 1.75 (br m, 1H, H-14), 2.02 (s, 3H, 2-CH₃), 2.15 (m, 1H, H-15), 2.40 (pent, J=8 Hz, 2H, 3'-azetidine CH₂), 2.67 (m, 1H, H-15), 2.87 (m, 1H, H-10), 3.36 (s, 6H, OCH₃), 3.60 (m, 1H, H-12), 4.39 (br m, 2H, NH₂), 4.5 (br d, J=9 Hz, 3H, H-6, NH₂), 4.64 (br t, J=8 Hz, 6H, 2' and 4' azetidine CH₂, NH₂), 4.86 (m, 1H, H-11), 5.35 (d, J=12 Hz, 1H, H-9), 5.40 (br s, 1 H, H-7), 5.83 (br t, J=9 Hz, 1H, H-5), 6.54 (t, J=9 Hz, 1H, H-4), 6.97 (s, 1H, H-19), 7.21 (br m, 1H, H-3), 9.36 (s, 1H, NH-22); m/z 629. (M⁺); IR (KBr, cm⁻¹) 1720, 1686, 1648 1533,1475; Analysis calculated for C₃₂H44N₄O₉.H₂O: C, 59.42; H, 7.61; N, 8.66%. Found: C, 59.67; H, 6.81; N, 8.38%.

EXAMPLE 67

17-Allylamino-11-isopropylsulfamylcarbonyl-17-demethoxygeldanamycin

17-Allylamino-17-demethoxygeldanamycin (0.200 g, 0.341 mmol) was dissolved in 5 mL of methylene chloride and cooled to 0° C. in a flame dried flask under nitrogen. Chlorosulfonylisocyanide (0.080 mg, 0.564 mmol, 0.049 mL) was added dropwise during 10 minutes. After stirring for one hour in the cold, isopropyl amine (0.066 g, 1.13 mmol, 0.096 mL) was added and the reaction mixture allowed to warm to room temperature during one hour. The reaction mixture was diluted with 100 mL of chloroform and extracted with 10 mL of water. The aqueous layeir was back extracted with 3×100 mL of chloroform. The pooled organic layers were extracted with 3×75 mL of 1N NaOH. The combined basic layers were washed with 3×100 mL of chloroform. The aqueous layer was acidified to pH 3 with 1 N hydrochloric acid and extracted with 3×100 ml of chloroform. These latter organic extracts were pooled, washed with 2×100 mL of brine, dried with sodium sulfate, filtered and evaporated in vacuo to a solid, 0.213 g. Flash column chromatography on silica gel eluted with 5% methanol in chloroform yielded pure title compound which was dissolved in 1 mL of chloroform and precipitated with hexanes, filtered and dried in vacuo; yield 0.061 g (25%) mp 137–139° C.; ¹H-NMR (300 MHz, CDCl₃)δ0.94 (d, 3H, J=8 Hz, 1-CH₃), 0.98 (d, 3H, J=8Hz, 14-CH₃), 1.1(m, 6H, isopropyl CH₃),1.3–1.55 (br m, 2H, H-13), 1.65 (s, 3H, 8-CH₃), 1.70 (br m, 1H, H-14), 1.95 (s, 3H, 2-CH₃), 2.13 (m, 1H, H-15), 2.27 (dd, J=7 Hz, 16 Hz, 1H, H-15), 3.00 (m, 1H, H-10), 3.25 and 3.27 (br s, 6H, OCH₃), 3.5 (m, 1H, isopropyl CH), 3.57 (br m, 1H, H-12), 4.05 (br t, 2H, allylic CH₂), 4.43 (br m, 1H, H-6), 4.7 (br m, 2H, NH₂), 4.9 (br s, 1H, NH) 5.02 (br d, J=11 Hz, 1H, H-11), 5.2 (br d, 2H, vinylic CH₂), 5.38 (br m, 2H, H-7 and H-9), 5.75 (t, J=9 Hz, 1H, H-5), 5.85 (m, 1H, vinylic CH), 6.27 (br t, 1H, NH), 6.45 (t, J=9 Hz, 1H, H-4), 7.03 (br m, 1H, H-3), 7.10 (s, 1H, H-19), 9.30 (s, 1H, NH-22); m/z 772. (M++Na); IR (KB r, cm⁻¹) 1737, 1690, 1645; Analysis calculated for C₃₅H₅₁N₅O₁₁S.0.5H₂O: C, 55.39; H, 6.91; N, 9.23%. Found: C, 55.36; H, 6.95; N, 9.19%.

The compounds of Examples 68 and 69 were prepared by the method of Example 67 from the appropriate 17-demethoxy-geldanamycin.

EXAMPLE 68

17-β-Fluoroethylamino-11-isopropysulfamylcarbonyl-17-demiethoxygeldanamycin

Yield 0.122 g (38%) mp 142–146° C. (dec); ¹H-NMR (300 MHz, CDCl₃)δ0.93 (d, 3H, J=8Hz, 10-CH₃), 0.97 (d, 3H, J=8Hz, 14-CH₃), 1.07 (d, J=8 Hz, 6H, isopropyl CH₃), 1.36 (br m, 1H, H-13), 1.46 (br m, 1H, H-13), 1.63 (br s, 4H, 8-CH₃ and H-14), 1.94 (s, 3H, 2-CH₃), 2.1 (br m, 1H, H-15), 2.82 (dd, J=7 Hz, 16 Hz, 1H, H-15), 2.95 (br m, 1H, H-10), 3.24 (s, 3H, OCH₃), 3.26 (s, 3H, OCH₃), 3.49 (sept, J=8 Hz, 1H, isopropyl CH), 3.59 (br m, 1H, H-12), 3.77 (two br d m, J=23 Hz, 2H, α-ethyl CH₂), 4.43 (br s, 1H, H-6), 4.56 (two br d t, J=47 Hz 7 Hz, 2H, β-ethyl CH₂), 4.8 (br m, 2H, NH₂), 5.02 (br d, 2H, H-11 and NH), 5.75 (t, J=9 Hz, 1 H, H-5), 5.86 (br d, 2H, H-7 and H-9), 6.25 (br t, 1H, NH), 6.45 (t, J=9 Hz, 1H, H-4), 7.00 (br s, 1H, H-3), 7.10 (s, 1H, H-19), 7.55 (br s, 1H, NH), 9.25 (s, 1H, NH-22); m/z 778. (M++Na); IR (KBr, cm⁻¹) 1735,1690,1645,1590,1480; Analysis calculated for C₃₄H₅₀FN₅O₁₁S: C, 60.69; H, 6.96; N, 7.07%. Found: C, 60.23; H, 6.99; N, 7.02%.

EXAMPLE 69

17-β-Cyanoethylamino-11-isopropylsulfamylcarbonyl-17-dernethoxygeldanamycin

Yield 0.037 g (11%) mp 150–154° C. (dec); ¹H-NMR (300 MHz, CDCl₃)δ0.98 (d, 6H, J=8 Hz, 10-Me and 14-Me), 1.08 (d, J=8 Hz, 6H, isopropyl CH₃), 1.37 (br m, 1H, H-13), 1.5 (br t, 1H, H-13), 1.65 (s, 3H, 8-Me), 1.75 (br m, 1H, H-14), 1.95 (s, 3H, 2-Me), 2.04 (m, 1 H, H-15), 2.66 (t, J=8 Hz, 2H, β-ethyl CH₂), 2.78 (m, 1H, H-15), 3.00 (br m, 1H, H-10), 3.26 (s, 3H, OCH₃), 3.28 (s, 3H, OCH₃), 3.50 (sept, J=8 Hz, 1H, isopropyl CH), 3.56 (br m, 1H, H-12), 3.77 (br m, 2H, α-ethyl CH₂), 4.40 (br d, J=9 Hz, 1H, H-6), 4.75 (br m, 2H, NH₂), 4.93 (br s, 1H, NH), 4.98 (br d, 1H, H-11), 5.34 (br m, 2H, H-7 and H-9), 5.76 (t, J=9 Hz, 1H, H-5), 5.96 (br t, 1H, NH), 6.45 (t, J=9 Hz, 1H, H-4), 7.00 (br s, 1H, H-3), 7.13 (s, 1H, H-19), 7.38 (br s, 1H, NH), 9.15 (s, 1H, NH-22); m/z 785. (M++Na); IR (KBr, cm⁻¹) 2320, 1730, 1690, 1640, 1580, 1480; Analysis calculated for C₃₅H₅₀N₆O₁₁.1.25H₂O: C, 54.78; H, 6.63; N, 10.95%. Found: C, 54.75; H, 6.16; N, 10.71%.

EXAMPLE 70

17-Azetidin-1-yl-11-isopropyisulfamylcarbonyl-17-demethcoxygeldanamycin

17-Azetidin-1-yl-17-demethoxygeldanamycin (0.200 g, 0.341 mmol) was dissolved in 5 mL of methylene chloride and cooled to 0° C. in a flame dried flask under nitrogen. Chlorosulfonylisocyanide (0.053 mg, 0.376 mmol, 0.033 mL) was added dropwise during 10 minutes. After stirring for two hours in the cold, isopropylamine (0.044 g, 0.75 mmol, 0.064 mL) was added and the reaction mixture allowed to warm to room temperature during one hour. The reaction mixture was diluted with 100 mL of methylene chloride and extracted with 2×100 mL of 1 N NaOH The combined basic layers were washed with 3×150 mL of methylene chloride and then acidified to pH 3 with 1 N hydrochloric acid. The acidic aqueous layer was extracl:ed with 3×150 mL of methylene chloride. These latter organic extracts were pooled, dried with sodium sulfate, filtered and evaporated in vacuo to a solid, 0.121 g which was dissolved in 1 mL of methylene chloride and precipitated with hexanes, filtered and dried in vacuo; 0.110 9 (43%) mp 14548° C.; $^1$H-NMR (300 MHz, CDCl$_3$)δ0.9(d, J=8 Hz, 3H, 14-CH$_3$), 0.96 (d, J=8 Hz, 3H, 10-CH$_3$), 1.14 (d, J=8 Hz, 6H, isopropyl CH$_3$), 1.3 (m, 1H, H-13), 1.5 (m, 1H, H-13), 1.6 (m, 1H, H-14), 1.64 (s, 3H, 8-CH$_3$), 1.94 (s, 3H, 2-CH$_3$), 2.0 (m, 1H, H-15), 2.36 (p, J=8 Hz, 2H, 3' azetidine CH$_2$), 2.73 (dd, J=8 Hz and 16 Hz, 1H, H-15), 2.9 (m, 1H, H-10), 3.25 (s, 3H, OCH$_3$), 3.27 (s, 3H, OCH$_3$), 3.52 (sept, J=8 Hz, 1H, isopropyl CH), 3.63 (m, 1H, H-12), 4.43 (m, 1H, H-6), 4.57 (t, J=8 Hz, 4H, 2' and 4' azetidine CH$_2$), 4.78 (br s, 2H, NH$_2$), 5.0 (br s, 1 H, H-11), 5.86 (m, 2H, H-7 and H-9), 5.75 (t, J=9 Hz, 1H, H-5), 6.45 (t, J=9 Hz, 1H, H-4), 6.9 (s, 1H, H-19), 6.95 (m, J=9 Hz, 1H, H-3), 7.45 (m, 1H, NH), 9.35 (s, 1H, NH-22); m/z 772. (M++Na); IR (KBr, cm$^{-1}$) 1735, 1685, 1645; Analysis calculated for C$_{35}$H$_{51}$N$_5$O$_{11}$S. 1.25H$_2$O: C, 54.43; H, 6.98; N, 9.07%. Found: C, 54.42; H, 6.54; N, 8.73%.

EXAMPLE 71

17-β-Cyanoethylamino-4.5-dihydro-11-isopropylsulfamylcarbonyl-17-demethoxygeldanamycin The title compound was prepared by the method of Example 70 from the compound of Example 11.

Yield 0.087 g (46%) mp 128–132° C. (dec); $^1$H-NMR (300 MHz, CDCl$_3$)δ0.92 (d, J=8 Hz, 3H, 10-CH$_3$), 0.93 (d, J=8 Hz, 3H, 14-CH$_3$), 1.07 (d, J=8 Hz, 3H, isopropyl CH$_3$), 1.09 (d, J=8 Hz, 3H, isopropyl CH$_3$),1.17 (br m, 1H, H-13),1.36 (br t, 1H, H-13), 1.43 (s, 3H, 8-CH$_3$), 1.46 (br m, 1H, H-14), 1.58 (m, 2H, H-5), 1.75 (s, 3H, 2-CH$_3$), 2.00 (dd, J=14 Hz and 6 Hz, 1H, H-15), 2.23 (m, 2H, H-4), 2.56 (t, J=8 Hz, 2H, β-ethyl CH$_2$), 2.77 (m,1 H, H-15), 3.06 (br m,1 H, H-10), 3.25 (s, 3H, OCH), 3.27 (s, 3H, OCH$_3$), 3.35 (br m, 1 H, H-12), 3.47 (sept, J=8 Hz, 1H, isopropyl CH), 3.66 (br m, 2H, α-ethyl CH$_2$), 4.54.63 (br m, 3H, H-6, NH$_2$ and NH), 4.85 (d, J=6 Hz, 1 H, H-7), 5.05 (br s, 1 H H-7), 5.74 (d, J=9 Hz, 1 H H-9), 5.87 (br t, 1H, NH), 6.26 (t, J=7 Hz, 1H, H-3), 7.05 (s, 1H, H-19), 7.40 (br s, 1H, NH), 9.00 (s, 1H, NH-22); m/z 787 (M++Na); IR (KBr, cm$^{-1}$) 2320, 1730, 1690, 1645, 1580, 1480; Analysis calculated for C$_{35}$H$_{52}$N$_6$O$_{11}$S.0.25H$_2$O: C, 54.71; H, 6.75; N, 10.93%. Found: C, 54.48; H, 6.88; N, 10.68%.

EXAMPLE 72

17-Azetidin-1-yl-11-(4'-azidophenyl)sulfamylcarbonyl-17-demethoxygeldanamycin

17-Azetidin-1-yl-17-demethoxygeldanamycin, the title compound of Example 18, (0.250 g, 0.427 mmol) was dissolved in 5 mL of methylene chloride and cooled to 0° C. in a flame dried flask under nitrogen. Chlorosulfonylisocyanide (0.099 mg, 0.704 mmol, 0.061 mL) was added dropwise during 10 minutes. After stirring for one hour in the cold, 4-azidoaniline (0.126 g, 0.938 mmol) was added and the reaction mixture allowed to warm to room temperature during one hour. The reaction mixture was evaporated to dryness and the residue flash chromatographed on 120 g silica gel with 3% methanol in chloroform affording pure product which was dissolved in 1 mL of chloroform and precipitated with hexanes; Yield 0.059 g (17%), mp 152–154° C.; $^1$H-NMR (300 MHz, CDCl$_3$)δ0.85 (d, J=8 Hz, 3H, 14-CH$_3$), 0.94 (d, J=8 Hz, 3H, 10-CH$_3$), 1.2 (m, 1H, H-13), 1.36–1.7 (m, 2H, H-13 and H-14), 1.6 (s, 3H, 8-CH$_3$), 1.94 (br s, 4H, 2-CH$_3$ and H-15), 2.35 (pent, J=8 Hz, 2H, 3'-azetidine CH$_2$), 2.65–2.9 (br m, 2H, H-10 and H-15), 3.24 (br s, 6H, OCH$_3$), 3.64 (m, 1H, H-1 2), 4.46 (br s, 1H, H-6), 4.55 (t, J=8 Hz, 4H, 2' and 4' azetidine CH$_2$), 4.85–5.1 (br s, 2H, NH$_2$ and H-7), 5.85 (br s, 1H, H-11), 5.48 (br s, 1H, H-9), 5.77 (br t, J=9 Hz, 1H, H-5), 6.45 (t, J=9 Hz, 1H, H-4), 6.86 (s, 1H, H-19), 6.8–7.15 (m, 5H, H-3 and aromatic CH), 7.8 (v br d s, 1H, NH), 9.35 (s, 1H, NH-22); m/z 847. (M++Na); IR (KBr, cm$^{-1}$) 2108, 1737, 1689, 1647, 1584, 1481; Analysis calculated for C$_{38}$H$_{48}$N$_8$O$_{11}$S.1.5H$_2$O: C, 53.57; H, 5.86; N, 13.15%. Found: C, 53.70; H, 5.57; N, 13.02%.

EXAMPLE 73

17-Allylamino-11-azetidin-1-ylsulfamylcarbonyl-17-demethoxygeldanamycin

17-Allylamino-17-demethoxygeldanamycin (0.200 g, 0.341 mmol) was dissolved in 5 mL of methylene chloride and cooled to 0° C. in a flame dried flask under nitrogen. Chlorosulfonylisocyanide (0.053 mg, 0.376 mmol, 0.033 mL) wvas added dropwise during 10 minutes. After stirring for one hour in the cold, azetidine (0.043 g, 0.75 mmol, 0.051 mL) was added and the reaction mixture allowed to warm to room temperature during one hour. The reaction mixture was evaporated to a residue and flash column chromatographed on 60 g silica gel eluted with 69:1:30 ethyl acetate:methanol:hexanes to yield pure target compound which was dissolved in 1 mL of chloroform, precipitated with hexanes and dried in vacuo; Yield 0.102 g (40%) mp 134–137° C.; $^1$H-NMR (300 MHz, CDCl$_3$)δ0.92 (d, 3H, J=8Hz, 10-CH$_3$), 1.01 (d, 3H, J=8Hz, 14-CH$_3$), 1.4 (br m, 1H, H-13), 1.5 (br m, 2H, H-13 and H-14), 1.65 (s, 3H, 8-CH$_3$), 1.95 (s, 3H, 2-CH$_3$), 2.13 (m, 1H, H-15), 2.05–2.2 (m, 3H, H-15 and azetidine 3'-CH$_2$), 2.78 (dd, J=6 Hz and 15 Hz, 1H, H-15), 2.93 (m, 1H, H-10), 3.26 (s, 3H, OCH$_3$), 3.28 (s, 3H, OCH$_3$), 3.63 (br m, 1H, H-12), 3.95–4.05 (br m, 6H, allylic CH$_2$ and azetidine 2' and 4' CH$_2$), 4.45 (br s, 1 H, H-6), 4.7 (br m, 2H, NH$_2$), 5.02 (br d, J=11 Hz, 1H, H-11), 5.2 (m, 2H, vinylic CH$_2$), 5.4 (br m, 2H, H-7 and H-9), 5.73–5.93 (m, 2H, H-5 and vinylic CH), 6.25 (br t, 1H, NH), 6.45 (t, J=9 Hz, 1H, H-4), 7.03 (br m, 1H, H-3), 7.10 (s, 1H, H-19), 9.32 (s, 1H, NH-22); m/z 769. (M++Na); IR (KBr, cm$^{-1}$) 1734, 1691, 1645 1579, 1474; Analysis calculated for C$_{35}$H$_{49}$N$_5$O$_{11}$S.0.75H$_2$O: C, 55.21; H, 6.69; N, 9.19%. Found: C, 55.19; H, 6.18; N, 9.20%.

EXAMPLE 74

17-Azetidin-1-yl-11-piperazinylsulfamylcarbonyl-17-demethioxygeldanamycin

17-Azetidin-1-yl-17-demethoxygeldanamycin, the title compound of Example 18, (0.50 g, 0.854 mmol) was dissolved in 5 mL of methylene chloride and cooled to 0° C. in a flame dried flask under nitrogen. Chlorosulfonylisocyanide (0.133 mg, 0.939 mmol, 0.082 mL) was added dropwise during 10 minutes. After stirring for one hour in the cold, piperazine (0.162 g, 1.88 mmol) was added and the reaction mixture allowed to warm to room temperature during one hour. The reaction mixture was evaporated to dryness and the residue flash chromatographed on 200 g silica gel with 20% methanol in chloroform affording pure product which was dissolved in 5 mL of chloroform and precipitated with 150 mL of hexanes; Yield 0.161 g (24%), mp 180–182° C.; $^1$H-NMR (300 MHz, CDCl$_3$)δ0.86(m, 3H, 14-CH$_3$), 0.9 (m, 3H, 10-CH$_3$), 1.6 (s, 3H, 8-CH$_3$), 1.94 (br s, 2-CH$_3$), 2.35 (pent, J=8 Hz, 2H, 3'-azetidine CH$_2$), 3.25 (br s, 6H, OCH$_3$), 3.64 (m, 1H, H-12), 4.46 (br s, 1H, H-6), 4.6 (t, J=8 Hz, 4H, 2' and 4' azetidine CH$_2$), 6.43 (br t, 1H, H4), 6.9 (s, 1H, H-19), 9.35 (s, 1H, NH-22), other protons observed but not well defined or assignable; m/z 799. (M++Na); IR (KBr, cm$^{-1}$) 1734, 1689, 1646, 1600, 1471; Analysis calculated for C$_{33}$H$_{52}$N$_6$O$_1$S.2H$_2$O: C, 53.19; H, 6.94; N, 10.34%. Found: C, 52.90; H, 6.81; N, 10.13%.

EXAMPLE 75

17-Azetidin-1-yl-11-(4'-methyl-1 '-piperazinyl)-sulfamylcarbonyl-17-demethoxy-geldanamycin 17-Azetidin-1-yl-17-demethoxygeldanamycin, the title com pound of Example 18, (0.200 g, 0.341 mmol) was dissolved in 5 mL of methylene chloricde and cooled to 0° C. in a flame dried flask under nitrogen. Chlorosulfonylisocyanide (0.053 mg, 0.376 mmol, 0.033 mL) was added dropwise during 10 minutes. After stirring for one hour in the cold, N-methylpiperazine (0.075 g, 0.75 mmol, 0.083 mL) was added and the reaction mixture allowed to warm to room temperature during one hour. The reaction mixture was diluted with 100 mL of chloroform and extracted with 100 mL. of water and 2×100 mL of brine. The organic layer was dried with sodium sulfate, filtered and evaporated in vacuo to a solid, 0.280 g. This was flash chromatographed con silica gel with 10% methanol in chloroform affording pure product: yield 0.114 g (42%) mp 147–49° C.; $^1$H-NMR (300 MHz, CDCl$_3$)δ1.11 (d, J=8 Hz, 3H, 14-CH$_3$), 1.21 (d, J=8 Hz, 3H, 10-CH$_3$), 1.55 (m, 1H, H-13), 1.72 (m, 1H, H-13), 1.83 (m, 1H, H-14), 1.86 (s, 3H, 8-CH$_3$), 2.2 (br s, 4H, 2-CH$_3$ and H-15), 2.53 (s, 3H, N-CH$_3$), 2.60 (br t, J=8 Hz, 2H, 3'-azetidine CH$_2$), 2.70 (br s, 4H, piperazinyl CH$_2$), 2.9–3.1 (m, 2H, H-10 and H-15), 3.53 (s, 6H, OCH$_3$), 3.86 (m, 1H, H-12), 4.69 (br s, 1H, H-6), 4.82 (t, J=8 Hz, 4H, 2'and 4' azetidine CH$_2$), 5.15 (br s, 2H, NH$_2$), 5.72 (br s, 1H, H-7), 5.57 (br d, 1H, H-11), 5.66 (br s, 1H, H-9), 6.00 (t, J=9 Hz, 1H, H-5), 6.68 (t, J=9 Hz, 1H, H-4), 7.15 (s, 1H, H-19), 7.24 (br s, 1H, H-3), 7.45 (s, 1H, NH), 9.60 (s, 1H, NH-22); m/z 813. (M++Na); IR (KBr, cm$^{-1}$) 1738, 1688, 1646, 1583, 1471; Analysis calculated for C$_{37}$H$_{54}$N$_6$O$_{11}$SeH$_2$O: C, 54.94; H, 6.97; N, 10.39%. Found: C, 54.92; H, 6.87; N, 10.2S%.

EXAMPLE 76

17-Allylamino-11-keto-17-demethoxygeldanamycin

17-Allylamino-17-demethoxygeldanamycin (90 mg, 0.15 mmol) was dissolved in CHCl$_3$ (4 mL) to which was added the Dess-Martin periodinane (382 mg, 0.90 mmol) and the reaction heated to reflux. After 1 hour the reaction was complete and the reaction mixture diluted with CHCl$_3$. The organic layer was washed with aqueous Na$_2$S$_2$O$_3$, saturated aqueous sodium bicarbonate and dried over sodium sulfate. The solvent was removed by evaporation and the residue recrystallized from ethyl acetate/hexanes to give 17-allylamino-11-keto-17-demethoxygeldariamycin, yield 84 mg (96%), as light red crystals, mp 112–118° C. (dec); $^1$H-NMR (300 MHz, CDCl$_3$)δ1.02 (d, 3 H, J=7Hz), 1.25 (d, 3 H, J=7Hz), 1.48 (m, 2 H), 1.75 (m, 1H), 1.80 (s, 3 H), 1.98 (s, 3 H), 2.32 (dd, 1H, J=14 Hz, 5 Hz), 2.58 (dd, 1H, J=14 Hz, 7 Hz), 3.29 (overlapping s, 6 H), 3.66 (m, 1), 4.08 (m, 3H), 4.28 (d, 1H, J=8 Hz), 4.82 (br exchangeable, 2 H), 5.18–5.3 (m, 3 H), 5.55 (d, 1 H, J=9 Hz), 5.83–6.0 (m, 3 H), 6.83 (br exchangeable, 1 H), 6.49 (t, 1 H, J=11 Hz), 6.92 (d, 1 H, J=11 Hz), 7.19 (s, 1 H), 9.22 (s, 1 H); mass spectrum m/z 585 (M+2); Analysis calculated for C$_{31}$H$_{41}$N$_3$O$_8$.0.5 (ethyl acetate): C, 63.14; H, 7.23; N, 6.69%. Found: C, 63.19; H, 7.06; N, 6.92%.

The 11-keto compounds of Examples 77–87 were prepared by oxidation of the appropriate 17-amino substituted 17-demethoxygeldanamycins acccordingtothe method of Example 76.

EXAMPLE 77

17-Cyclopropylamino-11-keto-17-demethoxygeldanamycin

Mp 110–115° C. (dec); $^1$H-NMR (300 MHz, CDCl$_3$) δ0.75–0.135 (m, 4 H), 1.03 (d, 3 H, J=7 Hz), 1.24 (d, 3 H, J=7 Hz), 1.72 (m, 1 H), 1.79 (s, 3 H), 1.98 (s, 3 H), 2.78 (m, 3 H), 3.32 (s, 3 H), 3.4–3.5 (m, 4 H), 4.08 (m, 2 H), 4.28 (d, 1 F,, J=8 Hz), 4.81 (br exchangeable, 2 H), 5.15 (s, 1 H), 5.57 (d, 1 H, J=10 Hz), 5.71 (t, 1 H, J=7 Hz), 6.26 (br s, 1 H), 6.51 (t, 1 H, J=12 Hz), 6.92 (d, 1 H, J=12 Hz), 7.15 (s, 1 H), 9.22 (s, 1 H); mass spectrum m/z 606 (M+Na)

EXAMPLE 78

17-Isopropylamino-11-keto-17-demethoxygeldanamycin

Mp 105–111 ° C. (dec); $^1$H-NMR (300 MHz, CDCl$_3$) δ1.02 (d, 3 H, J=7 Hz), 1.25 (overlapping doublets, 9 H), 1.48 (m, 2 H), 1.75 (m, 1 H), 1.80 (s 3 H), 1.98 (s, 3 H), 2.27 (dd, 1 H, J=14 Hz, 5 Hz), 2.66 (dd, 1 H, J=14 Hz, 7 Hz), 3.32 (overlapping s, 6 H), 3.67 (m, 1 H), 3.98 (m, 1 H), 4.09 (t, 1 H, J=5 Hz), 4.38 (d, 1 H, J=9 Hz), 4.82 (br exchangeable, 2 H), 5.17 (s, 1 H), 5.54 (d, 1 H, J=9 Hz), 5.83 (t, 1 H, J=7 Hz), 6.17 (d, 1 H, J=9 Hz), 6.49 (t, 1 H, J=11 Hz), 6.92 (d, 1 H , J=11 Hz), 7.17 (s, 1 H), 9.27 (s, 1 H); mass spectrum m/z 587 (M+2); Analysis calculated for C$_{31}$H$_{43}$N$_3$O$_8$.0.2CH$_2$Cl$_2$: C, 62.22; H, 7.20; N,6.98%. Found: C, 62.16; H, 7.0; N, 6.75%.

EXAMPLE 79

17-Methylamino-11-keto-17-demethoxygeldanamycin

Mp 108–120° C. (dec); $^1$H-NMR (300 MHz, CDCl$_3$) δ1.05 (d, 3 H, J=7 Hz), 1.23 (d, 3 H, J=7 Hz), 1.48 (m, 2 H), 1.80 (s, 3 H), 1.97 (s, 3 H), 2.43 (dd, 1 H, J=14 Hz, 5 Hz), 2.68 (dd, 1 H, J=14 Hz, 7 Hz), 3.17 (s, 3 H), 3.30 (overlapping s, 6 H), 3.68 (m, 1 H), 4.11 (t, 1 H, J=5 Hz), 4.32 (d, 1 H, .J=8 Hz), 4.80 (br exchangeable, 2 H), 5.21 (s, 1 H), 5.53 (d, 1 H, J=10 Hz), 5.83 (t, 1 H, J=7 Hz), 6.51 (t, 1 H, J=12 Hz), 6.92 (d, 1 H, J=10 Hz), 7.19 (s, 1 H), 3.28 (s, 1 H); mass spectrum m/z 580 (M+Na).

EXAMPLE 80

17-(2'-Hydroxyethylamino)-11-keto-17-demethoxygeldanamycin

Mp 108–111 ° C. (dec); $^1$H-NMR (300 MHz, CDCl$_3$) δ1.07 (d, 3 H, J=7 Hz), 1.25 (d, 3 H, J=7 Hz), 1.51 (m, 2 H), 1.76 (m, 1 H), 1.81 (s, 3 H), 1.98 (s, 3 H), 2.32 (dd, 1 H, J=14 Hz, 4 Hz), 2.63 (dd, 1 H, J=14 Hz, 7 Hz), 3.34 (overlapping s, 6 H), 3.62 (m, 3 H), 3.88 (t, 2 H, J=5 Hz), 4.09 (t, 1 H, J=5 Hz), 4.28 (d, 1 H, J=9 Hz), 4.8 (br exchangeable, 2 H), 5.18 (s, 1 H), 5.53 (d, 1 H, J=13 Hz), 5.79 (d, 1 H, J=8 Hz), 6.48 (t, 1 H, J=14 Hz), 6.92 (d, 1 H, J=14 Hz), 7.18 (s, 1 H), 9.25 (s, 1 H); mass spectrum m/z 589 (M+2); Analysis calculated for $C_{30}H_{41}N_3O_9$: C, 61.32; H, 7.03; N, 7.15%. Found: C, 60.96; H, 7.12; N, 6.90%.

EXAMPLE 81

17-(2'-Methoxyethylamino)-11-keto-17-demethoxygeldanaycin

Mp 130–134° C. (dec); $^1$H-NMR (300 MHz, CDCl$_3$) δ1.05 (d, 3 H, J=7 Hz), 1.24 (d, 3 H, J=7 Hz), 1.82 (m, 2 H), 1.85 (s, 3 H), 2.00 (s, 3 H), 2.34 (dd, 1 H, J=14 Hz, 5 Hz), 2.62 (dd, 1 H, J=14 Hz, 7 Hz), 3.33 (overlapping s, 6 H), 3.40 (s, 3 H), 3.6–3.7 (m, 5 H), 4.10 (m, 2 H), 4.31 (d, 1 H, J=9 Hz), 4.8 (br exchangeable, 2 H), 5.22 (s, 1 H), 5.55 (d, 1 H. J=10 Hz), 5.82 (t, 1 H, J=7 Hz), 6.49 (t, 1 H, J=12 Hz), 6.92 (d, 1 H, J=10 Hz), 7.18 (s, 1 H), 9.24 (s, 1 H); mass spectrum m/z 603 (M+2); Analysis calculated for $C_{31}H_{43}N_3O_9$: C, 61.79; H, 7.20; N, 6.98%. Found: C, 61.75; H, 7.02; N, 6.86%.

EXAMPLE 82

17-(2'-Methylthioethylamino)-11-keto-17-demethoxygeldanamycin

Mp 95–100° C. (dec); $^1$H-NMR (300 MHz, CDCl$_3$)δ1.05 (d, 3 H. J=7 Hz), 1.23 (d, 3 H, J=7 Hz), 1.48 (m, 2 H), 1.80 (m, 1 H), 1.81 (s, 3 H), 1.95 (s, 3 H), 2.11 (s, 3 H), 2.32 (dd, 1 H, J=14 Hz, 5 Hz), 2.63 (dd, 1 H, J=14 Hz, 5 Hz), 2.76 (t, 2 H, J=7 Hz), 3.32 (overlapping s, 6 H), 3.67 (t, 2 H, J=7 Hz), 3.67 (single proton under triplet), 4.08 (t, 1 H, J=5 Hz), 4.37 (d, 1 H, J=7 Hz), 4.8 (br s, 2 H), 5.18 (s, 1 H), 5.52 (d, 1 H, J=9 Hz), 5.83 (apparent t, 1 H, J=9 Hz), 6.50 (t, 1 H, J=10 Hz), 6.92 (br d, 1 H, J=12 Hz), 7.19 (s, 1 H), 9.21 (s, 1 H); mass spectrum m/z 620 (M+2); Analysis calculated for $C_{31}H_{43}N_3O_8S$: C, 60.27; H, 7.02; N, 6.80%. Found: C, 60.16; H, 6.82; N, 6.67%.

EXAMPLE 83

17-(2'-Fluoroethylamino)-11-keto-17-demethoxygeldanamycin

Mp 99–105° C. (dec); $^1$H-NMR (300 MHz, CDCl$_3$)δ1.04 (d, 3 H, J=7 Hz), 1.25 (d, 3 H, J=7 Hz), 1.50 (m, 2 H), 1.80 (m, 1 H), 1.81 (s, 3 H), 1.99 (s, 3 H), 2.31 (dd, 1 H, J=14 Hz, 5 Hz), 2.62 (dd, 1 H, J=14 Hz, 9 Hz), 3.31 (overlapping s, 6 H), 3.68 (dd, 1 H, J=9 Hz, 7 Hz), 3.77 (m, 1 H), 3.84 (m, 1 H), 4.10 (t, 1 H, J=6 Hz), 4.30 (d, 1 H, J=8 Hz), 4.54 (t, 1 H, J=5 Hz), 4.70 (t, 1 H, J=5 Hz), 5.19 (s, 1 H), 5.54 (d, 1 H, J=9Hz), 5.83 (t, 1 H, J=9 Hz), 6.28 (t, 1 H, J=6 Hz), 6.5) (t, 1 H, J=12 Hz), 6.93 (d, 1 H, J=12 Hz), 7.20 (s, 1 H), 9.17 (s, 1 H); mass spectrum m/z 591 (M+2); Analysis calculated for $C_{30}H_{40}N_3O_8 \cdot \frac{1}{12}CHCl_3$: C, 60.26; H, 6.84; N, 7.01%. Found: C, 60.57; H, 6.54; N, 6.87%.

EXAMPLE 84

17-(2'-Cyanoethylamino)-11-keto-17-demethoxygeldanamycin

Mp 102–107° C. (dec); $^1$H-NMR (300 MHz, CDCl$_3$) δ1.07 (d 2 H, J=7 Hz), 1.25 (d, 3 H, J=7 Hz), 1.53 (m, 2 H), 1.80 (m, 1 H), 1.81 (s, 3H), 2.00 (s, 3 H), 2.27 (dd, 1 H, J=14 Hz, 5 Hz), 2.58 (dd, 1 H, J=14Hz, 6 Hz), 2.69 (t, 2 11, J=8 Hz), 3.32 (s, 3 H), 3.33 (s, 3 H), 3.71 (dd, 1 H, J=9 Hz, 7 Hz), 3.80 (q, 2 H, J=7 Hz), 4.07 (m, 1 H), 4.29 (d, 1 H, J=8 Hz), 4.8 (br s, 2 H), 5.17 (s, 1 H), 5.55 (d, 1 H, J=9 Hz), 5.84 (apparent t, 1 H, J=9 Hz), 6.02 (t, 1 H, J=6 Hz), 6.51 (t, 1 H, J=11 Hz), 6.94 (br d, 1 H, J=12 Hz), 7.22 (s, 1 H), 9.09 (s, 1 H); mass spectrum m/z 619 (M+Na); Analysis calculated for $C_{31}H_{40}N_4O_8$: C, 62.40; H, 6.76; N, 9.39%. Found: C, 61.81; H, 6.45; N, 9.06%.

EXAMPLE 85

17-Azetidin-1-yl-11-keto-17-demethoxygeldanamycin

Mp 112–116° C. (dec); $^1$H-NMR (300 MHz, CDCl$_3$) δ1.02 (d, 3 H, J=7 Hz), 1.37 (d, 3 H, J=7 Hz), 1.48 (m, 2 H), 1.67 (m, 1 H), 1.82 (s, 3 H), 1.97 (s, 3 H), 2.22 (dd, 1 H, J=14 Hz, 5 Hz), 2.42 (m, 2 H), 2.58 (dd, 1 H, J=14 Hz, 7 Hz), 3.30 (overlapping s, 6 H), 3.61 (m, 1 H), 5.15 (t, 1 H, J=5 Hz), 4.17 (d, 1 H, J=8 Hz), 4.62 (t, 4 H, J=7 Hz), 4.80 (br s, 2 H), 5.19 (s, 1 H), 5.51 (d, 1 H, J=10 Hz), 5.76 (t, 1 H, J=10 Hz), 6.48 (t, 1 H, J=12 Hz), 6.90 (br d, 1 H, J=12 Hz), 6.97 (s, 1 H), 9.25 (s, 1 H); mass spectrum m/z 583 (M$^+$); Analysis calculated for $C_{31}H_{41}N_3O_8$: C, 63.79; H, 7.08; N, 7.20%. Found: C, 63.83; H, 7.11; N, 6.84%.

EXAMPLE 86

17-(3'-Hydroxyazetidin-1-yl)-11-keto-17-demethoxygeldanamycin

Mp 145° C. (foam); $^1$H-NMR (300 MHz, CDCl$_3$)δ1.0 (d, 3 H, J=4 Hz), 1.2–1.3 (m, 6 H), 1.4 (m, 2 H), 1.7 (m, 1 H), 1.8 (s, 3 H), 2.15 (s, 2 H), 2.2 (d, 1 H, J=4 Hz), 2.5 (m, 1 H), 3.3 (2 singlets, 6 H), 3.6 (m, 1 H), 3.8 (br s, 1 H), 4.15 (m, 1 H), 4.3 (d, 1 H, J=7 Hz), 4.35-4.5 (m, 2 H), 4.5–4.9 (m, 3 H), 5.0–5.2 (m, 3 H), 5.5 (d, 1 H, J=7 Hz), 5.8 (m, 1 H), 6.5 (t, 1 H, J=10 Hz), 6.9 (d, 1 H, J=14 Hz), 7.0 (s, 1 H), 9.2 (s, 1 H); mass spectrum m/z 622 (M+2); Analysis calculated for $C_{31}H_{43}N_3O_9 \cdot H_2O$: C, 60.28; H, 7.02; N, 6.80%. Found: C, 60.76; H, 7.10; N, 6.36%.

EXAMPLE 87

17-(3'-Methoxyazetidin-1-yl)-11-keto-17-demethoxygeldanamycin

Mp 128° C. (foam); $^1$H-NMR (300 MHz, CDCl$_3$)δ1.0 (d, 3 H, J=7 Hz), 1.25 (m, 6 H), 1.45 (m, 2 H), 1.6–1.85 (m, 4 H, contains methyl singlet), 1.9–2.1 (m, 4 H, contains methyl singlet), 2.1–2.3 (m, 1 H), 2.95–3.25 (m, 1 H), 3.3 (m, 9 H, contains 3 methyl singlets), 3.6 (m, 1 H), 4.04.3 (m, 3 H), 4.35-4.5 (m, 2 H), 4.6–4.8 (m, 2 H), 5.1 (br s, 2 H), 5.2 (s, 1 H), 5.5 (d, 1 H, J=10 Hz), 5.8 (m, 1 H), 6.5 (t, 1 H, J=12 Hz), 6.9 (d, 1 H, J=12 Hz), 7.0 (s, 1 H), 9.25 (s, 1 H); mass spectrum m/z 636(M+Na); Analysis calculated for $C_{32}H_{43}N_3O_9$: C, 62.63; H, 7.06; N, 6.85%. Found: C, 62.23; H, 7.19; N, 6.70%.

EXAMPLE 88

17-Methylamino-11-(2'-morpholinoethylamino)-17-demethoxygeldanamycin

In a dry flask, sodium triacetoxyborohydride (152 mg, 0.72 mmol) in dichloroethane (4 mL) was sonicated until a fine suspension was formed. The mixture was removed from the sonicator and treated with N-aminoethylmc rpholine (47

μ, 0.36 mmol) and a few crystals of sodium sulfate. 11-Keto-17-methylamino-17-demethoxygeldanamycin (100 mg, 0.18 mmol) was then added and the mixture stirred at room temperature for 24 hours. The reaction mixture was washed with saturated sodium carbonate and brine and then dried over sodium sulfate. The solvent was removed by rotary evaporation and the crude product purified by column chromatography (silica gel, 10% methanol in methylene chloride) to give the title compound as a purple solid; Yield 87 mg, (71%), mp 119–120° C.; $^1$H-NMR (300 MHz, CDCl$_3$)δ0.90 (d, 3 H, J=7 Hz), 1.00 (d, 3 H, J=7 Hz), 1.42 (m, 2 H), 1.59 (m, 1 H), 1.65 (s, 3 H), 1.95 (s, 3 H), 2.03 (br s 1 H), 2.25 (dd, 1 H, J=8 Hz), 2.68 (m, 3 H), 2.81 (m, 2 H), 3.15 (d, 3 H, J=7 Hz), 3.22 (s, 3 H), 3.28 (s, 3 H), 3.52 (m, 1 H), 3.62 (t, 4 H, J=4 Hz), 4.44 (br d, 1 H, J=10 Hz), 4.75 (br s, 1 H), 5.40 (s, 1 H), 5.55 (d, 1 H, J=10 Hz), 5.78 (dd, 1 H, J=8 Hz), 6.28 (d, 1 H, J=7 Hz), 6.45 (t, 1 H, J=13 Hz), 7.00 (m, 1 H), 7.05 (s, 1 H), 9.40 (s, 1 H); mass spectrum m/z 6,72 (M$^+$).

The compounds of Examples 89–95 were prepared from 11-keto-17-(methylamino)-17-demethoxygeldanamycin and the appropriate amines using the reductive amination method of Example 88.

EXAMPLE 89

11-Benzylamino-17-methylamino-17-demethoxygeldanamycin Mp 123–126° C.; $^1$H-NMR (300 MHz, CDCl$_3$)δ0.91 (d, 3H, J=8 Hz), 0.98 (d, 3 H, J=8 Hz), 1.35 (m, 1 H), 1.58 (m, 2 H), 1.66 (m, 1 H), 1.70 (s, 3 H), 1.95 (s, 3 H), 2.32 (dd, 1 H, J=8 Hz), 2.75 (dd, 1 H, J=8 Hz, 12 Hz), 2.93 (m, 1 H), 3.08 (s, 4 H), 3.12 (d, 3 H, J=8Hz), 3.15 (s, 6 H), 3.46 (d, 1 H, J=8Hz), 3.61 (d, 1 H, J=24Hz), 3.78 (d, 1 H, J=24 Hz), 4.30 (d, 1 H, J=8 Hz), 4.75 (br s, 2 H), 5.35 (s, 1 H), 5.70 (m, 2 H), 6.28 (d, 1 H, J=8 Hz), 6.43 (t, 1 H, J=12 Hz), 7.01 (br d, 1 H, J=16 Hz), 7.08 (s, 1 H), 7.20 (m, 5 H), 9.42 (s, 1 H); mass spectrum m/z 649 (M+1).

EXAMPLE 90

11-Cyclopropylamino-17-methylamino-17-demethoxygeldanamycin

Mp 120–123° C.; $^1$H-NMR (300 MHz, CDCl$_3$)δ0.30 (m, 4 H), 0.93 (d, 3 H, J=8 Hz), 1.02 (d, 3 H, J=8 Hz), 1.40 (m, 2 H), 1.72 (s, 3 H), 1.80 (br s, 1 H), 1.99 (s, 3 H), 2.15 (s, 1 H), 2.32 (dd, 1 H, J=8Hz, 13 Hz), 3.00 (m, 1 H), 3.18 (d, 3 H, J=7Hz), 3.28 (s, 3 H), 3.30 (s, 3 H), 3.57 (m, 1 H), 4.39 (d, 1 H, J=8 Hz), 4.84 (br s, 2 H), 5.63 (d, 1 H, J=8 Hz), 5.80 (dd, 1 H, J=8 Hz, 8 Hz), 6.32 (d, 1 H, J=7 Hz), 6.51 (t, 1 H, J=13 Hz), 7.01 (br d, 1 H, J=17 Hz), 7.09 (s, 1 H), 9.44 (s, 1 H); mass spectrum m/z 600 (M+1).

EXAMPLE 91

11-Isoamylamino-17-methylamino-17-demethoxygeldanarnycin

Mp 108–110° C.; $^1$H-NMR (300 MHz, CDCl$_3$)δ0.90 (d, 3 H, J=8 Hz), 1.00 (d, 3 H, J=8 Hz), 1.22–1.60 (m, 5 H), 1.63 (m, 1 H), 1.65 (s, 3 H), 1.95 (s, 3 H), 2.29 (dd, 1 H, J=7 Hz), 2.53 (m, 1 H), 2.75 (m, 2 H), 2.90 (m, 1 H), 3.13 (d, 3 H, J=7 Hz), 3.23 (s, 3 H), 3.28 (s, 3 H), 3.52 (m, 1 H), 4.90 (br s, 2 H), 5.35 :s, 1 H), 5.60 (br d, 1 H, J=8), 5.75 (dd, 1 H, J=8 Hz), 6.30 (d, 1 H, J=7 Hz), 6.43 (t, 1 H, J=12 Hz), 7.02 (s, 1 H), 7.09 (br s, 1 H), 9.38 (s, 1 H); mass spectrum m/z 629 (M+1)

EXAMPLE 92

11-(2'-Hydroxyethylamino)-17-methylamino-17-demethoxygeldanamycin

Mp (oil); $^1$H-NMR (300 MHz, CDCl$_3$)δ0.95 (d, 3 H, J=7 Hz), 1.09 (d, 3 H, J=7 Hz), 1.45 (m, 1 H), 1.58 (m, 2 H), 1.72 (s, 3 H), 2.00 (s, 3 H), 2.30 (dd, 1 H, J=8 Hz), 3.02 (m, 9 H), 3.20 (d, 3 H, J=7 Hz), 3.28 (s, 3 H), 3.35 (s, 3 H), 3.62 (m, 3 H), 4.55 (br s, 1 H), 4.90 (br s, 2 H), 5.40 (br s, 1 H), 5.63 (d, 1 H, J=10 Hz), 5.81 (dd, 1 H, J=8 Hz), 6.36 (d, 1 H, J=7 Hz), 6.50 (t, 1 H, J=13 Hz), 7.08 (m, 1 H), 7.12 (s, 1 H), 9.40 (s, 1 H); mass spectrum m/z 603 (M+1).

EXAMPLE 93

11-(3'-Dimethylaminopropylamino)-17-methylamino-17-demethoxygeldanamycin

Mp 105–108° C.; $^1$H-NMR (300 MHz, CDCl$_3$)δ0.95 (d, 3 H, J=7 Hz), 1.03 (d, 3 H, J=7 Hz), 1.48 (m, 1 H), 1.65 (m, 3 H), 1.70 (s, 3 H), 1.98 (s, 3 H), 2.20 (s, 6 H), 2.28 (m, 3 H), 2.65 (m, 1 H), 2.70 (m, 2 H), 2.84 (dd, 1 H, J=7 Hz), 2.90 (m, 1 H), 3.20 (d, 3 H, J=7 Hz), 3.29 (s, 3 H), 3.33 (s, 3 H), 3.57 (m, 1 H), 4.48 (d, 1 H, J=13 Hz), 4.80 (br s, 2 H), 5.41 (br s, 1 H), 5.62 (br d, 1 H, J=13 Hz), 5.81 (dd, 1 H, J=8 Hz), 6.32 (d, 1 H, J=7 Hz), 6.49 (t, 1 H, J=13 Hz), 7.09 (m, 1 H), 7.10 (s, 1 H), 9.43 (s, 1 H); mass spectrum m/z 644 (M$^+$+1).

EXAMPLE 94

11-Allylamino-17-methylamino-17-demethoxygeldanamycin

Mp 123–125° C.; $^1$H-NMR (300 MHz, CDCl$_3$)δ0.95 (d, 3 H, J=7 Hz), 1.03 (d, 3 H, J=7Hz), 1.41 (m, 1 H), 1.52 (m, 1 H), 1.72 (s, 3 H), 1.84 (m, 2 H), 2.00 (s, 3 H), 2.36 (dd, 1 H, J=7 Hz), 2.80 (m, 2 H), 3.00 (m, 1 H), 3.20 (d, 3 H, J=7 Hz), 3.25 (s, 3 H), 3.32 (s, 3 H), 3.58 (m, 1 H), 4.42 (d, 1 H, J=10 Hz), 4.80 (br s, 2 H), 5.08 (dd, 2 H, J=16 Hz), 5.40 (s, 1 H), 5.65 (d, 1 H, J=13 Hz), 5.83 (m, 2 H), 6.32 (d, 1 H, J=7 Hz), 6.50 (t, 1 H, J=13 Hz), 7.05 (m, 1 H), 7.10 (s, 1 H), 9.45 (s, 1 H); mass spectrum m/z 599 (M$^+$+1).

EXAMPLE 95

17-Azetidin-1-yl-11-oximino-17-demethoxygeldanamycin

To a solution of 17-azetidin-1-y-11-keto-17-demethoxygedanamycin (0.10 g, 0.17 mmol) in ethanol was added a solution of hydroxylamine hydrochloride (0.10 g, 1.42 mmol) and triethylamine (0.2 mL) in ethanol. The reaction mixture was stirred at room temperature for 2.5 hours and thereafter the solvent was removed by rotary evaporation and the residue dissolved in CHCl$_3$. The chloroform solution was washed with water, dried over sodium sulfate and the solvent removed by rotary evaporation. The residue was purified by column chromatography (silica gel, 15% acetone in CHCl$_3$) to give 17-azetidino-11-oximino-17-demethoxygeldanamycin (70 mg, 68 %), as a purple powder. Mp 130–145° C. (dec); $^1$H-NMR (300 MHz, CDCl$_3$)δ0.98 (d, 3 H, J=7 Hz), 1.17 (d, 3 H, J=7 Hz), 1.37 (m, 2 H), 1.54 (m, 1 H), 1.81 (s, 2 1), 1.95 (s, 3 H), 2.25 (dd, 1 H, J=14 Hz, 4 Hz), 2.41 (m, 2 H), 2.61 (dd, 1 H, J=14 Hz, 3 Hz), 3.20 (s, 3 H), 3.28 (s, 3 H), 4.02 (m, 2 H), 4.13 (d, 1 H, J=8 Hz), 4.65 (t 1 H, J=8 Hz), 5.01 (br exchangeable, 2 H), 5.09 (s, 1 H), 5.37 (br d, 1 H, J=10 Hz), 5.74 (t, 1 H, J=10 Hz), 6.45 (t, 1 H, J=12 Hz), 6.89 (br s, 1 H), 6.97 (s, 1 H), 9.27 (s, 1 H); mass spectrum m/z 586 (M −2); Analysis calculated for C$_{31}$H$_{42}$N$_4$O$_8$: C, 62.19; H, 7.07; N, 9.36%. Found: C, 61.76; H, 6.88; N, 9.14%.

The compounds of Examples 96–99 were prepared according to the method of Example 95 from the appropriate 11-keto-17-demethoxygeldanamycin.

EXAMPLE 96

17-(2'-Methoxyethylamino)-11-oximino-17-demethoxygeldanamycin

Mp 119–127° C. (dec); $^1$H-NMR (300 MHz, CDCl$_3$) δ1.03 (d, 3 H, J=7 Hz), 1.18 (d, 3 H, J=7 Hz), 1.39 (m, 1 H), 1.84 (s, 3 H), 1.86 (m, 1 H), 1.98 (s, 3 H), 2.32 (dd, 1 H, J=14Hz, 4Hz), 2.68 (dd, 1 H, J=14 Hz, 7 Hz), 3.21 (s, 3 H), 3.27(s, 3 H), 3.38 (s, 3 H), 3.58 (m, 2 H), 3.62 (m, 2 H), 3.95 (m, 2 H), 4.12 (d, 1 H, J=8 Hz), 4.90 (br s, 1 H), 5.11 (s, 1 H), 5.38 (br d, 1 H, J=8 Hz), 5.75 (t, 1 H, J=10 Hz), 6.50 (m, 2 H), 6.9 (br s, 1 H), 7.17 (s, 1 H), 9.25 (s, 1 H); mass spectrum m/z 616 (M+).

EXAMPLE 97

17-CyClopropylamino-11-oximino-17-demethoxygeldananycin

Mp (amorphous); $^1$H-NMR (300 MHz, CDCl$_3$)δ0.7–0.9 (m, 4 H), 1.0 (d, 3 H, J=7 Hz), 1.2 (d, 3 H, J=7 Hz), 1.3–1.6 (m, 3 H), 1.8 (s, 3 H), 1.95 (m, 1 H), 2.0 (s, 3 H), 2.7 (m, 1 H), 2.9 (m, 2 H), 3.2 (s, 3 H), 3.3 (s, 3 H), 4.05 (br s, 2 H), 4.15 (d, 1 H, J=7 Hz), 5.13 (d, 2 H, J=10 Hz), 5.45 (d, 1 H, J=10 Hz), 5.8 (t, 1 H, J=10 Hz), 6.3 (d, 1 H, J=3 Hz), 6.48 (t, 1 H, J=10 Hz), 6.9 (br d, 1 H, J=10 Hz), 7.08 (m, 1 H), 7.15 (s, 1 H), 9.28 (br s, 1 H); mass spectrum m/z 621 (M+Na); Analysis calculated for $C_{31}H_{42}N_4O_8 \cdot 0.5\ H_2O$: C, 61.27; H, 7.13; N, 9.22%. Found: C, 61.74; H, 7.25; N, 8.71%.

EXAMPLE 98

17-lsopropylamino-11-oximino-17-demethoxygeldanamycin

Mp 158–160° C.; $^1$H-NMR (300 MHz, CDCl$_3$)δ1.0 (d, 3 H, J=7 Hz), 1.15 (d, 3 H, J=7 Hz), 1.2 (d, 3 H, J=7 Hz), 1.3 (d, 3 H, J=7 Hz), 1.45–1.6 (br t, 1 H), 1.7–1.9 (m, 4 H), 2.0 (s, 3 H), 2.2 (br d, 1 H, J=14), 2.75 (t, 1 H, J=14 Hz), 3.15 (s, 3 H), 3.25 (s, 3 H), 3.84.05 (m, 3 H), 4.1 (d, 1 H, J=10), 5.1 (s, 1 H), 5.25–5.5 (br d, 3 H), 5.7 (t, 1 H, J=10 Hz), 6.2 (d, 1 H, J=10 Hz), 6.4 (t, 1 H, J=1 Hz), 6.75 (br d, 1 H), 7.1 (s, 1 H), 9.25 (br s, 1 H); mass spectrum m/z 623 (M+Na); Analysis calculated for $C_{31}H_{44}N_4O_8 \cdot 1.5\ H_2O$: C, 59.32; H, 7.55; N, 8.93%. Found: C, 59.27H, 7.07; N, 8.66%.

EXAMPLE 99

17-Allylamino-11-oximino-17-demethoxygeldanamycin

Mp 135° C.; mass spectrum m/z 621 (M+Na).

We claim:
1. A compound of the formula

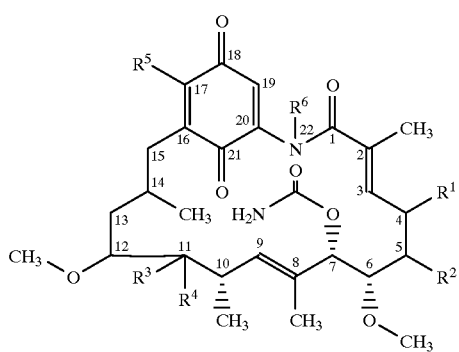

I and pharmaceutically acceptable salts thereof;
wherein $R^1$ and $R^2$ are both hydrogen;
$R^3$ is hydrogen and $R^4$ is selected from the group consisting of $OR^{10}$, $NHR^8$ and halo wherein $R^{10}$ is selected from the group consisting of hydrogen, $R^{11}C(=O)—$, and $R^{11}SO_2—$ and $R^{12}R^{13}NSO_2NHC(=O)—$, wherein $R^{11}$ is selected from the group consisting of amino, $(C_1–C_8)$alkyl, amino$(C_1–C_8)$alkyl, hydroxy $(C_1–C_8)$alkyl, phenyl and naphthyl; and $R^{12}$ and $R^{13}$ are selected from the group consisting of hydrogen, $(C_1–C_8)$alkyl, amino$(C_1–C_8)$alkyl, dimethylamino$(C_1–C_8)$alkyl, cyclo$(C_3–C_8)$alkyl, phenyl and naphthyl; or $R^{12}$ and $R^{13}$ together with the nitrogen to which they are attached form a heterocyclic residue selected from the group consisting of aziridinyl, azetidinyl, pyrrolidinyl, piperidinyl, thiazolidinyl, oxazolidinyl, morpholino, piperazinyl, 4-$(C_1–C_4)$ alkylpiperidinyl and N-$(C_1–C_4)$piperazinyl; and said alkyl, phenyl and naphthyl groups may be substituted with one or more residues selected from the group consisting of $(C_1–C_8)$alkyl, halo, nitro, amino, azido and $(C_1–C_8)$alkoxyl;

or $R^3$ and $R^4$ together form a group of the formula

=J wherein J is selected from O and NOH:

$R^5$ is $NR^8R^9$ wherein $R^8$ and $R^9$ are independently selected from the group consisting of hydrogen, $(C_1–C_3)$alkyl, $(C_3–C_8)$cycloalkyl, $(C_2–C_8)$ alkenyl and $(C_2–C_8)$ alkynyl; wherein said alkyl, alkenyl and alkynyl are optionally substituted wherein said substituents are selected from the group consisting of halo, cyano, mercapto, $(C_1–C_8)$alkylthio, optionally substituted amino, hydroxyl, $(C_1–C_8)$ alkoxyl, carboxyl, amidino, acylamino, and $(C_2–C_6)$hetarocycloalkyl and $(C_2–C_6)$ heterocycloaryl groups selected from the group comprising imidazalolyl, furyl, tetrahydrofuryl; and if comprising more than two carbon atoms may be branched, cyclic or unbranched or combinations of branched, cyclic and unbranched groups; or $R^8$ and $R^9$ together with the nitrogen to which they are attached form a heterocyclic residue selected from the group consisting of aziridinyl, azetidinyl and pyrrolidinyl; or $R^5$ is $R^{14}O$ wherein $R^{14}$ is hydrogen or $(C_1–C_8)$alkyl and $R^6$ is hydrogen or a group of the formula

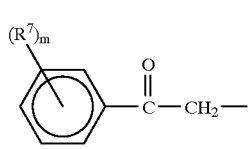

A wherein m is 0 or an integer from 1–5 ard each $R^7$ is independently selected from halo, azido, nitro, $(C_1–C_8)$ alkyl, $C_1–C_8$alkoxyl, phenyl and naphthyl, cyano and $NR^8R^9$ wherein $R^8$ and $R^9$ are as defined above; with the proviso that when $R^5$ is $OR^{14}$ and $R^{10}$ is $R^{11}C$ $(=O)$, $R^{11}$ cannot be methyl.

2. The compound of claim 1 wherein $R^3$ and $R^4$ together form a group of the formula =O.

3. The compound of claim 1 wherein $R^3$ and $R^4$ together form a group of the formula =NOH.

4. A compound of the formula

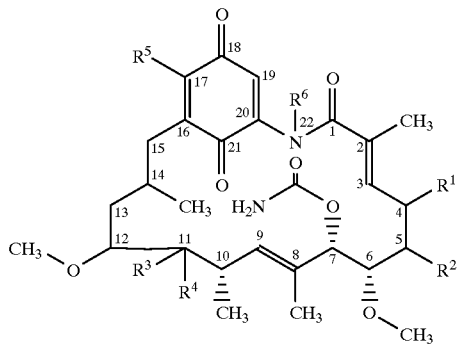

I and pharmaceutically acceptable salts thereof;
wherein $R^1$ and $R^2$ together form a single bond; $R^3$ and $R^4$ together form a group of the formula

=J wherein J is selected from O and NOH:
$R^5$ is $NR^8R^9$ wherein $R^8$ and $R^9$ are independently selected from the group consisting of hydrogen, $(C_1-C_8)$alkyl, $(C_3-C_8)$ cycloalkyl, $(C_2-C_8)$ alkenyl and $(C_2-C_8)$ alkynyl; wherein said alkyl, alkenyl and alkynyl are optionally substituted wherein said substituents are selected from the group consisting of halo, cyano, mercapto, $(C_1-C_8)$alkylthio, optionally substituted amino, hydroxyl, $(C_1-C_8)$ alkoxyl, carboxyl, amidino, acylamino, and $(C_2-C_6)$heterocycloalkyl and $(C_2-C_6)$ heterocycloaryl groups selected from the group comprising furyl, tetrahydrofuryl; and if comprising more than two carbon atoms may be branched, cyclic or unbranched or combinations of branched, cyclic and unbranched groups; or $R^8$ and $R^9$ together with the nitrogen to which they are attached form a heterocyclic residue selected from the group consisting of aziridinyl, azetidinyl and pyrrolidinyl; or $R^5$ is $R^{14}O$ wherein $R^{14}$ is hydrogen or $(C_1-C_8)$alkyl and $R^6$ is hydrogen or a group of the formula

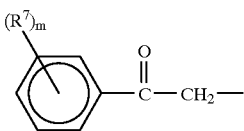

A wherein m is 0 or an integer from 1–5 and each $R^7$ is independently selected from halo, azido, nitro, $(C_1-C_8)$ alkyl, $C_1-C_8$alkoxyl, phenyl and naphthyl, cyano and $NR^8R^9$ wherein $R^8$ and $R^9$ are as defined above; with the proviso that when $R^1$ and $R^2$ together form a single bond and $R^3$ is hydrogen and $R^4OR^{10}$ and $R^{10}$ is hydrogen, $R^5$ cannot be $OR^{14}$, wherein $R^{14}$ is hydrogen or methyl, or $NR^8R^9$ wherein $HNR^8R^9$ is selected from the group consisting of ammonia, methylamine, ethylamine, propylamine, butylamine, pentylamine, hexylamine, heptylamine, octylamine, allylamine, β-hydroxyethylamine, β-chloroethylamine, β-glycoyethylamine, aminobutylamine, adamantylmethylamine, cyclcopropylamine, cyclopentylamine, cyclohexylamine, cycloheptylamine, cyclooctylamine, benzylamine, phenethylamine, ethyleneamine, pyrrolidine, piperidine, dimethylamine, aminoethylamine, diglycolamine, β-morpholinoethylamine, β-piperidinoethylamine, picolylamine, β-pyrrolidinoethylamine, β-pyridinylethylamine, β-methoxyethylamine, and β-N-methylaminoethylamine; and when $R^5$ is $OR^{14}$ and $R^{10}$ is $R^{11}C(=O)$, $R^{11}$ cannot be methyl.

5. The compound of claim 3 wherein $R^3$ and $R^4$ together form a group of the formula =O.

6. The compound of claim 3 wherein $R^3$ and $R^4$ together form a group of the formula =NOH.

7. A method of inhibiting the growth of SKBr³ breast cancer cells comprising administering an effective amount of a compound of claim 1 to a mammal in need of such treatment.

* * * * *